(12) United States Patent
Carreno et al.

(10) Patent No.: US 7,034,121 B2
(45) Date of Patent: Apr. 25, 2006

(54) ANTIBODIES AGAINST CTLA4

(75) Inventors: Beatriz M. Carreno, Acton, MA (US); Clive Wood, Boston, MA (US); Katherine Turner, Acton, MA (US); Mary Collins, Natick, MA (US); Gary S. Gray, Brookline, MA (US); Donna Morris, Salem, NH (US); Denise O'Hara, Reading, MA (US); Paul R. Hinton, Fremont, CA (US); Naoya Tsurushita, Palo Alto, CA (US)

(73) Assignee: Genetics Institue, LLC, Cambridge, MA (US)

( * ) Notice: Subject to any disclaimer, the term of this patent is extended or adjusted under 35 U.S.C. 154(b) by 0 days.

(21) Appl. No.: 09/772,103

(22) Filed: Jan. 26, 2001

(65) Prior Publication Data
US 2002/0039581 A1 Apr. 4, 2002

Related U.S. Application Data

(60) Provisional application No. 60/178,473, filed on Jan. 27, 2000.

(51) Int. Cl.
*C07K 16/28* (2006.01)
*A61K 39/395* (2006.01)

(52) U.S. Cl. .............................. 530/387.3; 530/387.1; 530/387.9; 530/388.1; 530/388.2; 530/388.22; 530/388.7; 530/388.73; 530/388.75; 530/391.1; 530/391.7; 530/395; 424/133.1; 424/141.1; 424/144.1; 424/152.1; 424/153.1; 424/154.1

(58) Field of Classification Search ............. 530/387.1, 530/387.3, 387.9, 388.1, 388.2, 388.22, 388.7, 530/388.73, 388.75, 351.1, 391.7, 350, 395
See application file for complete search history.

(56) References Cited

U.S. PATENT DOCUMENTS 5,773,001 A * 6/1998 Hamann et al.
5,821,332 A * 10/1998 Godfrey et al.
5,994,511 A * 11/1999 Lowman et al.
6,207,156 B1 * 3/2001 Kuchroo et al.
2002/0086014 A1 * 7/2002 Korman et al.

FOREIGN PATENT DOCUMENTS

WO WO 98/56417 A 12/1998

OTHER PUBLICATIONS

Bendig Methods: A Companion to Methods in Enzymology 1995; 8:83-93.*
Swiss-Prot #43489, TNR4_Human, Release 45, Sep. 2003.*
Godfrey et al. J. Exp. Med. 1994; 180:757-762.*
Colombatti, M. et al., "Selective killing of target cells by antibody-ricin A chain or antibody-gelonin hybrid molecules: comparison of cytotoxic potency and use in immunoselection procedures," *J. Immunol.*, Dec. 1983;131(6):3091-5.
Duke-Cohan, J. S. et al., "Targeting of an activated T-cell subset using a bispecific antibody-toxin conjugate directed against CD4 and CD26," *Blood*, Oct. 1, 1993;82(7):2224-34.
Koehler, M. et al., "XomaZyme-CD5 immunotoxin in conjunction with partial T cell depletion for prevention of graft rejection and graft-versus-host disease after bone marrow transplantation from matched unrelated donors," *Bone Marrow Transplant.*, May 1994; 13(5):571-5.
Razi-Wolf, Ziba et al., "Evidence for an additional ligand, distinct from B7, for the CTLA-4 receptor," *Proc. Nat. Acad. Sci. U.S.A.*, 90(23):11182-6 (1993).
Sievers, E.L. et al., "Selective ablation of acute myeloid leukemia using antibody-targeted chemotherapy: a phase I study of an anti-CD33 calicheamicin immunoconjugate," *Blood* Jun. 1, 1999;93(11):3678-84.
Vandenborre, K. et al., "Interaction of CTLA-4 (CD152) with CD80 or CD86 Inhibits human T-cell activation," *Immnunology*, 98(3):413-421 (1999).

* cited by examiner

*Primary Examiner*—Phillip Gambel
*Assistant Examiner*—Ilia Ouspenski
(74) *Attorney, Agent, or Firm*—Foley Hoag LLP

(57) ABSTRACT

The invention provides an antibody-toxic moiety conjugates comprising an antibody that specifically recognizes a molecule expressed on the surface of a T cell which is expressed only on T cells and is only expressed transiently on T cells upon T cell activation. Preferably, the T cell molecule is CTLA4. The invention further provides anti-CTLA4 antibodies and humanized forms thereof.

2 Claims, 22 Drawing Sheets

Anti-CTLA4 Abs #25, #26, and #29 defined three distinct epitopes on CTLA4

Anti-CTLA4 Abs #25, #26, and #29 defined three distinct epitopes on CTLA4

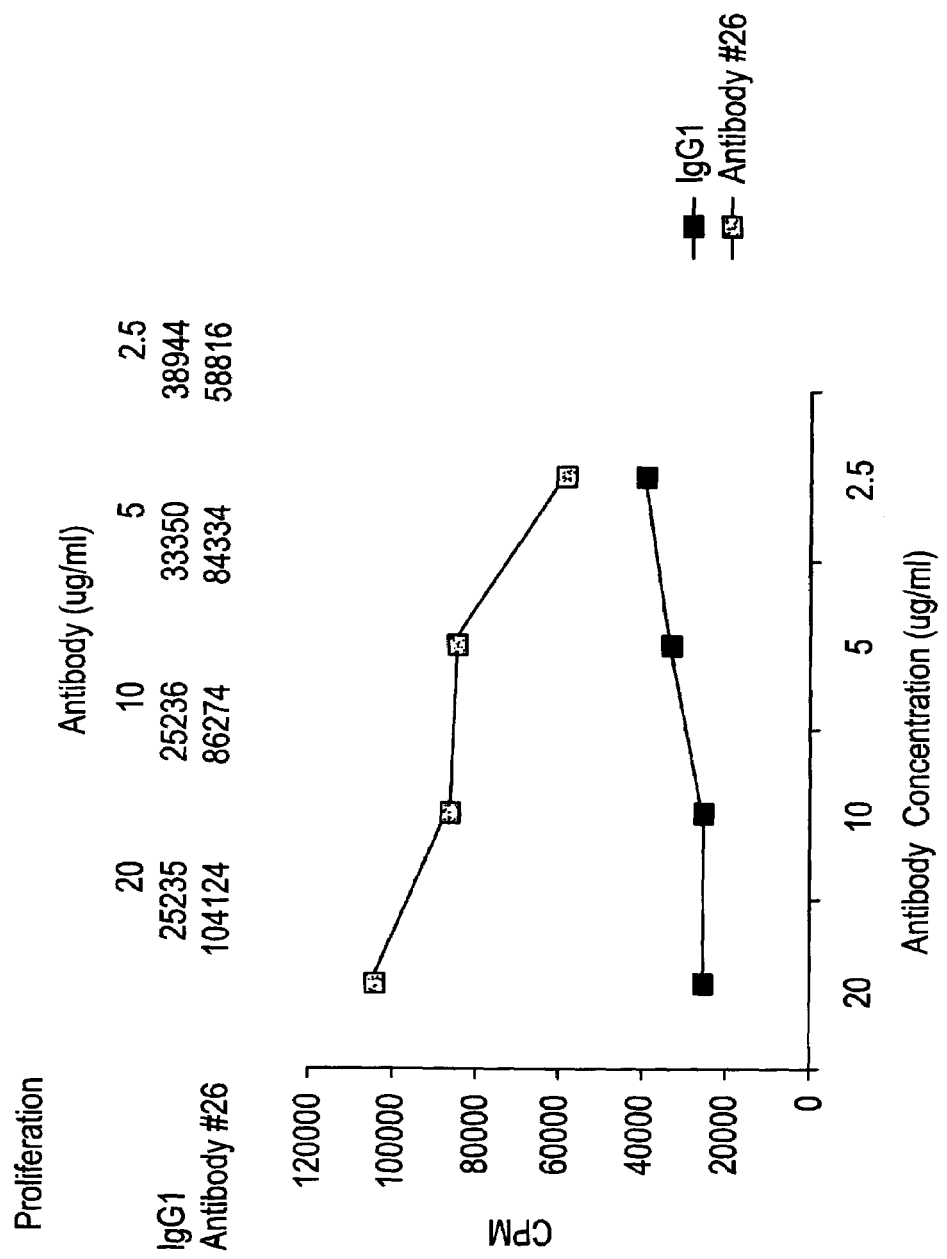

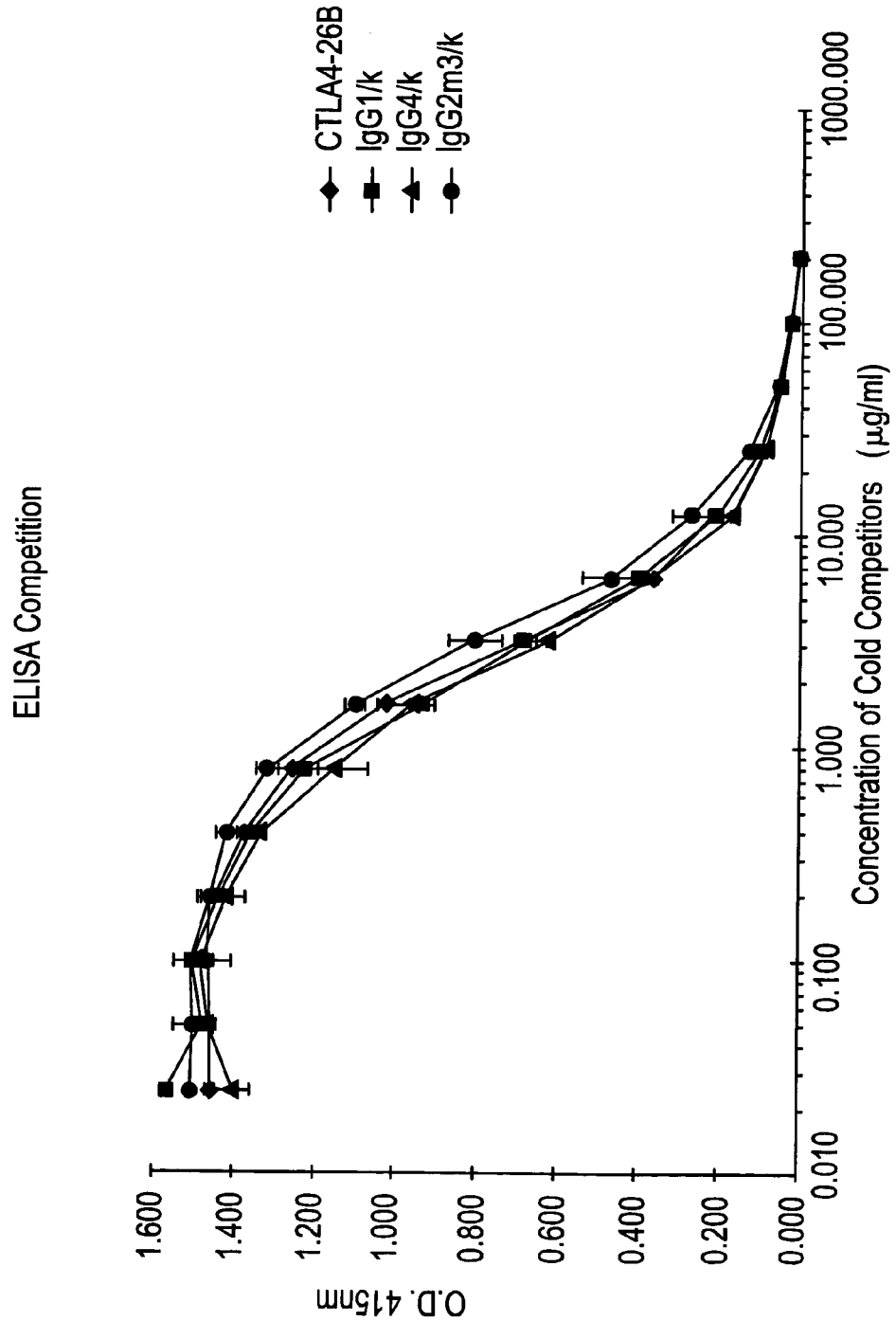

| Key | Name | Parameter | Gate |
|---|---|---|---|
| —— | 052199.016 | FL1-H | No Gate |
| —— | 052199.017 | FL1-H | No Gate |
| —— | 052199.001 | FL1-H | No Gate |
| —— | 052199.002 | FL1-H | No Gate |
| —— | 052199.003 | FL1-H | No Gate |
| —— | 052199.004 | FL1-H | No Gate |
| —— | 052199.005 | FL1-H | No Gate |

| Key | Name | Parameter | Gate |
|---|---|---|---|
| —— | 052199.016 | FL1-H | No Gate |
| —— | 052199.017 | FL1-H | No Gate |
| —— | 052199.006 | FL1-H | No Gate |
| —— | 052199.007 | FL1-H | No Gate |
| —— | 052199.008 | FL1-H | No Gate |
| —— | 052199.009 | FL1-H | No Gate |
| —— | 052199.010 | FL1-H | No Gate |

| Key | Name | Parameter | Gate |
|---|---|---|---|
| —— | 052199.016 | FL1-H | No Gate |
| —— | 052199.017 | FL1-H | No Gate |
| —— | 052199.018 | FL1-H | No Gate |
| —— | 052199.019 | FL1-H | No Gate |

FIG. 6D

| Name | Cell Line | Primary Ab | Competitor |
|---|---|---|---|
| | CHO.CTLA4 | FITC-CTLA4-26B | Cold CTLA4-26B |
| 052199.001 | ↓ | 125 ng | 2000 ng |
| 052199.002 | | | 1000 ng |
| 052199.003 | | | 500 ng |
| 052199.004 | | | 250 ng |
| 052199.005 | | | 100 ng |
| | | | IgG1/k |
| 052199.006 | | | 2000 ng |
| 052199.007 | | | 1000 ng |
| 052199.008 | | | 500 ng |
| 052199.009 | | | 250 ng |
| 052199.010 | | | 100 ng |
| 052199.016 | | ↓ | none |
| 052199.017 | | none | none |
| 052199.018 | CHO.B7.1 | 125 ng | none |
| 052199.019 | ↓ | none | none |

| Key | Name | Parameter | Gate |
|---|---|---|---|
| — | 052199.001 | FL1-H | No Gate |
| — | 052199.006 | FL1-H | No Gate |

| Key | Name | Parameter | Gate |
|---|---|---|---|
| — | 052199.002 | FL1-H | No Gate |
| — | 052199.007 | FL1-H | No Gate |

| Key | Name | Parameter | Gate |
|---|---|---|---|
| — | 052199.003 | FL1-H | No Gate |
| — | 052199.008 | FL1-H | No Gate |

| Key | Name | Parameter | Gate |
|---|---|---|---|
| — | 052199.004 | FL1-H | No Gate |
| — | 052199.009 | FL1-H | No Gate |

Jurkat CTLA4 NEGATIVE cell line

Jurkat CTLA-4 POSITIVE cell line

FIG. 9

HuCTLA4-Vk

```
TATATCTAGACCACCATGGATTTTCAAGTGCAGATCTTCAGCTTCCTGCTAATCAGTGCC
               M  D  F  Q  V  Q  I  F  S  F  L  L  I  S  A

TCAGTCATACTGTCCAGAGGAGATATCCAGATGACCCAGTCTCCATCCTCCCTATCCGCA
 S  V  I  L  S  R  G  D  I  Q  M  T  Q  S  P  S  S  L  S  A

TCTGTTGGGGACAGGGTCACCATAACCTGTAGTGCCACCTCAAGTATAACTTACATGTCC
 S  V  G  D  R  V  T  I  T  C  S  A  T  S  S  I  T  Y  M  S
                              ‾‾‾‾‾‾‾‾‾‾‾‾‾‾‾‾‾‾‾‾‾‾‾‾‾‾‾‾‾‾

TGGTATCAGCAGAAGCCAGGAAAGGCTCCCAAGCTTCTGATTTATGACACATCCAACCTG
 W  Y  Q  Q  K  P  G  K  A  P  K  L  L  I  Y  D  T  S  N  L
                                          ‾‾‾‾‾‾‾‾‾‾‾‾‾‾‾‾‾‾‾

GCTTCTGGGGTACCTAGCCGCTTCAGTGGCAGTGGGTCTGGGACCGACTACACACTCACA
 A  S  G  V  P  S  R  F  S  G  S  G  S  G  T  D  Y  T  L  T
‾‾‾‾‾                          =                 ‾     =

ATCAGCAGCCTGCAGCCAGAAGATTTTGCCACTTATTACTGCCAGCAGTGGAGTAGTTAC
 I  S  S  L  Q  P  E  D  F  A  T  Y  Y  C  Q  Q  W  S  S  Y
                        =                    ‾‾‾‾‾‾‾‾‾‾‾‾‾‾‾

CCGCTCACGTTCGGTGGAGGGACCAAGGTTGAGATAAAACGTAAGTAGAATCCAAAGTCT
 P  L  T  F  G  G  G  T  K  V  E  I  K
‾‾‾‾‾‾‾‾‾‾

AGATATA
```

FIG. 10

HuCTLA4-VH

TATATCTAGACCACCATGGCTGTCCTGGTGCTGTTCCTCTGCCTGGTTGCATTTCCAAGC
                M  A  V  L  V  L  F  L  C  L  V  A  F  P  S

TGTGTCCTGTCCCAGGTGCAGCTGCAAGAGTCAGGACCTGGCCTGGTGAAGCCCTCACAG
 C  V  L  S  Q  V  Q  L  Q  E  S  G  P  G  L  V  K  P  S  Q

ACACTGTCCTTGACTTGCACTGTCTCTGGGTTTTCATTAACCTCATATGGTGTATATTGG
 T  L  S  L  T  C  T  V  S  G  F  S  L  T  S  Y  G  V  Y  W

GTTCGCCAGCCTCCAGGAAAGGGTCTGGAGTGGCTGGGAGTAATATGGGCTGGTGGTACC
 V  R  Q  P  P  G  K  G  L  E  W  L  G  V  I  W  A  G  G  T

ACAAATTATAATTCGGCTCTCATGTCCAGACTGACAATCAGCAAAGACACATCCAAGAAC
 T  N  Y  N  S  A  L  M  S  R  L  T  I  S  K  D  T  S  K  N

CAAGTTTCCTTAAAACTCAGCAGTGTGACTGCAGCGGACACAGCCGTCTACTACTGTGCC
 Q  V  S  L  K  L  S  S  V  T  A  A  D  T  A  V  Y  Y  C  A

CGAGGCCCCCCGCACGCTATGATGAAGAGAGGCTATGCTATGGACTACTGGGGACAAGGA
 R  G  P  P  H  A  M  M  K  R  G  Y  A  M  D  Y  W  G  Q  G

ACCCTAGTCACAGTCTCCTCAGGTGAGTCCTTAAAACCTCTAGATATA
 T  L  V  T  V  S  S

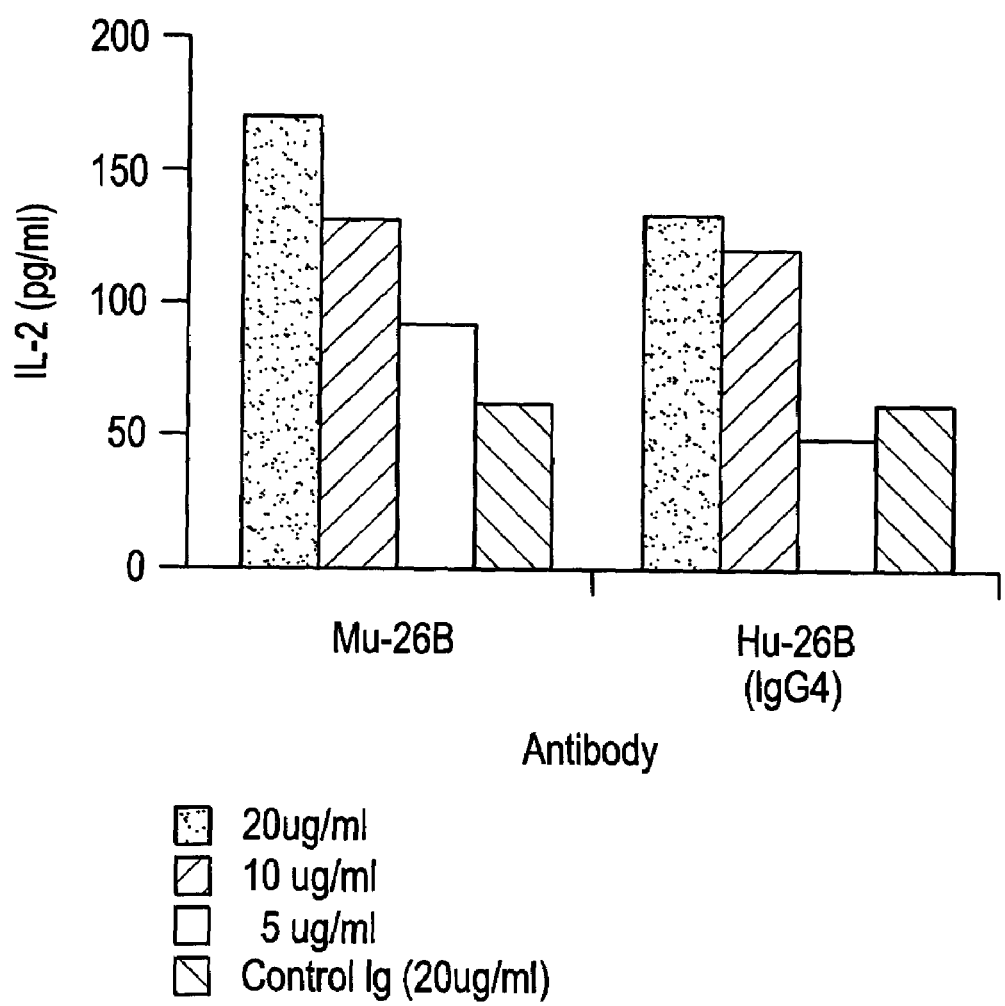

SEQUENCE LISTING

<160> NUMBER OF SEQ ID NOS: 10

<210> SEQ ID NO 1
<211> LENGTH: 672
<212> TYPE: DNA
<213> ORGANISM: Homo sapiens
<220> FEATURE:

<400> SEQUENCE: 1
atggcttgcc ttggatttca gcggcacaag gctcagctga acctggctgc caggacctgg        60

-continued

```
ccctgcactc tcctgttttt tcttctcttc atccctgtct tctgcaaagc aatgcacgtg    120
gcccagcctg ctgtggtact ggccagcagc cgaggcatcg ccagctttgt gtgtgagtat    180
gcatctccag gcaaagccac tgaggtccgg gtgacagtgc ttcggcaggc tgacagccag    240
gtgactgaag tctgtgcggc aacctacatg acggggaatg agttgacctt cctagatgat    300
tccatctgca cgggcacctc cagtggaaat caagtgaacc tcactatcca aggactgagg    360
gccatggaca cgggactcta catctgcaag gtggagctca tgtacccacc gccatactac    420
ctgggcatag caacggaac ccagatttat gtaattgatc cagaaccgtg cccagattct    480
gacttcctcc tctggatcct tgcagcagtt agttcggggt tgttttttta tagctttctc    540
ctcacagctg tttctttgag caaaatgcta agaaaagaa gccctcttac aacagggggtc    600 tatgtgaaaa tgcccccaac agagccagaa tgtgaaaagc aatttcagcc ttatttttatt    660 cccatcaatt ga                                                       672
```

<210> SEQ ID NO 2
<211> LENGTH: 223
<212> TYPE: PRT
<213> ORGANISM: Homo sapiens

<400> SEQUENCE: 2

```
Met Ala Cys Leu Gly Phe Gln Arg His Lys Ala Gln Leu Asn Leu Ala
  1               5                  10                  15

Thr Arg Thr Trp Pro Cys Thr Leu Leu Phe Phe Leu Leu Phe Ile Pro
             20                  25                  30

Val Phe Cys Lys Ala Met His Val Ala Gln Pro Ala Val Val Leu Ala
         35                  40                  45

Ser Ser Arg Gly Ile Ala Ser Phe Val Cys Glu Tyr Ala Ser Pro Gly
     50                  55                  60

Lys Ala Thr Glu Val Arg Val Thr Val Leu Arg Gln Ala Asp Ser Gln
 65                  70                  75                  80

Val Thr Glu Val Cys Ala Ala Thr Tyr Met Met Gly Asn Glu Leu Thr
                 85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Ala Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220
```

<210> SEQ ID NO 3
<211> LENGTH: 426
<212> TYPE: DNA
<213> ORGANISM: Mus musculus

<400> SEQUENCE: 3

```
atggctgtcc tggtgctgtt cctctgcctg gttgcatttc caagctgtgt cctgtcccag      60
gtgcagctga aggagtcagg acctggcctg gtggcgccct cacagagcct gtccatcact     120
tgcactgtct ctgggttttc attaaccagc tatggtgtat attgggttcg ccagcctcca     180
ggaaagggtc tggagtggct gggagtaata tagggctggt ggaaccacaa attataattc     240
ggctctatgt ccagactgag catcagcaaa gacaactcca agagccaagt tttcttaaaa     300
atgagcagtc tgcaaactga tgacacagcc atgtactact gtgccagggg cccccgcac      360
gctatgatga agagaggcta tgctatggac tactggggac aaggaacctc agtcatcgtc     420
tcctca                                                                 426
```

<210> SEQ ID NO 4
<211> LENGTH: 142
<212> TYPE: PRT
<213> ORGANISM: Mus musculus

<400> SEQUENCE: 4

```
Met Asp Val Leu Val Leu Phe Leu Cys Leu Val Ala Phe Pro Ser Cys
  1               5                  10                  15

Val Leu Ser Gln Val Gln Leu Lys Glu Ser Gly Pro Gly Leu Val Ala
             20                  25                  30

Pro Ser Gln Ser Leu Ser Ile Thr Cys Thr Val Ser Gly Phe Ser Leu
         35                  40                  45

Thr Ser Tyr Gly Val Tyr Trp Val Arg Gln Pro Pro Gly Lys Gly Leu
     50                  55                  60

Glu Trp Leu Gly Val Ile Trp Ala Gly Gly Thr Thr Asn Tyr Asn Ser
 65                  70                  75                  80

Ala Leu Met Ser Arg Leu Ser Ile Ser Lys Asp Asn Ser Lys Ser Gln
                 85                  90                  95

Val Phe Leu Lys Met Ser Ser Leu Gln Thr Asp Asp Thr Ala Met Tyr
            100                 105                 110

Tyr Cys Ala Arg Gly Pro Pro His Ala Met Met Lys Arg Gly Tyr Ala
        115                 120                 125

Met Asp Tyr Trp Gly Gln Gly Thr Ser Val Ile Val Ser Ser
    130                 135                 140
```

<210> SEQ ID NO 5
<211> LENGTH: 384
<212> TYPE: DNA
<213> ORGANISM: Mus musculus

<400> SEQUENCE: 5

```
atggatttc aagtgcagat tttcagcttc ctgctaatca gtgcctcagt catactgtcc       60
agaggacaaa atgttctcac ccagtctcca gcaatcatgc tgcatctcc aggggagaag      120
gtcaccatga cctgcagtgc cacctcaagt ataacttaca tgtcctggta ccagcagaag     180
tcaggatcct cccccagact cctgatttat gacacatcca acctggcttc tggagtccct     240
gttcgcttca gtggcagtgg gtctgggacc tcttactctc tcacaatcag ccgaatggag     300
gctgaagatg ctgccactta ttactgccag cagtggagta gttacccgct cacgttcggt     360
```

```
gctgggacca agctggagct gaaa                                              384
```

<210> SEQ ID NO 6
<211> LENGTH: 128
<212> TYPE: PRT
<213> ORGANISM: Mus musculus

<400> SEQUENCE: 6

```
Met Asp Phe Gln Val Gln Ile Phe Ser Phe Leu Leu Ile Ser Ala Ser
 1               5                  10                  15

Val Ile Leu Ser Arg Gly Gln Asn Val Leu Thr Gln Ser Pro Ala Ile
            20                  25                  30

Met Pro Ala Ser Pro Gly Glu Lys Val Thr Met Thr Cys Ser Ala Thr
        35                  40                  45

Ser Ser Ile Thr Tyr Met Ser Trp Tyr Gln Gln Lys Ser Gly Ser Ser
    50                  55                  60

Pro Arg Leu Leu Ile Tyr Asp Thr Ser Asn Leu Ala Ser Gly Val Pro
65                  70                  75                  80

Val Arg Phe Ser Gly Ser Gly Ser Gly Thr Ser Tyr Ser Leu Thr Ile
                85                  90                  95

Ser Arg Met Glu Ala Glu Asp Ala Ala Thr Tyr Tyr Cys Gln Gln Trp
            100                 105                 110

Ser Ser Tyr Pro Leu Thr Phe Gly Ala Gly Thr Lys Leu Glu Leu Lys
        115                 120                 125
```

<210> SEQ ID NO 7
<211> LENGTH: 413
<212> TYPE: DNA
<213> ORGANISM: Artificial Sequence
<220> FEATURE:
<223> OTHER INFORMATION: Description of Artificial Sequence:Humanized
      mouse

<400> SEQUENCE: 7

```
tctagaccac catggatttt caagtgcaga tcttcagctt cctgctaatc agtgcctcgt    60
catactgtcc agaggagata tccagatgac ccagtctcca tcctccctat ccgcatcgtt   120
ggggacaggg tcaccataac ctgtagtgcc acctcaagta acttacat gtcctgtatc    180
agcagaagcc aggaaaggct cccaagcttc tgatttatga cacatccaac ctggctctgg   240
ggtacctagc cgcttcagtg gcagtgggtc tgggaccgac tacacactca aatagcagc   300
ctgcagccag aagattttgc cacttattac tgccagcagt ggagtagtta ccctcacgt   360
tcggtggagg gaccaaggtt gagataaaac gtaagtagaa tccaaagtct aga          413
```

<210> SEQ ID NO 8
<211> LENGTH: 128
<212> TYPE: PRT
<213> ORGANISM: Artificial Sequence
<220> FEATURE:
<223> OTHER INFORMATION: Description of Artificial Sequence:Humanized
      mouse

<400> SEQUENCE: 8

```
Met Asp Phe Gln Val Gln Ile Phe Ser Phe Leu Leu Ile Ser Ala Ser
 1               5                  10                  15

Val Ile Leu Ser Arg Gly Asp Ile Gln Met Thr Gln Ser Pro Ser Ser
            20                  25                  30

Leu Ser Ala Ser Val Gly Asp Arg Val Thr Ile Thr Cys Ser Ala Thr
        35                  40                  45
```

```
Ser Ser Ile Thr Tyr Met Ser Trp Tyr Gln Gln Lys Pro Gly Lys Ala
        50                  55                  60

Pro Lys Leu Leu Ile Tyr Asp Thr Ser Asn Leu Ala Ser Gly Val Pro
 65                  70                  75                  80

Ser Arg Phe Ser Gly Ser Gly Ser Gly Thr Asp Tyr Thr Leu Thr Ile
                 85                  90                  95

Ser Ser Leu Gln Pro Glu Asp Phe Ala Thr Tyr Tyr Cys Gln Gln Trp
                100                 105                 110

Ser Ser Tyr Pro Leu Thr Phe Gly Gly Gly Thr Lys Val Glu Ile Lys
            115                 120                 125
```

<210> SEQ ID NO 9
<211> LENGTH: 460
<212> TYPE: DNA
<213> ORGANISM: Artificial Sequence
<220> FEATURE:
<223> OTHER INFORMATION: Description of Artificial Sequence:Humanized mouse

<400> SEQUENCE: 9

```
tctagaccac catggctgtc ctggtgctgt tcctctgcct ggttgcattt ccaagctgtg     60
tcctgtccca ggtgcagctg caagagtcag gacctggcct ggtgaagccc tcacagacac    120
tgtccttgac ttgcactgtc tctgggtttt cattaacctc atatggtgta tattgggttc    180
gccagcctcc aggaaagggt ctggagtggc tgggagtaat atgggctggt ggtaccacaa    240
attataattc ggctctcatg tccagactga caatcagcaa agacacatcc aagaaccaag    300
tttccttaaa actcagcagt gtgactgcag cggacacagc cgtctactac tgtgcccgag    360
gcccccgca cgctatgatg aagagaggct atgctatgga ctactgggga caaggaaccc    420
tagtcacagt ctcctcaggt gagtccttaa aacctctaga                          460
```

<210> SEQ ID NO 10
<211> LENGTH: 142
<212> TYPE: PRT
<213> ORGANISM: Artificial Sequence
<220> FEATURE:
<223> OTHER INFORMATION: Description of Artificial Sequence:Humanized mouse

<400> SEQUENCE: 10

```
Met Ala Val Leu Val Leu Phe Leu Cys Leu Val Ala Phe Pro Ser Cys
  1               5                  10                  15

Val Leu Ser Gln Val Gln Leu Gln Glu Ser Gly Pro Gly Leu Val Lys
                 20                  25                  30

Pro Ser Gln Thr Leu Ser Leu Thr Cys Thr Val Ser Gly Phe Ser Leu
             35                  40                  45

Thr Ser Tyr Gly Val Tyr Trp Val Arg Gln Pro Pro Gly Lys Gly Leu
        50                  55                  60

Glu Trp Leu Gly Val Ile Trp Ala Gly Gly Thr Thr Asn Tyr Asn Ser
 65                  70                  75                  80

Ala Leu Met Ser Arg Leu Thr Ile Ser Lys Asp Thr Ser Lys Asn Gln
                 85                  90                  95

Val Ser Leu Lys Leu Ser Ser Val Thr Ala Ala Asp Thr Ala Val Tyr
                100                 105                 110
```

-continued

```
Tyr Cys Ala Arg Gly Pro Pro His Ala Met Met Lys Arg Gly Tyr Ala
            115                 120                 125

Met Asp Tyr Trp Gly Gln Gly Thr Leu Val Thr Val Ser Ser
    130                 135                 140
```

US 7,034,121 B2

ANTIBODIES AGAINST CTLA4

RELATED APPLICATION

This application claims the benefit of U.S. Provisional Patent Application Ser. No. 60/178,473, filed Jan. 27, 2000, the contents of which are incorporated herein it their entirety by this reference.

BACKGROUND OF THE INVENTION

In order for T cells to respond to foreign proteins, two signals must be provided by antigen-presenting cells (APCs) to resting T lymphocytes (Jenkins, M. and Schwartz, R. (1987) *J. Exp. Med.* 165, 302–319; Mueller, D. L., et al. (1990) *J. Immunol.* 144, 3701–3709). The first signal, which confers specificity to the immune response, is transduced via the T cell receptor (TCR) following recognition of foreign antigenic peptide presented in the context of the major histocompatibility complex (MHC). The second signal, termed costimulation, induces T cells to proliferate and become functional (Lenschow et al. (1996) *Annu. Rev. Immunol.* 14:233). Costimulation is neither antigen-specific, nor MHC restricted and is thought to be provided by one or more distinct cell surface molecules expressed by APCs (Jenkins, M. K., et al. (1988) *J. Immunol.* 140, 3324–3330; Linsley, P. S., et al. (1991) *J. Exp. Med.* 173, 721–730; Gimmi, C. D., et al. (1991) *Proc. Natl. Acad. Sci. USA.* 88, 6575–6579; Young, J. W., et al. (1992) *J. Clin. Invest.* 90, 229–237; Koulova, L., et al. (1991) *J. Exp. Med.* 173, 759–762; Reiser, H., et al. (1992) *Proc. Natl. Acad. Sci. USA.* 89, 271–275; van-Seventer, G. A., et al. (1990) *J. Immunol.* 144, 4579–4586; LaSalle, J. M., et al. (1991) *J. Immunol.* 147, 774–80; Dustin, M. I., et al. (1989) *J. Exp. Med.* 169, 503; Armitage, R. J., et al. (1992) *Nature* 357, 80–82; Liu, Y., et al. (1992) *J. Exp. Med.* 175, 437–445).

The CD80 (B7-1) and CD86 (B7-2) proteins, expressed on APCs, are critical costimulatory molecules (Freeman et al. (1991) *J. Exp. Med.* 174:625; Freeman et al. (1989) *J. Immunol.* 143:2714; Azuma et al. (1993) *Nature* 366:76; Freeman et al. (1993) *Science* 262:909). B7-2 appears to play a predominant role during primary immune responses, while B7-1, which is upregulated later in the course of an immune response, may be important in prolonging primary T cell responses or costimulating secondary T cell responses (Bluestone (1995) *Immunity* 2:555).

One ligand to which B7-1 and B7-2 bind, CD28, is constitutively expressed on resting T cells and increases in expression after activation. After signaling through the T cell receptor, ligation of CD28 and transduction of a costimulatory signal induces T cells to proliferate and secrete IL-2 (Linsley, P. S., et al. (1991) *J. Exp. Med.* 173, 721–730; Gimmi, C. D., et al. (1991) *Proc. Natl. Acad. Sci. USA* 88, 6575–6579; June, C. H., et al. (1990) *Immunol. Today* 11, 211–6; Harding, F. A., et al. (1992) *Nature* 356, 607–609). A second ligand, termed CTLA4 (CD152) is homologous to CD28 but is not expressed on resting T cells and appears following T cell activation (Brunet, J. F. et al. (1987) *Nature* 328, 267–270). CTLA4 appears to be critical in negative regulation of T cell responses (Waterhouse et al. (1995) *Science* 270:985). Blockade of CTLA4 has been found to remove inhibitory signals, while aggregation of CTLA4 has been found to provide inhibitory signals that downregulate T cell responses (Allison and Krummel (1995) *Science* 270:932). The B7 molecules have a higher affinity for CTLA4 than for CD28 (Linsley, P. S., et al. (1991) *J. Exp. Med.* 174, 561–569) and B7-1 and B7-2 have been found to bind to distinct regions of the CTLA4 molecule and have different kinetics of binding to CTLA4 (Linsley et al. (1994) *Immunity* 1:793). A new molecule related to CD28 and CTLA4, ICOS, has been identified (Hutloff et al. (1999) *Nature* 397:263; WO 98/38216). If T cells are only stimulated through the T cell receptor, without receiving an additional costimulatory signal, they become nonresponsive, anergic, or die, resulting in downmodulation of the immune response.

The importance of the B7:CD28/CTLA4 costimulatory pathway has been demonstrated in vitro and in several in vivo model systems. Blockade of this costimulatory pathway results in the development of antigen specific tolerance in murine and human systems (Harding, F. A., et al. (1992) *Nature.* 356, 607–609; Lenschow, D. J., et al. (1992) *Science.* 257, 789–792; Turka, L. A., et al. (1992) *Proc. Natl. Acad. Sci. USA.* 89, 11102–11105; Gimmi, C. D., et al. (1993) *Proc. Natl. Acad. Sci USA* 90, 6586–6590; Boussiotis, V., et al. (1993) *J. Exp. Med.* 178, 1753–1763). Conversely, expression of B7 by B7 negative murine tumor cells induces T-cell mediated specific immunity accompanied by tumor rejection and long lasting protection to tumor challenge (Chen, L., et al. (1992) *Cell* 71, 1093–1102; Townsend, S. E. and Allison, J. P. (1993) *Science* 259, 368–370; Baskar, S., et al. (1993) *Proc. Natl. Acad. Sci.* 90, 5687–5690.). Therefore, manipulation of the costimulatory pathways offers great potential to stimulate or suppress immune responses in humans.

SUMMARY OF THE INVENTION

The present invention is based, at least in part, on the development of toxic moiety-conjugated forms of antibodies which specifically bind to activated T cells and inhibit them by targeting a transiently expressed molecule that is only expressed on T cells, such as CTLA4. In addition, the instant invention provides and characterizes a panel of antibodies that recognize CTLA4. Antibodies to CTLA4 have different functions, e.g., stimulatory or inhibitory, depending upon e.g., the region of the CTLA4 molecule to which they bind or whether they are presented in monovalent (e.g., soluble) or multivalent form (e.g., crosslinked). Accordingly these antibodies can be used to modulate T cell activation, and, thereby, to modulate the immune response.

In one aspect, the present invention pertains to an antibody-toxic moiety conjugate comprising: an antibody, or antigen binding portion thereof, that specifically recognizes a molecule expressed only on activated T cells and a toxic moiety.

In one embodiment, the antibody is specifically reactive with CTLA4. In a preferred embodiment, the antibody is specifically reactive with human CTLA4.

In another embodiment, the antibody is a monoclonal antibody.

In one embodiment, the antibody binds to a region of the CTLA4 molecule blocks the binding of CTLA4 to CD80 or CD86. In another embodiment, the antibody binds to a region of the CTLA4 in spatial proximity to the site of CTLA4 binding to a costimulatory molecule.

In one embodiment, the substitution of amino acid 83 in the amino acid sequence of human CTLA4 shown in SEQ ID NO:2 results in modulation of binding of the antibody.

In one embodiment, the toxic moiety is a carbohydrate. In a preferred embodiment, the carbohydrate is calicheamicin. In another embodiment, the toxic moiety is a naturally occurring bacterial product. In yet another embodiment, the toxic moiety is selected from the group consisting of ricin A chain and saporin.

In one embodiment, the antibody is humanized, wherein the antibody comprises an amino acid sequence shown in SEQ ID NO:8.

In another aspect, the invention pertains to a humanized antibody that is specially reactive with human CTLA4, wherein the antibody comprises an amino acid sequence shown in SEQ ID NO:10.

In yet another aspect, the invention pertains to a humanized antibody that is specifically reactive with human CTLA4, wherein the antibody comprises an amino acid sequence shown in SEQ ID NO:10.

In still another aspect, the invention pertains to a method of modulating the immune response comprising contacting a cell with an antibody-toxic moiety conjugate of claim 2.

In one embodiment, the antibody-toxic moiety conjugate is administered to a subject and the step of contacting is performed in vivo. In one embodiment, the subject is suffering from a disorder or condition that would benefit from downmodulation of an ongoing immune response wherein the disorder or condition is selected from the group consisting of: an autoimmune disorder, an immune response to a graft, an allergic response, an immune response to a therapeutic protein. In another embodiment, the step of contacting is performed in vitro.

In another embodiment, the antibody comprises an amino acid sequence shown in SEQ ID NO:8. In still another embodiment, the antibody comprises an amino acid sequence shown in SEQ ID NO:10.

In another embodiment, the invention pertains to a method of downmodulating the immune response comprising contacting a cell with an antibody-toxic moiety conjugate, wherein the antibody specifically recognizes CTLA4.

BRIEF DESCRIPTION OF THE DRAWINGS

FIG. 1A shows antibodies 25, 26, and 27. FIG. 1B shows antibodies 29, 33, and 34. FIG. 1C shows antibodies 35, 36, and 38.

FIG. 1D shows antibodies 25, 26, and 27. FIG. 1E shows antibodies 29, 33, and 34. FIG. 1F shows antibodies 35, 36, and 38. Antibody number 29 and 33 fail to block binding of CTLA4 to CD86.

FIG. 1G shows antibodies 25, 26, and 27. FIG. 1H shows antibodies 29, 33, and 34. FIG. 1I shows antibodies 35, 36, and 38. Antibody number 29 and 33 fail to block binding of CTLA4 to CD80.

FIGS. 4A–4B illustrate the effect of soluble forms of anti-CTLA4 antibody on T cell proliferation and cytokine production. Antibody number 26 enhances the proliferation of primary T cells in a mixed lymphocyte reaction (MLR) (FIG. 4A). The effect of various anti-CTLA4 antibodies on IL-2 production by Jurkat cells is shown in FIG. 4B.

FIG. 5 illustrates that the murine form of anti-CTLA4 antibody number 26 and the IgG1, IgG4, and IgG2m3 humanized forms of antibody 26 (hCTLA4-26B) bind to CTLA4 with similar affinity. Data are from an ELISA competition assay against cold CTLA4-26B antibody.

FIG. 9 shows the cDNA (SEQ ID NO:7) and deduced amino acid sequence (SEQ ID NO:8) of the light chain of humanized anti-CTLA4. The amino acids are shown in single letter code. The CDRs are underlined in blue, mouse residues retained for structural integrity are the underlined single amino acid residues, and the double-underlined single amino acid residues represent consensus amino acid found at this position in the selected set of known human variable sequences.

FIG. 10 shows the cDNA (SEQ ID NO:9) and deduced amino acid sequence (SEQ ID NO:10) of the heavy chain of humanized anti-CTLA4. The amino acids are shown in single letter code. The CDRs are underlined in blue, mouse residues retained for structural integrity are the underlined single amino acid residues, and double-underlined single amino acid residues represent consensus amino acid found at this position in the selected set of known human variable sequences.

FIG. 11 shows the effect of increasing concentrations of a humanized anti-CTLA4 antibody (Hu-26B) or a murine anti-CTLA4 antibody (Mu-26B) on T cell responses, as measured by IL-2 production by Jurkat CTLA4+ cells.

DETAILED DESCRIPTION OF THE INVENTION

Figure 1A:
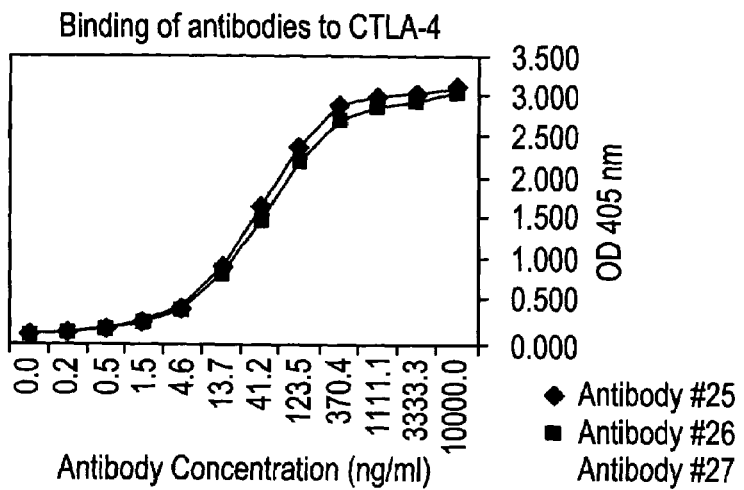
FIGS. 1A–1C illustrate the binding of the various antibodies to CTLA4.

As set forth briefly above, the instant invention pertains, at least in part, to the identification and characterization of anti-CTLA4 antibodies, as well as conjugated forms of these or other anti-CTLA4 antibodies, and to methods of using such antibodies to modulate the immune response.

Various aspects of the invention are described in further detail in the following subsections:

I. Definitions

As used herein, the term "T cell" includes CD4+ T cells and CD8+ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

As used herein, the term "immune response" includes T cell mediated and/or B cell mediated immune responses that are influenced by modulation of T cell costimulation. Exemplary immune responses include T cell responses, e.g., proliferation, cytokine production, and cellular cytotoxicity. In addition, the term immune response includes immune responses that are indirectly effected by T cell activation, e.g., antibody production (humoral responses) and activation of cytokine responsive cells, e.g., macrophages.

As used herein, the term "costimulatory receptor" includes receptors which transmit a costimulatory signal to a immune cell, e.g., CD28. As used herein, the term "inhibitory receptors" includes receptors which transmit a negative signal to an immune cell (e.g., CTLA4). An inhibitory signal as transduced by an inhibitory receptor can occur even if a costimulatory receptor (such as CD28) is not present on the immune cell and, thus, is not simply a function of competition between inhibitory receptors and costimulatory receptors for binding of costimulatory molecules (Fallarino et al. (1998) *J. Exp. Med.* 188:205). Transmission of an inhibitory signal to an immune cell can result in unresponsiveness or anergy or programmed cell death in the immune cell.

Depending upon the form of the molecule that binds to a cell surface receptor, either a signal can be transmitted to the cell (e.g., by a multivalent form of a costimulatory molecule or a crosslinked form of an antibody that results in crosslinking of receptor) or a signal can be inhibited in the cell (e.g., by a soluble, monovalent form of a costimulatory molecule or antibody), e.g., by competing with activating forms of costimulatory molecules for binding to the receptor. However, there are instances in which a soluble molecule can be stimulatory e.g., a soluble form of an antibody that blocks the binding of an inhibitory receptor to a costimulatory molecule and blocks the transmission of negative signal. The effects of the various modulatory agents can be easily demonstrated using routine screening assays as described herein.

As used herein, the term "costimulate" with reference to activated T cells includes the ability of a costimulatory molecule to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor (e.g., by an antigen or by a polyclonal activator) are referred to herein as "activated T cells."

As used herein, the term "activating receptor" includes immune cell receptors that bind antigen, complexed antigen (e.g., in the context of MHC molecules), or bind to antibodies. Such activating receptors include T cell receptors (TCR), B cell receptors (BCR), cytokine receptors, LPS receptors, complement receptors, and Fc receptors.

For example, T cell receptors are present on T cells and are associated with CD3 molecules. T cell receptors are stimulated by antigen in the context of MHC molecules (as well as by polyclonal T cell activating reagents). T cell activation via the TCR results in numerous changes, e.g., protein phosphorylation, membrane lipid changes, ion fluxes, cyclic nucleotide alterations, RNA transcription changes, protein synthesis changes, and cell volume changes, and expression of activation markers, e.g., CTLA4.

Transmission of a costimulatory signal to a T cell involves a signaling pathway that is not inhibited by cyclosporin A. In addition, a costimulatory signal can induce cytokine secretion (e.g., IL-2 and/or IL-10) in a T cell and/or can prevent the induction of unresponsiveness to antigen, the induction of anergy, or the induction of cell death in the T cell.

As used herein, the term "inhibitory signal" refers to a signal transmitted via an inhibitory receptor (e.g., CTLA4) on an immune cell. Such a signal antagonizes a signal transmitted via an activating receptor (e.g., via a TCR) and can result, e.g., in: inhibition of second messenger generation; inhibition of proliferation; inhibition of effector function in the immune cell, (e.g., reduced cellular cytotoxicity) the failure of the immune cell to produce mediators, (such as cytokines (e.g., IL-2) and/or mediators of allergic responses); or the development of anergy.

As used herein, the term "unresponsiveness" includes refractivity of immune cells to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory molecule) results in failure to produce cytokines and, thus, failure to proliferate. Anergic T cells can, however, mount responses to unrelated antigens and can proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

As used herein, the term "activity" with respect to a polypeptide includes activities which are inherent in the structure of a polypeptide. With respect to CTLA4, the term "activity" includes the ability of a CTLA4 polypeptide to bind to a costimulatory molecule and/or to modulate an inhibitory signal in an activated immune cell, e.g., by engaging a natural ligand on an antigen presenting cell. CTLA4 transmits an inhibitory signal to a T cell. Modulation of an inhibitory signal in a T cell results in modulation of proliferation of and/or cytokine secretion by the T cell. CTLA4 can also modulate a costimulatory signal by competing with a costimulatory receptor for binding of costimulatory molecules, e.g., CTLA4. Thus, the term "CTLA4 activity" includes the ability of a CTLA4 polypeptide to bind its natural ligand(s), the ability to modulate immune cell costimulatory or inhibitory signals, and the ability to modulate the immune response.

The term "antibody", as used herein, is intended to refer to immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The phrase "complementary determining region" (CDR) includes the region of an antibody molecule which comprises the antigen binding site.

Antibodies may be an IgG antibodies such as IgG1, IgG2, IgG3 or IgG4; or IgM, IgA, IgE or IgD isotype. The constant domain of the antibody heavy chain may be selected depending upon the effector function desired. The light chain constant domain may be a kappa or lambda constant domain.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., hCTLA4). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544–546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423–426; and Huston et al. (1988) *Proc. Natl. Acad. Sci. USA* 85:5879–5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444–6448; Poljak, R. J., et al. (1994) *Structure* 2:1121–1123).

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93–101) and use of a cysteine residue, a marker peptide and a C-terminal polyhistidine tag to make bivalent and biotinylated scFv molecules (Kipriyanov, S. M., et al. (1994) *Mol. Immunol.* 31:1047–1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

Antibodies may be polyclonal or monoclonal; xenogeneic, allogeneic, or syngeneic; or modified forms thereof, e.g., humanized, chimeric, etc. Preferably, antibodies of the invention bind specifically or substantially specifically to CTLA4 molecules. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody composition, typically displays a single binding affinity for a particular antigen with which it immunoreacts.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

An "isolated antibody", as used herein, is intended to refer to an antibody that is substantially free of other antibodies having different antigenic specificities (e.g., an isolated antibody that specifically binds CTLA4 is substantially free of antibodies that specifically bind antigens other than CTLA4). Moreover, an isolated antibody may be substantially free of other cellular material and/or chemicals.

"CTLA4 blocking antibodies" are antibodies that specifically bind to the extracellular domain of CTLA4 protein, and block the binding of CTLA4 to its counter-receptors, e.g., CD80, CD86, etc. CTLA4 blocking antibodies can bind to a site of CTLA4 at a site in spatial proximity to the site of CTLA4 binding to a costimulatory molecule, e.g., close enough to the site of costimulatory binding to sterically interfere with binding of CTLA4 to the costimulatory molecule. Such blocking antibodies block the transmission of an inhibitory signal via CTLA4 and, thus, in soluble form, function to enhance T cell proliferation. "CTLA4 activating antibodies" are antibodies that specifically bind to the extracellular domain of the CTLA4 protein at a site in the extracellular domain of CTLA4 and which transmit a negative signal via CTLA4 in multivalent form. These activating antibodies do not block the binding of CTLA4 to its counter-receptors, e.g., CD80 or CD86. Such antibodies, upon binding to CTLA4, result in the transmission of an inhibitory signal via CTLA4 and, thus, result in a decrease in T cell proliferation. Both CTLA4 blocking and activating antibodies transmit a negative signal via CTLA4 when they are in multivalent form (e.g., cross-linked).

The phrase "specifically" with reference to binding, recognition, or reactivity of antibodies includes antibodies which bind to naturally occurring molecules which are expressed transiently only on activated T cells. Specifically, with respect to CTLA4, the term "specifically" with reference to binding, recognition, or reactivity of antibodies includes anti-CTLA4 antibodies that bind to naturally occurring forms of CTLA4, but are substantially unreactive with molecules related to CTLA4, such as CD28 and other members of the immunoglobulin superfamily. The phrase "substantially unreactive" includes antibodies which display no greater binding to molecules related to CTLA4, e.g., CD28 (but excluding CTLA4) as compared to unrelated molecules, e.g., CD27. Preferably, such antibodies bind to molecules related to CTLA4 (but excluding CTLA4) with only background binding. Antibodies specific for CTLA4 from one source, e.g., human CTLA4 may or may not be reactive with CTLA4 molecules from different species. Antibodies specific for naturally occurring CTLA4 may or may not bind to mutant forms of such molecules. In one embodiment, mutations in the amino acid sequence of a naturally occurring CTLA4 molecule result in modulation of the binding (e.g., either increased or decreased binding) of the antibody to the CTLA4 molecule. Antibodies to CTLA4 can be readily screened for their ability to meet this criteria. Assays to determine affinity and specificity of binding are known in the art, including competitive and non-competitive assays. Assays of interest include ELISA, RIA, flow cytometry, etc. Binding assays may use purified or semi-purified CTLA4 protein, or alternatively may use cells that express CTLA4, e.g., cells transfected with an expression construct for CTLA4; T cells that have been stimulated through cross-linking of CD3 and CD28; the addition of irradiated allogeneic cells, etc. As an example of a binding assay, purified CTLA4 protein is bound to an insoluble support, e.g., microtiter plate, magnetic beads, etc. The candidate antibody and soluble, labeled CD80 or CD86 are added to the cells, and the unbound components are then washed off. The ability of the antibody to compete with CD80 and CD86 for CTLA4 binding is determined by quantitation of bound, labeled CD80 or CD86. Confirmation that the blocking agent does not cross-react with CD28 may be performed with a similar assay, substituting CD28 for CTLA4. An isolated antibody that specifically binds human CTLA4 may, however, have cross-reactivity to other antigens, such as CTLA4 molecules from other species.

As used herein, the terms "toxin" and "toxic moiety" include naturally occurring (as well as derivatized or chemically modified forms thereof) or synthetic molecules or moieties that are proteinaceous or non-proteinaceous and that are toxic to cells, e.g., eukaryotic cells. "Toxic moieties" include, e.g., portions of naturally occurring toxins that retain the property of toxicity (such as toxic moieties (e.g., A chains) of bipartate toxins). The term "toxic moiety" also includes antibiotic molecules or other agents (e.g. chemotherapeutic agents) that have cellular cytotoxic effects. Toxic moieties bring about the death of cells by any of a variety of mechanisms, e.g., by acting on cellular machinery after internalization into the cell or by forming holes in cellular membranes. Exemplary toxic moieties are described in more detail herein. Antibody-toxic moiety conjugates of the invention include antibodies or antibody binding portions thereof that are conjugated to toxic moiety molecules to specifically deliver those toxic moiety molecules to the cells to which the antibody or fragment thereof binds.

As used herein, a "naturally-occurring" nucleic acid molecule refers to an RNA or DNA molecule having a nucleotide sequence that occurs in nature (e.g., encodes a natural protein).

As used herein, the term "coding region" refers to regions of a nucleotide sequence comprising codons which are translated into amino acid residues, whereas the term "non-coding region" refers to regions of a nucleotide sequence that are not translated into amino acids (e.g., 5' and 3' untranslated regions).

As used herein, the term "vector" refers to a nucleic acid molecule capable of transporting another nucleic acid molecule to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g, bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a nucleic acid molecule of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, an "isolated protein" refers to a protein that is substantially free of other proteins, cellular material and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the CTLA4 protein is derived, or substantially free from chemical precursors or other chemicals when chemically synthesized. The language "substantially free of cellular material" includes preparations of CTLA4 protein in which the protein is separated from cellular components of the cells from which it is isolated or recombinantly produced. In one embodiment, the language "substantially free of cellular material" includes preparations of CTLA4 protein having less than about 30% (by dry weight) of non-CTLA4 protein (also referred to herein as a "contaminating protein"), more preferably less than about 20% of non-CTLA4 protein, still more preferably less than about 10% of non-CTLA4 protein, and most preferably less than about 5% non-CTLA4 protein. When the CTLA4 protein or biologically active portion thereof is recombinantly produced, it is also preferably substantially free of culture medium, i e., culture medium represents less than about 20%, more preferably less than about 10%, and most preferably less than about 5% of the volume of the protein preparation.

The language "substantially free of chemical precursors or other chemicals" includes preparations of CTLA4 protein in which the protein is separated from chemical precursors or other chemicals which are involved in the synthesis of the protein. In one embodiment, the language "substantially free of chemical precursors or other chemicals" includes preparations of CTLA4 protein having less than about 30% (by dry weight) of chemical precursors or non-CTLA4 chemicals, more preferably less than about 20% chemical precursors or non-CTLA4 chemicals, still more preferably less than about 10% chemical precursors or non-CTLA4 chemicals, and most preferably less than about 5% chemical precursors or non-CTLA4 chemicals.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid molecule and the amino acid sequence encoded by that nucleic acid molecule, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA molecule coding for a CTLA4 polypeptide or CTLA4 antibody of the invention (or any portion thereof) can be used to derive the CTLA4 polypeptide or CTLA4 antibody amino acid sequence, using the genetic code to translate the CTLA4 polypeptide or CTLA4 antibody molecule into an amino acid sequence. Likewise, for any CTLA4 polypeptide or CTLA4 antibody-amino acid sequence, corresponding nucleotide sequences that can encode CTLA4 polypeptide or CTLA4 antibody protein can be deduced from the genetic code (which, because of its redundancy, will produce multiple nucleic acid sequences for any given amino acid sequence). Thus, description and/or disclosure herein of a CTLA4 polypeptide or CTLA4 antibody nucleotide sequence should be considered to also include description and/or disclosure of the amino acid sequence encoded by the nucleotide sequence. Similarly, description and/or disclosure of a CTLA4 polypeptide or CTLA4 antibody amino acid sequence herein should be considered to also include description and/or disclosure of all possible nucleotide sequences that can encode the amino acid sequence.

II. CTLA4 Immunogens

One aspect of the invention pertains to anti-CTLA4 antibodies. Antibodies to CTLA4 can be made by immunizing a subject (e.g., a mammal) with a CTLA4 polypeptide or a nucleic acid molecule encoding a CTLA4 polypeptide or a portion thereof. In one embodiment, native CTLA4 proteins, or immunogenic portions thereof, can be isolated from cells or tissue sources by an appropriate purification scheme using standard protein purification techniques. In another embodiment, CTLA4 proteins, or immunogenic portions thereof, can be produced by recombinant DNA techniques. Alternative to recombinant expression, a CTLA4 protein or immunogenic portion thereof, can be synthesized chemically using standard peptide synthesis techniques. Alternatively, nucleic acid molecules encoding a CTLA4 molecule or portion thereof can be used as immunogens. Whole cells expressing CTLA4 can be used as immunogens to produce anti-CTLA4 antibodies. For example, cells can be made to express CTLA4 by transfection with an cDNA or by utilizing a phospholipid anchor domain.

The origin of the immunogen may be mouse, human, rat, monkey etc. The host animal will generally be a different species than the immunogen, e.g., mouse CTLA4 used to immunize hamsters, human CTLA4 to immunize mice, etc. The human and mouse CTLA4 contain highly conserved stretches in the extracellular domain (Harper et al. (1991) *J. Immunol.* 147:1037–1044). Peptides derived from such highly conserved regions may be used as immunogens to generate cross-specific antibodies. The nucleotide and amino acid sequences of CTLA4 from a variety of sources are known in the art. For example, the nucleotide and amino acid sequences of human CTLA4 can be found in Dariavach et al. (1988) *Eur. J. Immunol.* 18:1901; Linsley et al. *J. Exp. Med.* 174:561; or Metzler et al. (1997) *Nat. Struct. Biol.* 4:525; or Harper et al. (1991) *J. Immunol.* 147:1037 or can be accessed on any of a variety of public or private databases, e.g., GenBank. Nucleotide and amino acid sequences encoding human CTLA4 molecules are presented in SEQ ID NO:1 and 2, respectively.

In one embodiment, the immunogen may comprise the complete protein, or fragments and derivatives thereof. Preferred immunogens comprise all or a part of the extracellular domain of human CTLA4 (e.g., about amino acid residues 36–161 or about amino acids 38–161 of SEQ ID NO:2), where these residues contain the post-translation modifications, such as glycosylation, found on the native CTLA4. Immunogens comprising the extracellular domain are produced in a variety of ways known in the art, e.g., expression of cloned genes using conventional recombinant methods, isolation from T cells, sorted cell populations expressing high levels of CTLA4, etc. In another embodiment, the immunogen may comprise DNA encoding a CTLA4 molecule or a portion thereof. For example, as set forth in the appended examples, 2 µg cDNA encoding the extracellular domain of recombinant human CTLA4 could be used as an immunogen.

In a preferred embodiment, the immunogen is a human CTLA4 molecule. Preferably, CTLA4 proteins comprise the amino acid sequence encoded by SEQ ID NO:1 or fragment thereof. In another preferred embodiment, the protein comprises the amino acid sequence of SEQ ID NO:2 or fragment thereof. For example, the CTLA4 molecule can differ in amino acid sequence from that shown in SEQ ID NO:2, e.g., can be from a different source or can be modified to increase its immunogenicity. In one embodiment, the protein has at least about 80%, and even more preferably, at least about 90% or 95% amino acid identity with the amino acid sequence shown in SEQ ID NO:2.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The residues at corresponding positions are then compared and when a position in one sequence is occupied by the same residue as the corresponding position in the other sequence, then the molecules are identical at that position. The percent identity between two sequences, therefore, is a function of the number of identical positions shared by two sequences (i.e., % identity=# of identical positions/ total # of positions×100). The percent identity between the two sequences is a function of the number of identical positions shared by the sequences, taking into account the number of gaps, and the length of each gap, which need to be introduced for optimal alignment of the two sequences. As used herein amino acid or nucleic acid "identity" is equivalent to amino acid or nucleic acid "homology".

The comparison of sequences and determination of percent identity between two sequences can be accomplished using a mathematical algorithm. In a preferred embodiment, the percent identity between two amino acid sequences is determined using the GAP program in the GCG software package (available from Accelrys, San Diego, Calif.), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available from Accelrys, San Diego, Calif.), using a NWSgapdna.CMP matrix and a gap weight of 40, 50, 60, 70, or 80 and a length weight of 1, 2, 3, 4, 5, or 6.

The nucleic acid and protein sequences of the CTLA4 can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215: 403–10. BLAST nucleotide searches can be performed with the NBLAST program, score=100, wordlength=12 to obtain nucleotide sequences homologous to CTLA4 nucleic acid molecules of the invention. BLAST protein searches can be performed with the XBLAST program, score=50, wordlength=3 to obtain amino acid sequences homologous to CTLA4 protein molecules of the invention. To obtain gapped alignment for comparison purposes, Gapped BLAST can be utilized as described in Altschul et al., (1997) Nucleic Acids Res. 25(17):3389–3402. When utilizing BLAST and Gapped BLAST programs, the default parameters of the respective programs (e.g., XBLAST and NBLAST) can be used. For example, the nucleotide sequences of the invention were analyzed using the default Blastn matrix 1–3 with gap penalties set at: existence 11 and extension 1. The amino acid sequences of the invention were analyzed using the default settings: the Blosum62 matrix with gap penalties set at existence 11 and extension 1. More information on these programs is available from the NCBI, Bethesda, Md.

CTLA4 chimeric or fusion proteins or nucleic acid molecules encoding them can also be used as immunogens. As used herein, a CTLA4 "chimeric protein" or "fusion protein" comprises a CTLA4 polypeptide operatively linked to a non-CTLA4 polypeptide. A "CTLA4 polypeptide" refers to a polypeptide having an amino acid sequence corresponding to CTLA4 polypeptide, whereas a "non-CTLA4 polypeptide" refers to a polypeptide having an amino acid sequence corresponding to a protein which is not substantially homologous to the CTLA4 protein, e.g., a protein which is different from the CTLA4 protein and which is derived from the same or a different organism. Within a CTLA4 fusion protein the CTLA4 polypeptide can correspond to all or a portion of a CTLA4 protein. In a preferred embodiment, a CTLA4 fusion protein comprises at least one biologically active portion of a CTLA4 protein, e.g., an extracellular domain of a CTLA4 protein. Within the fusion protein, the term "operatively linked" is intended to indicate that the CTLA4 polypeptide and the non-CTLA4 polypeptide are fused in-frame to each other. The non-CTLA4 polypeptide can be fused to the N-terminus or C-terminus of the CTLA4 polypeptide.

Preferably, a CTLA4 fusion protein or nucleic acid molecule encoding a CTLA4 fusion protein is produced by standard recombinant DNA techniques. For example, DNA fragments coding for the different polypeptide sequences are ligated together in-frame in accordance with conventional techniques, for example employing blunt-ended or staggerended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide or an HA epitope tag). A CTLA4 encoding nucleic acid can be cloned into such an expression vector such that the fusion moiety is linked in-frame to the CTLA4 protein. Such fusion moieties can be linked to the C or to the N terminus of the CTLA4 protein or a portion thereof.

Variants of the CTLA4 proteins can also be generated by mutagenesis, e.g., discrete point mutation or truncation of a CTLA4 protein and used as a immunogen. In one embodiment, variants of a CTLA4 protein can be identified by screening combinatorial libraries of mutants, e.g., truncation mutants, of a CTLA4 protein for CTLA4 protein agonist or antagonist activity. In one embodiment, a variegated library of CTLA4 variants is generated by combinatorial mutagenesis at the nucleic acid level and is encoded by a variegated gene library. A variegated library of CTLA4 variants can be produced by, for example, enzymatically ligating a mixture of synthetic oligonucleotides into gene sequences such that a degenerate set of potential CTLA4 sequences is expressible as individual polypeptides, or alternatively, as a set of larger fusion proteins (e.g., for phage display) containing the set of CTLA4 sequences therein. There are a variety of methods which can be used to produce libraries of potential CTLA4 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential CTLA4 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a CTLA4 protein coding sequence can be used to generate a variegated population of CTLA4 fragments for screening and subsequent selection of variants of a CTLA4 protein. In one embodiment, a library of coding sequence fragments can be generated by treating a double stranded PCR fragment of a CTLA4 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the CTLA4 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of CTLA4 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify CTLA4 variants (Arkin and Youvan (1992) *Proc. Natl. Acad. Sci. USA* 89:7811–7815; Delagrave et al. (1993) *Protein Engineering* 6(3):327–331).

In one embodiment, cell based assays can be exploited to analyze a variegated CTLA4 library. For example, a library of expression vectors can be transfected into a cell line which ordinarily synthesizes and secretes CTLA4. The transfected cells are then cultured such that CTLA4 and a particular mutant CTLA4 are secreted and the effect of expression of the mutant on CTLA4 activity in cell supernatants can be detected, e.g., by any of a number of enzymatic assays. Plasmid DNA can then be recovered from the cells which score for inhibition, or alternatively, potentiation of CTLA4 activity, and the individual clones further characterized.

An isolated CTLA4 protein, or a portion or fragment thereof, or nucleic acid molecules encoding a CTLA4 polypeptide of portion thereof, can be used as an immunogen to generate antibodies that bind CTLA4 using standard techniques for polyclonal and monoclonal antibody preparation. In one embodiment, a full-length CTLA4 protein or nucleic acid molecule encoding a full-length CTLA4 protein can be used. Alternatively, an antigenic peptide fragment (i.e., a fragment capable of promoting an antigenic response) of a CTLA4 polypeptide or nucleic acid molecule encoding a fragment of a CTLA4 polypeptide can be used can be used as the immunogen. An antigenic peptide fragment of a CTLA4 polypeptide typically comprises at least 8 amino acid residues (e.g., at least 8 amino acid residues of the amino acid sequence shown in SEQ ID NO:2) and encompasses an epitope of a CTLA4 polypeptide such that an antibody raised against the peptide forms an immune complex with a CTLA4 molecule. Preferred epitopes encompassed by the antigenic peptide are regions of CTLA4 that are located on the surface of the protein, e.g., hydrophilic regions. In another embodiment, an antibody binds specifically to a CTLA4 polypeptide. In a preferred embodiment, the CTLA4 polypeptide is a human CTLA4 polypeptide.

Preferably, the antigenic peptide comprises at least about 10 amino acid residues, more preferably at least about 15 amino acid residues, even more preferably at least 20 about amino acid residues, and most preferably at least about 30 amino acid residues. Preferred epitopes encompassed by the antigenic peptide are regions of a CTLA4 polypeptide that are located on the surface of the protein, e.g., hydrophilic regions, and that are unique to a CTLA4 polypeptide. In one embodiment such epitopes can be specific for a CTLA4 proteins from one species, such as mouse or human (i.e., an antigenic peptide that spans a region of a CTLA4 polypeptide that is not conserved across species is used as immunogen; such non conserved residues can be determined using an amino acid sequence, e.g., using one of the programs described supra). A standard hydrophobicity analysis of the CTLA4 protein can be performed to identify hydrophilic regions.

A CTLA4 immunogen typically is used to prepare antibodies by immunizing a suitable subject, (e.g., rabbit, goat, mouse or other mammal) with the immunogen. An appropriate immunogenic preparation can contain, for example, a nucleic acid molecule encoding a CTLA4 immunogen, a recombinantly expressed CTLA4 protein or a chemically synthesized CTLA4 immunogen. The preparation can further include an adjuvant, such as Freund's complete or incomplete adjuvant, alum, a cytokine or cytokines, or similar immunostimulatory agent. Immunization of a suitable subject with an immunogenic CTLA4 preparation induces a polyclonal anti-CTLA4 antibody response.

III. Anti-CTLA4 Antibodies

Another aspect of the invention pertains to anti-CTLA4 antibodies. Antibodies typically comprise two heavy chains linked together by disulfide bonds and two light chains. Each light chain is linked to a respective heavy chain by disulfide bonds. Each heavy chain has at one end a variable domain followed by a number of constant domains. Each light chain has a variable domain at one end and a constant domain at its other end. The light chain variable domain is aligned with the variable domain of the heavy chain. The light chain constant domain is aligned with the first constant domain of the heavy chain. The constant domains in the light and heavy chains are not involved directly in binding the antibody to antigen. The variable domains of each pair of light and heavy chains form the antigen binding site.

The domains on the light and heavy chains have the same general structure and each domain comprises a framework of four regions, whose sequences are relatively conserved, connected by three complementarity determining regions (CDRs). The four framework regions largely adopt a beta-sheet conformation and the CDRs form loops connecting, and in some cases forming part of, the beta-sheet structure. The CDRs are held in close proximity by the framework regions and, with the CDRs from the other domain, contribute to the formation of the antigen binding site. CDRs and framework regions of antibodies may be determined by reference to Kabat et al ("Sequences of proteins of immunological interest" US Dept. of Health and Human Services, US Government Printing Office, 1987).

Polyclonal anti-CTLA4 antibodies can be prepared as described above by immunizing a suitable subject with a CTLA4 immunogen. The anti-CTLA4 antibody titer in the immunized subject can be monitored over time by standard techniques, such as with an enzyme linked immunosorbent assay (ELISA) using immobilized a CTLA4 polypeptide. If desired, the antibody molecules directed against a CTLA4 polypeptide can be isolated from the mammal (e.g., from the blood) and further purified by well known techniques, such as protein A chromatography to obtain the IgG fraction. At an appropriate time after immunization, e.g., when the anti-CTLA4 antibody titers are highest, antibody-producing cells can be obtained from the subject and used to prepare monoclonal antibodies by standard techniques, such as the hybridoma technique originally described by Kohler and Milstein (1975, *Nature* 256:495–497) (see also, Brown et al. (1981) *J. Immunol.* 127:539–46; Brown et al. (1980) *J Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lemer (1981) *Yale J. Biol. Med.*, 54:387–402; M. L. Gefter et al. (1977) *Somatic Cell Genet.*, 3:231–36). Briefly, an immortal cell line (typically a myeloma) is fused to lymphocytes (typically splenocytes) from a mammal immunized with a CTLA4 immunogen as described above, and the culture supernatants of the resulting hybridoma cells are screened to identify a hybridoma producing a monoclonal antibody that binds specifically to a CTLA4 polypeptide.

Any of the many well known protocols used for fusing lymphocytes and immortalized cell lines can be applied for the purpose of generating an anti-CTLA4 monoclonal antibody (see, e.g., G. Galfre et al. (1977) *Nature* 266:55052; Gefter et al. *Somatic Cell Genet.*, cited supra; Lemer, *Yale J. Biol. Med.*, cited supra; Kenneth, *Monoclonal Antibodies*, cited supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a CTLA4 molecule, e.g., using a standard ELISA assay.

Anti-CTLA4 antibodies may bind to any portion of the CTLA4 molecule. Preferably, anti-CTLA4 antibodies bind to the extracellular domain of the CTLA4 molecule. Preferred antibodies bind to the CTLA4 molecule at a site in spatial proximity to the site of CD80/CD86 binding. In one embodiment, anti-CTLA4 antibodies are affected by the substitution of the glutamic acid residue at position 46 of the CTLA4 molecule. In another embodiment, preferred antibodies are affected by the substitution of the arginine at position 85 of the CTLA4 molecule.

Preferred antibodies are anti-human CTLA4 monoclonal antibody numbers 25, 26, 27, 29, 33, 34, 35, 36, or 38 described herein. These antibodies were determined to be of the IgG1 isotype. The preparation and characterization of these antibodies is described in detail in the appended examples.

A particularly preferred anti-human CTLA4 antibody is antibody 26, which is described in detail in the appended examples and which blocks binding to CD80/CD86 and, thus, results in blocking the transmission of a negative signal via CTLA4. The amino acid sequences of the VH and VK regions of antibody 26 are set forth in Example 6. The amino acid sequences of a humanized version of antibody 26 are provided in Example 7.

As an alternative to preparing monoclonal antibody-secreting hybridomas, a monoclonal anti-CTLA4 antibody can be identified and isolated by screening a recombinant combinatorial immunoglobulin library (e.g., an antibody phage display library) with CTLA4 to thereby isolate immunoglobulin library members that bind a CTLA4 polypeptide. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al.

International Publication No. WO 90/02809; McCafferty et al. U.S. Pat. No. 6,172,197; Johnson et al. U.S. Pat. No. 6,140,471; Jespers et al. U.S. Pat. No. 6,017,732; Griffiths et al. U.S. Pat. No. 6,010,884; McCafferty et al. U.S. Pat. No. 5,969,108; Griffiths et al. U.S. Pat. No. 5,962,255; Griffiths et al. U.S. Pat. No. 5,885,793; Borrebaeck et al. U.S. Pat. No. 6,027,930; Borrebaeck et al. U.S. Pat. No. 5,712,089; Fuchs et al. (1991) *Biotechnology* (NY) 9:1369–1372; Jespers et al. (1994) *Biotechnology* (NY) 12:899–903; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrard et al. (1991) *Biotechnology* (NY) 9:1373–1377; Hoogenboom et al. (1991) *Nucleic Acids Res.* 19:4133–4137; Barbas et al. (1991) *Proc. Natl. Acad. Sci. USA* 88:7978–7982; and McCafferty et al. (1990) *Nature* 348:552–554.

Antibody fragments, such as Fv, F(ab')2 and Fab may be prepared by cleavage of the intact protein, e.g., by protease or chemical cleavage. Alternatively, a truncated gene is designed. For example, a chimeric gene encoding a portion of the F(ab')2 fragment would include DNA sequences encoding the CH1 domain and hinge region of the H chain, followed by a translational stop codon to yield the truncated molecule. For example, consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

The antibody may be produced as a single chain, instead of the normal multimeric structure. Single chain antibodies are described in Jost et al. (1994) *J. Biol. Chem.* 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

For in vivo use, particularly for injection into humans, it is desirable to decrease the antigenicity of the blocking agent. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *Proc. Natl. Acad. Sci. USA.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of Immunological Interest, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Chimeric and humanized monoclonal antibodies can be produced by recombinant DNA techniques known in the art, for example using methods described in Robinson et al. International Patent Publication PCT/US86/02269; Akira, et al. European Patent Application 184,187; Taniguchi, M., European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Hardman et al. U.S. Pat. No. 5,843,708; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Bendig, M. M. et al. (1995) "Rodent to human antibodies by CDR-grafting," in *Antibody Engineering: A Practical Approach*, eds. Chiswell, D. J., McCafferty, J. and Hoogenboom, H. IRL Press, Oxford. p147; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *Biotechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060. In addition, humanized antibodies can be made according to standard protocols such as those disclosed in U.S. Pat. Nos. 5,777,085; 5,530,101; 5,693,762; 5,693,761; 5,882,644; 5,834,597; 5,932,448; and 5,565,332.

Fully human anti-CTLA4 antibodies may also be made by immunizing animals (e.g., mice) transgenic for human immunoglobulin genes using the methods of Lonberg and Huszar (1995) *Int. Rev. Immunol.* 13:65–93; Lonberg et al. U.S. Pat. Nos. 5,877,397, 5,874,299, 5,814,318, 5,789,650, 5,770,429, 5,661,016, 5,633,425, 5,625,126, 5,569,825, and 5,545,806; and Kucherlapati et al. U.S. Pat. Nos. 6,162,963, 6,150,584, 6,114,598, and 6,075,181.

For example, an antibody may be humanized by grafting the desired CDRs onto a human framework, e.g., according to EP-A-0239400. A DNA sequence encoding the desired reshaped antibody can therefore be made beginning with the human DNA whose CDRs it is wished to reshape. The rodent variable domain amino acid sequence containing the desired CDRs is compared to that of the chosen human antibody variable domain sequence. The residues in the human variable domain are marked that need to be changed to the corresponding residue in the rodent to make the human variable region incorporate the rodent CDRs. There may also be residues that need substituting, e.g., adding to or deleting from the human sequence. Oligonucleotides can be synthesized that can be used to mutagenize the human variable domain framework to contain the desired residues. Those oligonucleotides can be of any convenient size.

Alternatively, humanization may be achieved using the recombinant polymerase chain reaction (PCR) methodology of WO 92/07075. Using this methodology, a CDR may be spliced between the framework regions of a human antibody. In general, the technique of WO 92/07075 can be performed using a template comprising two human framework regions, AB and CD, and between them, the CDR which is to be replaced by a donor CDR. Primers A and B are used to amplify the framework region AB, and primers C and D used to amplify the framework region CD. However, the primers B and C each also contain, at their 5' ends, an additional sequence corresponding to all or at least part of the donor CDR sequence. Primers B and C overlap by a length sufficient to permit annealing of their 5' ends to each other under conditions which allow a PCR to be performed. Thus, the amplified regions AB and CD may undergo gene splicing by overlap extension to produce the humanized product in a single reaction.

In one method, humanized anti-CTLA4 antibodies can be made by joining polynucleotides encoding portions of immunoglobulins capable of binding CTLA4 to polynucleotides encoding appropriate human framework regions. Exemplary humanization methods can be found, e.g., in Queen et al. (1989) *Proc. Natl. Acad. Sci. USA* 86:10029 or U.S. Pat. Nos. 5,585,089, 5,693,762, 5,693,761, or 5,530,101, the teachings of which are incorporated herein in their entirety. To select the human framework region, a framework or variable region amino acid sequence of a CDR-providing non-human immunoglobulin is compared with corresponding sequences in a human immunoglobulin sequence collection, and a sequence having high homology is selected. A principle behind the selection is that as acceptor, a framework is used from a particular human immunoglobulin that is unusually homologous to the donor immunoglobulin to be humanized, or to use a consensus framework from many human antibodies. For example, comparison of the sequence of a mouse heavy (or light) chain variable region against human heavy (or light) variable regions in a data bank (for example, the National Biomedical Research Foundation Protein Identification Resource) shows that the extent of homology to different human regions varies greatly, typically from about 40% to about 60–70%. By choosing immunoglobulin one of the human heavy (respectively light) chain variable regions that is most homologous to the heavy (respectively light) chain variable region of the donor immunoglobulin as the acceptor, fewer amino acids will need to be changed in going from the donor immunoglobulin to the humanized immunoglobulin. Thus, there is a smaller chance of changing an amino acid near the CDRs that distorts their conformation. Moreover, the precise overall shape of a humanized antibody comprising the humanized immunoglobulin chain may more closely resemble the shape of the donor antibody, also reducing the chance of distorting the CDRs. Due to codon degeneracy and non-critical amino-acid substitutions, other polynucleotide sequences can be readily substituted for those sequences, as detailed below.

In making a humanized antibody amino acids in the human Ig to be used (human acceptor sequence) can be replaced by the corresponding amino acids from the non-human starting Ig (donor sequence) if they are in a CDR.

In another embodiment of the present invention, either in conjunction with the above step or separately, additional amino acids in the acceptor immunoglobulin chain may be replaced with amino acids from the CDR-donor immunoglobulin chain. More specifically, further substitutions of a human framework amino acid of the acceptor immunoglobulin with the corresponding amino acid from a donor immunoglobulin can be made at positions which fall into one or more of the following categories:

(1) the amino acid in the human framework region of the acceptor immunoglobulin is rare or unusual for human immunoglobulin sequences at that position, and the corresponding amino acid in the donor immunoglobulin is common for that position in human immunoglobulin sequences; or (2) the amino acid is immediately adjacent to one of the CDRs; or (3) the amino acid is predicted to be within about 3 angstroms of the CDRs in a three-dimensional immunoglobulin model and capable of interacting with the antigen or with the CDRs of the donor or humanized immunoglobulin.

Moreover, an amino acid in the acceptor sequence may optionally be replaced with an amino acid typical for human sequences at that position if:

(4) the amino acid in the acceptor immunoglobulin is rare for that position and the corresponding amino acid in the donor immunoglobulin is also rare, relative to other human sequences.

The humanized immunoglobulin chain will typically comprise at least about 3 amino acids from the donor immunoglobulin in addition to the CDRs, usually at least one of which is immediately adjacent to a CDR in the donor immunoglobulin. The heavy and light chains may each be designed by using any one or all three of the position criteria.

When combined into an intact antibody, the humanized light and heavy chains of the present invention will be substantially non-immunogenic in humans and retain substantially the same affinity as the donor immunoglobulin for the antigen (such as a protein or other compound containing an epitope). These affinity levels can vary from about $10^8$ $M^{-1}$ or higher, and may be within about 4 fold, preferably within about 2 fold of the donor immunoglobulin. Ideally, the humanized antibodies will exhibit affinity levels at least about 60 to 90% of the donor immunoglobulin's original affinity to the antigen.

Typically, one of the 3–5 most homologous heavy chain variable region sequences in a representative collection of at least about 10 to 20 distinct human heavy chains will be chosen as acceptor to provide the heavy chain framework, and similarly for the light chain. Preferably, one of the 1–3 most homologous variable regions will be used. The selected acceptor immunoglobulin chain will most preferably have at least about 65% homology in the framework region to the donor immunoglobulin.

In many cases, it may be considered preferable to use light and heavy chains from the same human antibody as acceptor sequences, to be sure the humanized light and heavy chains will make favorable contacts with each other. In this case, the donor light and heavy chains will be compared only against chains from human antibodies whose complete sequence is known, e.g., the Eu, Lay, Pom, Wol, Sie, Gal, Ou and WEA antibodies (see, e.g., "Sequences of Proteins of Immunological Interest," Kabat, E., et al., U.S. Department of Health and Human Services, (1987)); occasionally, the last few amino acids of a human chain are not known and must be deduced by homology to other human antibodies). The human antibody will be chosen in which the light and heavy chain variable regions sequences, taken together, are overall most homologous to the donor light and heavy chain variable region sequences. Sometimes greater weight will be given to the heavy chain sequence. The chosen human antibody will then provide both light and heavy chain acceptor sequences. In practice, it is often found that the human Eu antibody will serve this role.

Regardless of how the acceptor immunoglobulin is chosen, higher affinity may be achieved by selecting a small number of amino acids in the framework of the humanized immunoglobulin chain to be the same as the amino acids at those positions in the donor rather than in the acceptor. A second principle is that the following categories define what amino acids may be selected from the donor. Preferably, at many or all amino acid positions in one of the following categories, the donor amino acid will in fact be selected.

Category 1: The amino acid position is in a CDR is defined by see, e.g., "Sequences of Proteins of Immunological Interest," Kabat, E. et al., U.S. Department of Health and Human Services, (1987).

Category 2: If an amino acid in the framework of the human acceptor immunoglobulin is unusual (i.e., "rare", which as used herein indicates an amino acid occurring at that position in less than about 20% but usually less than about 10% of human heavy (respectively light) chain V region sequences in a representative data bank), and if the donor amino acid at that position is typical for human sequences (i.e., "common", which as used herein indicates an amino acid occurring in more than about 25% but usually more than about 50% of sequences in a representative data bank), then the donor amino acid rather than the acceptor may be selected. This criterion helps ensure that an atypical amino acid in the human framework does not disrupt the antibody structure. Moreover, by replacing an unusual amino acid with an amino acid from the donor antibody that happens to be typical for human antibodies, the humanized antibody may be made less immunogenic.

All human light and heavy chain variable region sequences are respectively grouped into "subgroups" of sequences that are especially homologous to each other and have the same amino acids at certain critical positions (see, e.g., "Sequences of Proteins of Immunological Interest," Kabat, E., et al., U.S. Department of Health and Human Services, (1987)). When deciding whether an amino acid in a human acceptor sequence is "rare" or "common" among human sequences, it will often be preferable to consider only those human sequences in the same subgroup as the acceptor sequence.

Category 3: In the positions immediately adjacent to one or more of the 3 CDRs in the primary sequence of the humanized immunoglobulin chain, the donor amino acid(s) rather than acceptor amino acid may be selected. These amino acids are particularly likely to interact with the amino acids in the CDRs and, if chosen from the acceptor, to distort the donor CDRs and reduce affinity. Moreover, the adjacent amino acids may interact directly with the antigen (Amit et al., Science, 233, 747–753 (1986), which is incorporated herein by reference) and selecting these amino acids from the donor may be desirable to keep all the antigen contacts that provide affinity in the original antibody.

Category 4: A 3-dimensional model, typically of the original donor antibody, shows that certain amino acids outside of the CDRs are close to the CDRs and have a good probability of interacting with amino acids in the CDRs by hydrogen bonding, Van der Waals forces, hydrophobic interactions, etc. At those amino acid positions, the donor immunoglobulin amino acid rather than the acceptor immunoglobulin amino acid may be selected. Amino acids according to this criterion will generally have a side chain atom within about 3 angstrom units of some atom in the CDRs and must contain an atom that could interact with the CDR atoms according to established chemical forces, such as those listed above. In the case of atoms that may form a hydrogen bond, the 3 angstroms is measured between their nuclei, but for atoms that do not form a bond, the 3 angstroms is measured between their Van der Waals surfaces. Hence, in the latter case, the nuclei must be within about 6 angstroms (3+sum of the Van der Waals radii) for the atoms to be considered capable of interacting. In many cases the nuclei will be from 4 or 5 to 6 angstroms apart. In determining whether an amino acid can interact with the CDRs, it is preferred not to consider the last 8 amino acids of heavy chain CDR 2 as part of the CDRs, because from the viewpoint of structure, these 8 amino acids behave more as part of the framework.

Amino acids in the framework that are capable of interacting with amino acids in the CDRs, and which therefore belong to Category 4, may be distinguished in another way. The solvent accessible surface area of each framework amino acid is calculated in two ways: (1) in the intact antibody, and (2) in a hypothetical molecule consisting of the antibody with its CDRs removed. A significant difference between these numbers of about 10 square angstroms or more shows that access of the framework amino acid to solvent is at least partly blocked by the CDRs, and therefore that the amino acid is making contact with the CDRs. Solvent accessible surface area of an amino acid may be calculated based on a 3-dimensional model of an antibody, using algorithms known in the art (e.g., Connolly, *J. Appl. Cryst.* 16, 548 (1983) and Lee and Richards (1971) *J. Mol. Biol.* 55:379, both of which are incorporated herein by reference). Framework amino acids may also occasionally interact with the CDRs indirectly, by affecting the conformation of another framework amino acid that in turn contacts the CDRs.

The amino acids at several positions in the framework are known to be capable of interacting with the CDRs in many antibodies (Chothia and Lesk (1987) *J. Mol. Biol.* 196:901; Chothia et al. (1989) *Nature* 342:877; and Tramontano et al. (1990) *J. Mol. Biol.* 215:75, all of which are incorporated herein by reference), notably at positions 2, 48, 64 and 71 of the light chain and 26–30, 71 and 94 of the heavy chain (numbering according to Kabat, op. cit.), and therefore these amino acids will generally be in Category 4. Typically, humanized immunoglobulins, of the present invention will include donor amino acids (where different) in category 4 in addition to these.

Computer programs to create models of proteins such as antibodies are generally available and well known to those skilled in the art (see, Levy et al. (1989) *Biochemistry* 28:7168–7175; Bruccoleri et al. (1988) *Nature* 335:564–568; Chothia et al. (1986) *Science* 233:755–758, all of which are incorporated herein by reference). Indeed, because all antibodies have similar structures, the known antibody structures, which are available from the Brookhaven Protein Data Bank, can be used if necessary as rough models of other antibodies. Commercially available computer programs can be used to display these models on a computer monitor, to calculate the distance between atoms, and to estimate the likelihood of different amino acids interacting (see, Ferrin et al. (1988) *J. Mol. Graphics* 6:13–27).

In addition to the above categories, which describe when an amino acid in the humanized immunoglobulin may be taken from the donor, certain amino acids in the humanized immunoglobulin may be taken from neither the donor nor acceptor, if they fall into:

Category 5: If the amino acid at a given position in the donor immunoglobulin is "rare" for human sequences, and the amino acid at that position in the acceptor immunoglobulin is also "rare" for human sequences, as defined above, then the amino acid at that position in the humanized immunoglobulin may be chosen to be some amino acid "typical" of human sequences. A preferred choice is the amino acid that occurs most often at that position in the known human sequences belonging to the same subgroup as the acceptor sequence.

Human constant region DNA sequences can be isolated in accordance with well known procedures from a variety of human cells, but preferably immortalized B-cells (see, e.g., "Sequences of Proteins of Immunological Interest," Kabat, E., et al., U.S. Department of Health and Human Services, (1987) and WO87/02671). The CDRs for producing the immunoglobulins of the present invention will be similarly derived from monoclonal antibodies capable of binding to CTLA4 and produced in any convenient mammalian source, including, mice, rats, rabbits, or other vertebrate capable of producing antibodies by well known methods. Suitable source cells for the polynucleotide sequences and host cells for immunoglobulin expression and secretion can be obtained from a number of sources, such as the American Type Culture Collection (Catalogue of Cell Lines and Hybridomas, Fifth edition (1985) Rockville, Md., U.S.A., which is incorporated herein by reference).

In another embodiment, antibody chains or specific binding pair members can be produced by recombination between vectors comprising nucleic acid molecules encoding a fusion of a polypeptide chain of a specific binding pair member and a component of a replicable genetic display package and vectors containing nucleic acid molecules encoding a second polypeptide chain of a single binding pair member using techniques known in the art, e.g., as described in U.S. Pat. Nos. 5,565,332, 5,871,907, 5,858,657, or 5,733,743.

IV. Immunotoxins

An antibody or antibody portion of the invention can be derivatized or linked to another functional molecule (e.g., a peptide or polypeptide). Accordingly, the antibodies and antibody portions of the invention are intended to include derivatized and otherwise modified forms of the anti-CTLA4 antibodies described herein, including, e.g., antibodies conjugated to other molecules (e.g., antibodies or polypeptides which bind to other T cell markers T cells). For example, an antibody or antibody portion of the invention can be functionally linked (by chemical coupling, genetic fusion, noncovalent association or otherwise) to one or more other molecular entities, such as another antibody (e.g., to create a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

In one embodiment, anti-CTLA4 antibody or an antigen binding portion thereof is infused into a subject to bring about destruction of activated T cells. CTLA4 is expressed exclusively on activated T cells. Thus, because CTLA4 is present only on activated T cells, an immunotoxin that binds to and targets CTLA4 can be used to deplete these specific cells (e.g., by ablation by conjugating a toxic moiety to the antibody).

A wide variety of toxic moieties are known in the art and may be conjugated to the antibodies of the invention (see Hertler and Frankel (1989) *J. Clin. Oncol.* 7:1932–1942). For example, toxic moieties may disrupt the cell membrane without internalization, toxic moieties may be internalized via a non-specific mechanism, or toxic moieties may be specifically internalized, e.g. by direct interaction with specific receptor proteins on the cell. Toxic moieties for use in the claimed invention can be e.g., naturally occurring or synthetic. Toxic moieties may be proteinaceous or non-proteinaceous, e.g., oligosaccharides. Examples include: numerous useful plant-, fungus- or even bacteria-derived toxic moieties, which, by way of example, include various A chain toxic moieties, particularly ricin A chain, ribosome inactivating proteins such as saporin or gelonin, .alpha.-sarcin, aspergillin, restrictocin, ribonucleases such as placental ribonuclease, angiogenic, diphtheria toxin, and pseudomonas exotoxin, and calicheamicin and will be discussed in more detail below.

For example, in one embodiment, exemplary toxic moieties include "ribosome inactivating proteins" (RIPs) which by definition are able to directly inhibit the ribosomal translational machinery. The heterodimer peptide ricin is derived from the castor bean plant (*Ricinus communes*) and is an example of such a toxic moiety. The toxic activity of ricin is found entirely in one of its subunits (ricin A-chain). In one embodiment, a toxic moiety for use in the claimed invention is an active subunit of a toxin molecule. Ricin A-chain is thought to deactivate ribosome function by specifically depurinating the single adenine at position 4324 of 28S rRNA (Chen et al. (1998) *Biochemistry* 37:11605, Koehler et al. (1994) *Bone Marrow Transplant* 13:571–575; Duke-Cohan et al. (1993) *Blood* 82:2224–34). Another bipartite RIP toxic moiety is abrin, which is derived from the jequirity bean (*Abrus precatorius*) and is known to deactivate protein translation by the same mechanism as ricin-A (Krupakar et al. (1999) *Biochem. J.* 338:273–279). Other RIPs which can be used in connection with the invention include the plant cytotoxins saporin and gelonin. The Shiga-A toxic moiety from the microorganism *Shigella dysenteriae* also functions as an RIP (Fraser, M. E. (1994) *Nat. Structural Biol.* 1:59–64), as does the sarcin-A toxic moiety, derived from the mold *Aspergillus giganteus* (Lacadena et al. (1999) *Proteins* 37:474–484). Antibody-toxic moiety conjugates which include ricin-A and similar toxic moieties have been described previously in U.S. Pat. Nos. 4,590,017, 4,906,469, 4,919,927, and 5,980,896, which are expressly incorporated herein by reference.

Toxic moieties which ADP-ribosylate the protein elongation factor 2 (EF-2), e.g., bacterial diphtheria toxin (from *Corynebacterium diphtheriae*) and inhibit protein synthesis (Foley et al. (1995) *J. Biol. Chem.* 270:23218–23225) can also be used in the antibody-toxic moiety conjugates of the invention. Antibody-toxic moiety conjugates which include diphtheria toxin or related toxic moieties which ADP-ribosylate the EF-2 have been described previously, e.g., in U.S. Pat. No. 4,545,985.

Other potent toxic moieties are able to able to bring about eukaryotic cell death by interfering with microtubule function, thus causing mitotic arrest (Iwasaki (1998) *Yakugaku Zasshi* 118:112–126). Examples of such toxic moieties are the maytansinoid compounds (Takahashi et al. (1989) *Mol. Gen. Genet.* 220:53–59) which are found in certain mosses (e.g., *maytenus buchananii*; see Larson et al. (1999) *J. Nat. Prod.* 62:361–363). Antibody-toxic moiety conjugates which include maytansinoid have been described previously in U.S. Pat. No. 5,208,020.

Still other toxic moieties are able to activate the adenylate cyclase cAMP system, causing unregulated transport of anions and cations through the membrane. An example of this type of toxic moiety is the cholera toxin (de Haan et al. (1998) *Immunol. Cell Biol.* 76:270–279) derived from *Vibrio cholerae*, a microorganism that can cause fluid secretion and hemorrhage of intestinal cells.

The bacterial pertussis toxin (derived from *Bordetella pertussis*) is able to specifically target the eukaryotic G protein complex, a key element in the transduction of many extracellular signal pathways, including those triggered by cytokine and hormone receptors. The pertussis toxin can ADP-ribosylate a subunit of the G protein complex, causing an uncoupling of its regulatory activity (Locht and Antoine (1995) *Biochimie* 77:333–340).

In one embodiment, a toxic moiety for use in the antibody-toxic moiety conjugates of the invention is an oligosaccharide. For example, the oligosaccharide calicheamicin is a bacterial product which was identified as one of a class of carbohydrates which preferentially bind the minor groove of DNA (Kahne (1995) *Chem. Biol.* 2:7–12). Calicheamicin is known to non-specifically abstract the hydrogen atom from the 4'carbon of DNA deoxyribose groups causing double stranded DNA breaks with terminal 3'-phosphoglycolate groups which are refractory to normal cellular repair mechanisms (Chaudhry et al. (1999) *Biochem. Pharmacol.* 57:531–538). Calicheamicin is a preferred toxic moiety for use in connection with the invention. Antibody calicheamicin conjugates have been described (Sievers et al. (1999) *Blood* 93:3678–3684; Lode et al. (1998) *Cancer Res.* 58:2925–2928). Other synthetic cytotoxic compounds, such as CC-1065, have similar DNA-fragmenting mechanisms as calichearnicin and are also known in the art (Gunz and Naegeli (1996) *Biochem. Pharmacol.* 52:447–453). Antibody-toxic moiety conjugates, in which calicheamicin is covalently attached to an antibody through disulfide bonds, have been described previously in U.S. Pat. Nos. 5,773,001 and 5,739,116.

Another exemplary class of toxic moieties are bacterial toxic moieties which are able to form lethal holes in eukaryotic membranes, thus causing cell death without the need for endocytotic internalization. Aerolysin is one example of such a toxic moiety. Aerolysin can form hepatomer channels through a membrane upon binding to a cell surface (Parker et al. (1996) *Mol. Microbiol.* 19:205–212; Buckley (1991) *Experimentia* 47:418–419). Molecular conjugates which include aerolysin have been described previously in U.S. Pat. Nos. 5,824,776 and 5,817,771.

There are numerous methods known in the art for conjugating a toxic moiety to an antibody such that the activity of the toxic moiety is appropriately delivered upon binding of the antibody to a cell (Ghose and Blair (1987) *Crit. Rev. Ther. Drug Carrier Syst.* 3:263–359; Hermentin and Seiler (1988) *Behring Inst. Mitt.* 82:197–215.). For example, when the cytotoxic agent is a protein and the second component is an intact immunoglobulin, the linkage may be by way of heterobifunctional cross-linkers, e.g., SPDP, carbodiimide, glutaraldehyde, or the like. Production of various immunotoxins is well-known with the art, and can be found, for example in "Monoclonal Antibody-Toxin Conjugates: Aiming the Magic Bullet," Thorpe et al., Monoclonal Antibodies in Clinical Medicine, Academic Press, pp. 168–190 (1982), which is incorporated herein by reference. The components may also be linked genetically (see, Chaudhary et al., Nature 339, 394 (1989), which is herein incorporated by reference). Further methods for conjugating a toxic moiety to an antibody may also found in, for example, Amon et al. (1985) "Monoclonal Antibodies For Immunotargeting of Drugs in Cancer Therapy" in *Monoclonal Antibodies And Cancer Therapy*, Reisfeld et al. eds., Alan R. Liss, Inc. pp. 243–256; Hellstrom et al. (1987) "Antibodies For Drug Delivery" in *Controlled Drug Delivery*, 2nd ed., Robinson et al. eds., Marcel Dekker, Inc., pp. 623–653; Thorpe (1985) "Antibody Carriers Of Cytotoxic Agents In Cancer Therapy: A Review" in *Monoclonal Antibodies '84: Biological and Clinical Applications*, Pinchera et al. eds., pp. 475–506; "Analysis, Results, And Future Prospective Of The Therapeutic Use Of Radiolabeled Antibody In Cancer Therapy" in *Monoclonal Antibodies for Cancer Detection and Therapy*, Baldwin et al. eds., Academic Press, pp. 303–316, 1985; and Thorpe et al. (1982) *Immunol. Rev.* 62:119–158.

For example, in one embodiment, a covalent linkage can be formed between the antibody and the toxic moiety. In some cases, the existing cell-binding portion of a toxic moiety must first be removed or altered to suppress its non-specific activity (Hertler and Frankel (1989) *J. Clin. Oncol.* 7:1932–1942). The covalent linkage of antibody to toxic moiety generally involves formation of a thioester or a disulfide bond. For example, conjugate compounds can be prepared by using N-succinimidyl-3-2(pyridyldithio)propionate, which can generate a disulfide linkage between an antibody and a toxic moiety (Colombatti et al. (1983) *J. Immunology.* 131:3091–3095). Numerous types of disulfide-bond containing linkers are known which can successfully be employed to conjugate the toxic moiety with a polypeptide.

In one embodiment, linkers used to conjugate a toxic moiety to an antibody are hydrolyzable (see U.S. Pat. Nos. 5,714,586 and 5,712,374 and EP 0689845). For example, such hydrolyzable linkers may contain two functional groups. One group typically is a carboxylic acid that is utilized to react with the antibody. The acid functional group, when properly activated, can form an amide linkage with a free amine group of the antibody, such as, for example, the amino in the side chain of a lysine residue in the antibody. The other functional group commonly is a carbonyl group, e.g., an aldehyde or a ketone, which will react with a hydrazide group on the toxic moiety to form a hydrazone linkage. This linkage is hydrolyzable at the target cell (e.g., the cell being contacted by the antibody-toxic moiety conjugate) to release the toxic moiety from the antibody-toxic moiety conjugate. In one embodiment, linkers that contain a disulfide bond that is sterically "hindered" are preferred, due to their greater stability in vivo, thus preventing release of the toxic moiety prior to binding at the site of action.

Other methods forming antibody-toxic moiety conjugates are known in the art, such as those described in U.S. Pat.

Nos. 4,894,443, 5,208,021, 4,340,535, 5,877,296, 5,773,001, 5,767,285, 5,739,116, 5,714,586, 5,053,394, and 5,712,374, and in EP 44167 and EP 0689845.

V. Expression of Antibodies

An antibody, or antigen binding portion, of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used obtain antibody heavy and light chain genes, incorporate these genes into recombinant expression vectors and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss et al.

To express an anti-CTLA4 antibody, DNA fragments encoding the light and heavy chain variable regions are first obtained. These DNAs can be obtained by amplification and modification of gernline light and heavy chain variable sequences using the polymerase chain reaction (PCR). Germline DNA sequences for human heavy and light chain variable region genes are known in the art (see e.g., the "Vbase" human germline sequence database; see also Kabat, E. A., et al. (1991) *Sequences of Proteins of Immunological Interest, Fifth Edition*, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776–798; and Cox, J. P. L. et al. (1994) "A Directory of Human Germ-line $V_K$ Segments Reveals a Strong Bias in their Usage" *Eur. J. Immunol.* 24:827–836; the contents of each of which are expressly incorporated herein by reference).

To express the antibodies, or antigen binding portions of the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the antibody-related light or heavy chain sequences, the expression vector may already carry antibody constant region sequences. For example, one approach to converting the antibody-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

The nucleic acid sequences of the present invention capable of ultimately expressing the desired humanized antibodies can be formed from a variety of different polynucleotides (genomic or cDNA, RNA, synthetic oligonucleotides, etc.) and components (e.g., V, J, D, and C regions), as well as by a variety of different techniques. Joining appropriate genomic and synthetic sequences is presently the most common method of production, but cDNA sequences may also be utilized (see, European Patent Publication No. 0239400 and Reichmann, L. et al., Nature 332, 323–327 (1988), both of which are incorporated herein by reference).

In addition to the antibody chain genes, the recombinant expression vectors of the invention carry regulatory sequences that control the expression of the antibody chain genes in a host cell. The term "regulatory sequence" includes promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12–13).

Preferred mammalian host cells for expressing the recombinant antibodies of the invention include Chinese Hamster Ovary (CHO cells) (including dhfr-CHO cells, described in Urlaub and Chasin (1980) *Proc. Natl. Acad. Sci. USA* 77:4216–4220, used with a DHFR selectable marker, e.g., as described in R. J. Kaufman and P. A. Sharp (1982) *Mol. Biol.* 159:601–621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It will be understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to CTLA4. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than CTLA4 by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

Antibodies, (e.g., whole antibodies, their dimers, individual light and heavy chains, or other immunoglobulin forms of the present invention), can be purified according to standard procedures of the art, including ammonium sulfate precipitation, affinity columns, column chromatography, gel electrophoresis and the like (see, generally, R. Scopes, "Protein Purification", Springer-Verlag, N.Y. (1982)). Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically (including extracorporeally) or in developing and performing assay procedures, immunofluorescent stainings, and the like. (See, generally, Immunological Methods, Vols. I and II, Lefkovits and Pemis, eds., Academic Press, New York, N.Y. (1979 and 1981)).

In view of the foregoing, another aspect of the invention pertains to nucleic acid, vector and host cell compositions that can be used for recombinant expression of the antibodies and antibody portions of the invention. For example, preferred portions of the heavy chain variable region of antibody 26 include: FR1, amino acids 1–28; CDR1, amino acids 29–35; FR2, amino acids 36–49; CDR2, amino acids 50–66; FR3, amino acids 67–97; CDR3, amino acids 98–111; FR4, amino acids 112–123. The various regions of the light chain variable region of antibody 26 include: FR1, amino acids 1–23; CDR1, amino acids 24–33; FR2, amino acids 34–48; CDR2, amino acids 49–55; FR3, amino acids 56–77; CDR3, amino acids 78–87; FR4, amino acids 88–106.

In one aspect the invention pertains to a nucleic acid molecule comprising a nucleotide sequence shown in SEQ ID NO:3 (mouse antibody 26 VH sequence), 5 (mouse antibody 26 VK sequence), 7 (humanized antibody 26 VK sequence), or 9 (humanized antibody 26 VH sequence).

In another aspect, the invention pertains to a polypeptide comprising an amino acid sequence shown in SEQ ID NO: SEQ ID NO:4 (mouse antibody 26 VH sequence), 6 (mouse antibody 26 VK sequence), 8 (humanized antibody 26 VK sequence), or 10 (humanized antibody 26 VH sequence).

It will be appreciated by the skilled artisan that nucleotide sequences encoding antibodies, or portions thereof (e.g., a CDR domain, such as a CDR3 domain), can be derived from the nucleotide sequences encoding the antibody using the genetic code and standard molecular biology techniques.

The invention also provides recombinant expression vectors encoding both an antibody heavy chain and an antibody light chain. For example, in one embodiment, the invention provides a recombinant expression vector encoding:

a) an antibody light chain having a variable region found in antibody 26 or the humanized form thereof; and b) an antibody heavy chain having a variable region found in antibody 26 or the humanized form thereof.

The invention also provides host cells into which one or more of the recombinant expression vectors of the invention have been introduced. Preferably, the host cell is a mammalian host cell, more preferably the host cell is a CHO cell, an NS0 cell or a COS cell.

Still further the invention provides a method of synthesizing a recombinant human antibody of the invention by culturing a host cell of the invention in a suitable culture medium until a recombinant human antibody of the invention is synthesized. The method can further comprise isolating the recombinant human antibody from the culture medium.

In one embodiment, anti CTLA4 antibodies can be administered in multivalent form (e.g., to downmodulate an immune response) CTLA4 antibodies or antigen binding portions thereof can be incorporated into constructs for downmodulating the immune response by expressing them on or attaching them to a surface that, upon introduction into a subject, would be exposed to the extracellular milieu. In this manner, the antigen binding portion of the antibody is available to bind to the appropriate molecules expressed on a T cell of the subject to which the constructs are administered.

Such constructs can comprise a surface which acts to anchor an antigen-binding portion of an antibody that binds to CTLA4. A variety of different surfaces can be used in making the constructs of the invention. For example, in one embodiment, antibody binding portions can be attached to polymers comprising an exposed surface. Exemplary polymers include polysaccharides, acrylic polymers (e.g., polyacrolein or polystyrene or poly (alpha-hydroxy acids)), lactic acid polymers, or copolymers such as, polymers of lactic and glycolic acids. Beads and microbeads comprising a surface to which antigen binding portions of anti-CTLA4 antibody can be attached are known in the art (see, e.g., U.S. Pat. No. 5,871,747 and the like).

In another embodiment, such a construct can comprise a lipid bilayer. For example, a construct can be an acellular construct, e.g., a liposome or a micelle. In yet another embodiment, a construct for use in the instant invention is a cell, such as a prokaryotic or a eukaryotic cell. Cells may be derived from any tissue or organ. Exemplary cells are derived from peripheral blood. Preferred cells include cells that can be maintained in culture.

In one embodiment, a cell for use in a construct of the invention is a syngeneic cell. In another embodiment, a cell for use in a construct of the invention is an allogeneic cell. In yet another embodiment, a cell for use in a construct of the invention is a xenogeneic cell. In one embodiment, e.g., when the cell is an allogeneic or a xenogenic cell, the cell is selected to provide a missing or diminished function in the subject. For example, in the case of a subject that would benefit from transplantation of a liver cell, a liver cell can be used in the subject construct.

A cell for use in a construct of the invention can be a wild-type (naturally occurring) cell or can comprise alterations that optimize its use in the subject constructs. In another embodiment, such a cell can be altered to express molecules which enhance its ability to bind to a T cell in a subject, e.g., by altering the cell to express adhesion molecules. For example, such a cell can be altered to eliminate expression of molecules that promote immunostimulation (e.g., CD28 or cytokines). In another example, such a cell can be altered to modify the ability of such a cell to process antigen so that the peptides presented by the cell can be controlled (e.g., by introducing a defect in antigen processing, see e.g., U.S. Pat. No. 5,731,160).

Surface-bound anti-CTLA4 antibodies can be attached to an exposed surface using a variety of art-recognized techniques, e.g., U.S. Pat. No. 6,046,173. For example, in one embodiment a molecule for attachment can be associated with the exposed surface of the construct, e.g., in a covalent linkage. Covalent linkage includes, e.g., linkage by a bifunctional coupling agent and oxidative linkage. In one embodiment a molecule for attachment can be attached to the exposed surface directly (e.g., to the surface itself). In another embodiment, a molecule can be attached indirectly (e.g., attached to another molecule, such as a lipid (e.g., a fatty acid chain or prenyl group) or a polypeptide, present on the exposed surface.

Many bifunctional coupling agents are useful for coupling organic molecules possessing various types of functional groups to proteins, including antibody molecules. The conjugation of organic molecules to proteins, including proteins possessing antibody specificity, is well-known in the art and is described, for example, in P. Tijssen, "Practice and Theory of Enzyme Immunoassays" (Elsevier, Amsterdam, 1985), pp. 279–296, incorporated herein by this reference.

Briefly, organic molecules containing carboxyl groups or that can be carboxylated, can be coupled by the mixed anhydride reaction, by reaction with a water-soluble carbodiimide, or esterification with N-hydroxysuccinimide. Carboxylation can be performed by reactions such as alkylation of oxygen or nitrogen substituents with haloesters, followed by hydrolysis of the ester, or the formation of hemisuccinate esters or carboxymethyloximes on hydroxyl or ketone groups of steroids.

Organic molecules with amino groups or nitro groups reducible to amino groups can be converted to diazonium salts and reacted with proteins at mildly alkaline pH, for aromatic amines. Organic molecules with aliphatic amines can be conjugated to proteins by various methods, including reaction with carbodiimides, reaction with the homobifunctional reagent tolylene-2,4-diisocyanate, or reaction with maleimide compounds. Aliphatic amines can also be converted to aromatic amines by reaction with p-nitrobenzoylchloride and subsequent reduction to a p-aminobenzoylamide, which can then be coupled to proteins after diazotization. Also, bifunctional imidate esters, such as dimethylpimelimidate, dimethyladipimidate, or dimethylsuberimidate, can be used to conjugate amino group-containing organic molecules to proteins.

Thiol-containing organic molecules can be conjugated to proteins with malemides, such as 4-(N-maleimidomethyl)-cyclohexane-1-carboxylic acid N-hydroxysuccinimide ester.

For organic molecules with hydroxyl groups, an alcohol function can be converted to the hemisuccinate, which introduces a carboxyl group available for conjugation. Alternatively, the bifunctional reagent sebacoyldichloride converts an alcohol to an acid chloride, which then reacts with proteins.

Phenols can be activated with diazotized p-aminobenzoic acid, which introduces a carboxyl group, and can then be reacted with the proteins by the mixed anhydride reaction. Sugars can be activated by forming a p-nitrophenyl glycoside, followed by reduction of the nitro group to an amino group and conjugation by diazotization. Other methods include the cleavage of vicinal glycols of sugars to aldehydes by reaction with periodate, followed by coupling to amines by reductive alkylation with sodium borohydride. Alternatively, hydroxyl containing organic molecules can be conjugated after conversion to chlorocarbonates by reaction with phosgene.

For organic molecules with aldehyde or ketone groups, carboxyl groups can be introduced through the formation of O-carboxymethyloximes. Ketone groups can also be derivatized with p-hydrazinobenzoic acid to produce carboxyl groups.

Organic molecules containing aldehydes can be directly conjugated through the formation of Schiff bases that are stabilized by reaction with a reducing agent such as sodium borohydride.

Oxidative linkages can also be used. Oxidative linkage is particularly useful when coupling radioactive iodine to antibodies. Suitable methods include: (1) chemical oxidation with chloramine-T; (2) chemical oxidation with iodogen (1,3,4,6-tetrachloro 3.alpha.,6.alpha.-diphenylglycoluril); (3) oxidation with the enzyme lactoperoxidase. Although not an oxidative procedure, another useful method for labeling with iodine is with $^{125}$I N-succinimidyl 3-(4-hydroxyphenylpropionate), generally known as Bolton-Hunter reagent. These techniques are described, e.g., in E. Harlow and D. Lane, "Antibodies: A Laboratory Manual" (Cold Spring Harbor Laboratory, Cold Spring Harbor, N.Y., 1988), pp. 324–339.

In another embodiment, an anti-CTLA4 antibody can be attached via a transmembrane domain (e.g., a membrane-spanning region of an integral membrane protein). Such a domain can be derived from the protein to be attached or from a different protein. For example, integral membrane proteins from which transmembrane domains can be derived include cell surface receptors (e.g., growth factor receptors), adhesion molecules (e.g., integrins, or selectins), or CD antigens. For example, transmembrane domains can be Type I domains which comprise about 25 hydrophobic amino acid residues and are usually followed by a cluster of basic amino acids (e.g., as found in CD2, CD40, or IL-4 receptor). Type II transmembrane domains can also be used. Type II domains cross the membrane such that the carboxy-terminal portion of the polypeptide is extracellular (e.g., in the case of CD72). Type III transmembrane domains can also be employed. Such domains cross a lipid bilayer numerous times (e.g., as in the case of G-protein linked receptors).

In another embodiment, a molecule can be attached to the subject constructs using a glycosylphosphatidylinositol (GPI) anchor attached to the carboxy-terminal residue of the molecule. For example, GPI anchors can be derived from human placental alkaline phosphatase (see, e.g., Whitehorn et al. 1995 Biotechnology 13:1215–1219). GPI anchored molecules may have a signal sequence at their carboxy-terminus that is cleaved off and replaced by the GPI anchor (see, e.g., U.S. Pat. No. 5,891,432).

In another embodiment, a cell can be caused to express a molecule comprising a CTLA4 binding molecule (e.g., an anti-CTLA4 antibody or antigen binding portion thereof). For example, as set forth above, active molecules can be linked to cells as well as other surfaces to form the constructs of the invention. In addition, cells can be caused to express an active molecule by various nucleic acid manipulation procedures.

Techniques for nucleic acid manipulation are well known. (See, e.g., Sambrook et al., (1989); Ausubel et al. (1987) and in Annual Reviews of Biochemistry, 61:131–156 (1992)). Reagents useful in applying such techniques, such as restriction enzymes and the like, are widely known in the art and commercially available from a number of vendors.

Nucleic acid sequences encoding the selected molecules for expression in the invention may be obtained using known procedures for molecular cloning and replication of the vector or plasmid carrying the sequences in a suitable host cell.

Nucleic acid sequences for use in the present invention may also be produced in part or in total by chemical synthesis, e.g. by the phosphoramidite method described by Beaucage and Carruthers, Tetra. Letts. 22:1859–1862 (1981), or the triester method (Matteucci et al., J. Am. Chem. Soc. 103:3185 (1981)), and may be performed on commercial automated oligonucleotide synthesizers. A double-stranded fragment may be obtained from the single-stranded product of chemical synthesis either by synthesizing the complementary strand and annealing the strand together under appropriate conditions, or by synthesizing the complementary strand using DNA polymerase with an appropriate primer sequence.

The natural or synthetic nucleic acid fragments coding for a desired sequence may be incorporated into vectors capable of introduction into and replication in a prokaryotic or eukaryotic cell. Usually the vectors are suitable for replication in a unicellular host, such as yeast or bacteria, but may also be introduced into cultured mammalian or plant or other eukaryotic cell lines, with or without integration within the genome. The vectors will typically comprise an expression system recognized by the host cell, including the intended recombinant nucleic acid fragment encoding the desired polypeptide. The vectors will also contain a selectable marker, i.e. a gene encoding a protein needed for the survival or growth of a host cell transformed with the vector. The presence of this gene ensures the growth of only those host cells which express the inserted nucleic acid of interest. Typical selection genes encode proteins that 1) confer resistance to antibiotics or other toxic substances, e.g. ampicillin, neomycin, methotrexate, etc.; b) complement auxotrophic deficiencies, or c) supply critical nutrients not available from complex media, e.g. the gene encoding D-alanine racemase for Bacilli. The choice of the proper selectable marker will depend on the host cell, and appropriate markers for different hosts are well known in the art. Such vectors may be prepared by means of standard recombinant techniques well known in the art (Sambrook et al., (1989); Ausubel et al., (1987)).

For gene transfer into the cells to express the selected molecules, nucleic acid may be directly introduced ex vivo in the form of "naked" nucleic acid, e.g. by microinjection, electroporation, as calcium-phosphate-DNA gels, with DEAE dextran, or in encapsulated form, e.g. in vesicles such as liposomes, or in a suitable viral vector.

Vectors containing the nucleic acid encoding the desired molecules for expression are preferably recombinant expression vectors in which high levels of gene expression may occur, and which contain appropriate regulatory sequences for transcription and translation of the inserted nucleic acid sequence. Regulatory sequences refers to those sequences normally associated (e.g. within 50 kb) of the coding region of a locus which affect the expression of the gene (including transcription of the gene, and translation, splicing, stability or the like, of the messenger RNA). A transcriptional regulatory region encompasses all the elements necessary for transcription, including the promoter sequence, enhancer sequence and transcription factor binding sites. Regulatory sequences also include, inter alia, splice sites and polyadenylation sites. An internal ribosomal entry site(IRES) sequence may be placed between recombinant coding sequences to permit expression of more than one coding sequence with a single promoter.

Exemplary transcriptional control regions include: the SV40 early promoter region, the cytomegalovirus (CMV) promoter (human CMV IE94 promoter region (Boshart et al, Cell, 41:521–530 (1985)); the promoter contained in the 3' long terminal repeat of Rous sarcoma virus or other retroviruses; the herpes thymidine kinase promoter; the regulatory sequences of the methallothionein gene; regions from the human IL-2 gene (Fujita et al., Cell, 46:401–407 (1986)); regions from the human IFN gene (Ciccarone et al., J. Immunol. 144:725–730 (1990)); regions from the human IFN gene (Shoemaker et al., Proc. Natl. Acad. Sci. USA 87:9650–9654 (1990)); regions from the human IL-4 gene (Arai et al., J. Immunol. 142:274–282 (1989)); regions from the human lymphotoxin gene (Nedwin et al., Nucl. Acids. res. 13:6361–6373 (1985)); regions from the human granulocyte-macrophage CSF gene (GM-CSF) (Miyatake et al., EMBO J. 4:2561–2568 (1985)); and others. When viral vectors are employed, recombinant coding sequences may be positioned in the vector so that their expression is regulated by regulatory sequences such as promoters naturally residing in the viral vector.

In addition, operational elements may include leader sequences, termination codons, and other sequences needed or preferred for the appropriate transcription and subsequent translation of the inserted nucleic acid sequences.

Secretion signals may also be included whether from a native protein, or from other secreted polypeptides of the same or related species, which permit the molecule to enter cell membranes, and attain a functional conformation.

It will be understood by one skilled in the art that the correct combination of expression control elements will depend on the recipient ("host") cells chosen to express the molecules. The expression vector should contain additional elements needed for the transfer and subsequent replication of the expression vector containing the inserted nucleic acid sequences in the host cells. Examples of such elements include, but are not limited to, origins of replication and selectable markers.

The vector may contain at least one positive marker that enables the selection of cells carrying the inserted nucleic acids. The selectable molecule may be a gene which, upon introduction into the cell, expresses a dominant phenotype permitting positive selection of cells carrying the gene. Genes of this type are known in the art and include, for example, drug resistance genes such as hygromycin-B phosphotransferase (hph) which confers resistance to the antibiotic G418; the aminoglycoside phosphotransferase gene (neo or aph) from Tn5 which codes for resistance to the antibiotic G418; the dihydrofolate reductase (DHRF) gene; the adenosine deaminase gene (ADA) and the multi-drug resistance (MDR) gene.

Suitable vectors for the invention may be plasmid or viral vectors, including baculoviruses, adenoviruses, poxviruses, adenoassociated viruses (AAV), and retroviral vectors (Price et al, Proc. Natl. Acad. Sci. USA 84:156–160 (1987) such as the MMLV based replication incompetent vector pMV-7 (Kirschmeier et al., DNA 7:219–225 (1988)), as well as human and yeast artificial chromosomes (HACs and YACs). Plasmid expression vectors include plasmids including pBR322, pUC or BLUESCRIPT™ (Stratagene, San Diego, Calif.). Exemplary vectors are described e.g., in U.S. Pat. Nos. 6,040,147; 6,033,908; 6,037,172; 6,027,722; 5,741,486; 5,656,465.

Recombinant viral vectors are introduced into cells using standard infection conditions. Infection techniques have been developed which use recombinant infectious virus particles for gene delivery into cells. Viral vectors used in this way include vectors derived from simian virus 40 (SV40; Karlsson et al., Proc. Natl. Acad. Sci. USA 82:158 (1985)); adenoviruses(Karlsson etl al., EMBO J., 5:2377 (1986)); AAV (Carter, Current Opinion in Biotechnology, 3:533–539 (1992)); vaccinia virus (Moss, et. al., Vaccine, 6:161–3, 1988)); and retroviruses (Coffin, in Weiss et al., (eds.), RNA Tumor Viruses, 2nd ed. Vol. 2, Cold Spring Laboratory, New York, pp. 17–71 (1985)).

In retroviral vectors, genes are inserted so as to be under the transcriptional control of the promoter incorporated in the retroviral long terminal repeat (LTR), or by placing them under the control of a heterologous promoter inserted between the LTRs. This latter strategy provides a way of coexpressing a dominant selectable marker gene in the vector, thus permitting selection of cells that are expressing specific vector sequences.

Nonreplicating viral vectors can be produced in packaging cell lines which produce virus particles which are infectious but replication defective, rendering them useful vectors for introduction of nucleic acid into a cell lacking complementary genetic information enabling encapsidation (Mann et al., cell 33:153 (1983); Miller and Buttimore, Mol. Cell. Biol. 6:2895 (1986) (PA317, ATCC CRL9078). Packaging cell lines which contain amphotrophic packaging genes able to transduce cells of human and other species origin are preferred.

DNA vectors containing the inserted genes or coding sequences are introduced into cells using standard methods, such as electroporation, liposomal preparations, Ca-PH-DNA gels, DEAE-dextran, nucleic acid particle "guns" and other suitable methods.

In general, nucleic acid encoding the selected molecules is inserted by standard recombinant DNA methods into a vector containing appropriate transcription and translation control sequences, including initiation sequences operably linked to the gene sequence to result in expression of the recombinant genes in the recipient host. Operably linked refers to a juxtaposition wherein the components are in a relationship permitting them to function in their intended manner. For instance, a promoter is operably linked to a coding sequence if the promoter effects its transcription or expression.

The nucleic acid sequences encoding the proteins or protein fragments selected for expression in may be inserted in a single vector or in separate vectors. More than one gene encoding a selected polypeptide, or portion thereof, may be inserted into a single vector or in separate vectors.

Expression of recombinant genes of interest after introduction into APCs is confirmed by immunoassays or biological assays for functional activity of the protein product. For example, expression of introduced molecules into cells may be confirmed by detecting the binding of labeled antibodies to the cells using assays well known in the art such as FACS (Fluorescent Activated Cell Sorting) or ELISA (enzyme-linked immunoabsorbent assay).

Biological activity of the engineered cells can be verified, for example, in in vitro assays. The ability of the cells of the invention to function as desired, e.g. to bind to CTLA4 and to downmodulate an immune response may be tested using standard in vitro and/or in vivo assays.

VI. Pharmaceutical Compositions

CTLA4 antibodies or antigen binding portions thereof (including antibody or antibody binding portion toxic moiety-conjugates) of the invention can be incorporated into compositions, e.g., pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a CTLA4 protein or anti-CTLA4 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In one embodiment of the present invention a therapeutically effective amount of an antibody to a CTLA4 protein is administered to a subject. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays as described herein.

In one embodiment, a pharmaceutical composition for injection could be made up to contain 1 ml sterile buffered water, and 1 to 50 mg of antibody. A typical composition for intravenous infusion could be made up to contain 250 ml of sterile Ringer's solution, and 150 mg of antibody. Actual methods for preparing parenterally administrable compositions will be known or apparent to those skilled in the art and are described in more detail in, for example, Remington's Pharmaceutical Science, 15th ed., Mack Publishing Company, Easton, Pa. (1980), which is incorporated herein by reference. The compositions containing the present human-like antibodies or a cocktail thereof can be administered for prophylactic and/or therapeutic treatments. In therapeutic application, compositions are administered to a patient already suffering from a disease, in an amount sufficient to cure or at least partially arrest the disease and its complications. An amount adequate to accomplish this is defined as a "therapeutically effective dose." Amounts effective for this use will depend upon the severity of the infection and the general state of the patient's own immune system, but generally range from about 1 to about 200 mg of antibody per dose, with dosages of from 5 to 25 mg being more commonly used. It must be kept in mind that the materials of this invention may generally be employed in serious disease states, that is life-threatening or potentially life-threatening situations. In such cases, in view of the minimization of extraneous substances and the lower probability of "foreign substance" rejections which are achieved by the present human-like antibodies of this invention, it is possible and may be felt desirable by the treating physician to administer substantial excesses of these antibodies. In prophylactic applications, compositions containing the present antibodies or a cocktail thereof are administered to a patient not already in a disease state to enhance the patient's resistance. Such an amount is defined to be a "prophylactically effective dose." In this use, the precise amounts again depend upon the patient's state of health and general level of immunity, but generally range from 0.1 to 25 mg per dose, especially 0.5 to 2.5 mg per dose. A preferred prophylactic use is for the prevention of kidney transplant rejection. Single or multiple administrations of the compositions can be carried out with dose levels and pattern being selected by the treating physician. In any event, the pharmaceutical formulations should provide a quantity of the antibody(ies) of this invention sufficient to effectively treat the patient.

The pharmaceutical compositions can be included in a container, pack, or dispenser together with instructions for administration. Kits for practice of the instant invention are also provided. For example, such a diagnostic kit comprises an antibody reactive with CTLA4 conjugated to a toxic moiety. The kit can further comprise a means for administering the antibody conjugate, e.g., one or more syringes. The kit can come packaged with instructions for use.

VII. Uses and Methods of the Invention

The antibodies or antigen binding portions thereof described herein (including toxic moiety conjugates) can be used in one or more of the following methods of treatment, e.g., up- or down-modulating the immune response. Such methods involve contacting an antibody of the invention with a T cell. The step of contacting can be performed either in vitro or in vivo. In addition to the therapeutic methods described below, the antibodies of the instant invention can be used for research purposes, e.g., in staining for CTLA4 bearing cells, e.g., by forms of the antibodies which have been labeled with a detectable label, or by using a secondary antibody which is conjugated to a detectable label. In addition, in another embodiment, the subject antibodies can be used in methods of isolating CTLA4 bearing cells, as well as in methods of purifying CTLA4 to homogeneity, for example, using an affinity column.

A. Methods of Treatment:

The present invention provides for both prophylactic and therapeutic methods of treating a subject at risk of (or susceptible to) a disorder or having a disorder associated with aberrant or undesirable CTLA4 expression or activity.

1. Prophylactic Methods

In one aspect, the invention provides a method for preventing in a subject, a disease or condition associated with aberrant CTLA4 expression or activity or aberrant T cell activation, by administering to the subject an anti-CTLA4 antibody or conjugate thereof, or an agent which modulates CTLA4 polypeptide expression or at least one CTLA4 or T cell activity. Subjects at risk for a disease which is caused or contributed to by aberrant or undesirable CTLA4 expression or activity or undesirable T cell activation can be identified by, for example, any or a combination of diagnostic or prognostic assays known in the art. Administration of a prophylactic agent can occur prior to the manifestation of symptoms for which modulation of CTLA4 activity would be beneficial, such that a disease or disorder is prevented or, alternatively, delayed in its progression. Depending on the type of CTLA4 aberrance or condition various forms of anti-CTLA4 antibodies may be administered. For example, a soluble, monovalent form of an anti-CTLA4 antibody or a multivalent, cross-linked form of an activating or a blocking anti-CTLA4 antibody can be used for treating the subject. In addition, it is possible to target populations of CTLA4 bearing cells for elimination using an anti-CTLA4 antibody that has been conjugated to a toxic moiety to prevent or delay the progression of a disorder associated with overexpansion or overactivity of CTLA4-bearing cells.

2. Therapeutic Methods

Another aspect of the invention pertains to methods of modulating CTLA4 expression or activity for therapeutic purposes. CTLA4 has been demonstrated to transmit an inhibitory signal to immune cells upon binding to costimulatory molecules on antigen presenting cells. Accordingly, the activity and/or expression of CTLA4 as well as the interaction between CTLA4 and costimulatory molecules can be modulated in order to modulate the immune response.

Modulatory methods of the invention involve contacting a T cell with an antibody that recognizes CTLA4 or a toxic moiety conjugate thereof.

These antibodies can be administered in vitro (e.g., by contacting the cell with the agent) or, alternatively, in vivo (e.g., by administering the agent to a subject). As such, the present invention provides methods of treating an individual afflicted with a disease or disorder that would benefit from modulation of a CTLA4 protein activity, e.g., a disorder which would benefit from up or downmodulation of the immune response, or which is characterized by aberrant expression or activity of a CTLA4 protein or nucleic acid molecule. In one embodiment, the method involves administering an antibody, or combination of antibodies that modulates (e.g., upregulates or downregulates) CTLA4 expression or activity or T cell activity. Preferably, costimulation of T cells is modulated resulting in modulation of the immune response.

Stimulation of CTLA4 activity is desirable in situations in which CTLA4 is abnormally downregulated and/or in which increased CTLA4 activity is likely to have a beneficial effect. Likewise, inhibition of CTLA4 activity is desirable in situations in which CTLA4 is abnormally upregulated and/or in which decreased CTLA4 activity is likely to have a beneficial effect.

3. Downregulation of Immune Responses by Modulation of CTLA4

There are numerous means by which the inhibitory function of a CTLA4 polypeptide can be promoted to thereby downregulate immune responses. In one embodiment, an anti-CTLA4 activating antibody that acts as a CTLA4 agonist in soluble form is used to transmit a negative signal to a T cell via CTLA4.

In another embodiment, an anti-CTLA4 antibody of the invention is used in multivalent form, e.g., is presented on a bead or crosslinked with a second antibody that recognizes the anti-CTLA4 antibody such that CTLA4 molecules on the surface of a T cell are cross-linked.

The CTLA4 molecule is only present on activated T cells, therefore, anti-CTLA4 antibodies conjugated to toxic moieties are a means of targeting the destruction of activated T cells. In addition, an immune response can be downmodulated by the use of an anti-CTLA4 antibody conjugated to a toxic moiety molecule to selectively eliminate activated, CTLA4 bearing T cells. Downregulation can be in the form of inhibiting or blocking an immune response already in progress or may involve preventing the induction of an immune response. The functions of activated T cells can be inhibited by down-regulating immune cell responses or by inducing specific anergy in immune cells, or both.

In one embodiment of the invention, an antibody used to downmodulate a CTLA4 activity or a T cell activity is a bispecific antibody. For example, such an antibody can comprise a CTLA4 binding site and another binding site which targets a cell surface receptor on a T cell. For example, in one embodiment, such an antibody, in addition to comprising a CTLA4 binding site can further comprise a binding site which binds, e.g., to a T-cell antigen receptor in order to more efficiently target the molecule to a specific cell population. Antibodies that mimic interaction of CTLA4 with a costimulatory molecule (e.g., CTLA4 activating antibodies or multivalently presented antibodies) can be identified by their ability to inhibit immune cell proliferation and/or effector function or to induce anergy when needed to an in vitro assay. For example, cells can be cultured in the presence of an agent that stimulates signal transduction via an activating receptor. A number of art recognized readouts of cell activation can be employed to measure the ability of an antibody to transmit a negative signal, e.g., by measuring its effect on cell proliferation or T cell effector function (e.g., cytokine production) in the presence of the activating agent. The ability of a test agent to block this activation can be readily determined by measuring the ability of the agent to effect a decrease in proliferation or effector function being measured.

In one embodiment of the invention, tolerance is induced against specific antigens by co-administering an antigen with an anti-CTLA4 antibody. For example, tolerance can be induced to specific proteins (e.g., therapeutic proteins). In one embodiment, immune responses to allergens or foreign proteins to which an immune response is undesirable can be inhibited. For example, patients that receive Factor VIII frequently generate antibodies against this clotting factor. Co-administration of an inhibitory form of an anti-CTLA4 antibody or a toxic moiety conjugate thereof, in combination with recombinant factor VIII (or by physically linked to Factor VIII, e.g., by cross-linking) can result in downmodulation of the immune response.

Other immunomodulatory agents can be administered in combination with the subject antibodies or conjugates. Examples of other immunomodulating reagents include antibodies that block a costimulatory signal, (e.g., against CD28, ICOS), antibodies against other immune cell markers (e.g., against CD40, against CD40 ligand, or against cytokines), fusion proteins (e.g., CTLA4-Fc), and immunosuppressive drugs, (e.g., rapamycin, cyclosporine A or FK506).

Activating a CTLA4 inhibitory function (e.g., by stimulation of the negative signaling function of CTLA4 or targeting CTLA4 with an antibody conjugate) is useful to downmodulate the immune response, e.g., in situations of tissue, skin and organ transplantation, in graft-versus-host disease (GVHD), or in autoimmune diseases such as systemic lupus erythematosus, and multiple sclerosis. For example, blockage of immune cell function results in reduced tissue destruction in tissue transplantation. Typically, in tissue transplants, rejection of the transplant is initiated through its recognition as foreign by immune cells, followed by an immune reaction that destroys the transplant. The administration of an antibody which activates a CTLA4 molecule or an antibody-toxic moiety conjugate that binds to CTLA4, alone or in combination with another downmodulatory agent prior to or at the time of transplantation, can inhibit the immune response. Moreover, promotion of a CTLA4 inhibitory signal may also be sufficient to anergize the immune cells, thereby inducing tolerance in a subject. In one embodiment, anti-CTLA4 can induce long term tolerance in a subject and may avoid the necessity of repeated administration of these blocking reagents.

To achieve sufficient immunosuppression or tolerance in a subject, it may also be desirable to block the costimulatory function of other molecules. For example, it may be desirable to block the function of B7-1, B7-2, or B7-1 and B7-2 by administering a soluble form of a combination of peptides having an activity of each of these antigens or blocking antibodies against these antigens (separately or together in a single composition) prior to or at the time of transplantation. Alternatively, it may be desirable to promote inhibitory activity of CTLA4 and inhibit a costimulatory activity of B7-1 and/or B7-2. Other downmodulatory agents that can be used in connection with the downmodulatory methods of the invention include, for example, soluble forms of CTLA4, blocking antibodies against other immune cell markers or soluble forms of other receptor ligand pairs (e.g., agents that disrupt the interaction between CD40 and CD40 ligand (e.g., anti CD40 ligand antibodies)), antibodies against cytokines, or immunosuppressive drugs.

Activating a CTLA4 inhibitory function or targeting T cells with an antibody toxic moiety conjugate is also useful in treating autoimmune disease. Many autoimmune disorders are the result of inappropriate activation of immune cells that are reactive against self tissue and which promote the production of cytokines and autoantibodies involved in the pathology of the diseases. Preventing the activation of autoreactive immune cells may reduce or eliminate disease symptoms. Administration of CTLA4 activating antibodies that transmit a negative signal via CTLA4 or anti-CTLA4 toxic moiety conjugates is useful to inhibit immune cell activation and prevent production of autoantibodies or cytokines which may be involved in the disease process. Additionally, agents that promote an inhibitory function of CTLA4 can induce antigen-specific tolerance of autoreactive immune cells which can lead to long-term relief from the disease. The efficacy of reagents in preventing or alleviating autoimmune disorders can be determined using a number of well-characterized animal models of human autoimmune diseases. Examples include murine experimental autoimmune encephalitis, systemic lupus erythematosus in MRL/lpr/lpr mice or NZB hybrid mice, murine autoimmune collagen arthritis, diabetes mellitus in NOD mice and BB rats, and murine experimental myasthenia gravis (see Paul ed., *Fundamental Immunology*, Raven Press, New York, 1989, pp. 840–856).

Inhibition of immune cell activation is useful therapeutically in the treatment of allergy and allergic reactions, e.g., by inhibiting IgE production. An agent that promotes a CTLA4 inhibitory function or an anti-CTLA4 toxic moiety conjugate can be administered to an allergic subject to inhibit immune cell mediated allergic responses in the subject. Activating CTLA4 may also be useful in treating allergies. Stimulation of a CTLA4 inhibitory pathway can be accompanied by exposure to allergen in conjunction with appropriate MHC molecules. Allergic reactions can be systemic or local in nature, depending on the route of entry of the allergen and the pattern of deposition of IgE on mast cells or basophils. Thus, inhibition of immune cell mediated allergic responses can be effected locally or systemically by administration of an inhibitory form of an antibody that promotes an inhibitory function of CTLA4 or an anti-CTLA4-toxic moiety conjugate.

Inhibition of immune cell activation through stimulation of CTLA4 inhibitory activity may also be important therapeutically in viral infections of immune cells. For example, in the acquired immune deficiency syndrome (AIDS), viral replication is stimulated by immune cell activation. Stimulation of CTLA4 inhibitory function may result in inhibition of viral replication and thereby ameliorate the course of AIDS.

4. Upregulation of Immune Responses by Modulation of CTLA4

Blockage of an inhibitory activity of CTLA4 as a means of upregulating immune responses is also useful in therapy. There are numerous means by which the inhibitory function of a CTLA4 polypeptide can be blocked to thereby upregulate immune responses. In one embodiment, an anti-CTLA4 blocking antibody that blocks the interaction of CTLA4 with its naturally occurring ligand (e.g., CD80 and/or CD86) acts as a CTLA4 antagonist in soluble form and is used to inhibit the transmission of a negative signal to a T cell via CTLA4.

Upregulation of immune responses can be in the form of enhancing an existing immune response or eliciting an initial immune response. For example, enhancing an immune response by blocking CTLA4 inhibitory activity is useful in cases of infections with microbes, e.g., bacteria, viruses, or parasites. For example, in one embodiment, an antibody that inhibits the interaction of CTLA4 with a costimulatory molecule, e.g., a non-activating antibody against CTLA4, is therapeutically useful in situations where upregulation of antibody and cell-mediated responses, resulting in more rapid or thorough clearance of virus, would be beneficial. Examples include viral skin diseases such as Herpes or shingles, in which case such an agent can be delivered topically to the skin. In addition, systemic viral diseases such as influenza, the common cold, and encephalitis might be alleviated by the administration of such agents systemically.

In certain instances, it may be desirable to further administer other agents that upregulate immune responses, for example, forms of B7 family members that transduce signals via costimulatory receptors, in order further augment the immune response.

Alternatively, immune responses can be enhanced in an infected patient by removing immune cells from the patient, contacting immune cells in vitro with an antibody that inhibits transduction of an inhibitory signal via CTLA4, and reintroducing the in vitro stimulated immune cells into the patient.

Antibodies that inhibit transduction of an inhibitory signal via CTLA4 can be used prophylactically in vaccines against various polypeptides, e.g., polypeptides derived from pathogens. Immunity against a pathogen, e.g., a virus, can be induced by vaccinating with a viral protein along with a an antibody that inhibits transduction of an inhibitory signal via CTLA4 in an appropriate adjuvant.

In another embodiment, the immune response can be stimulated by inhibiting signaling via an inhibitory receptor that binds to a costimulatory molecule, e.g., CTLA4, such that preexisting tolerance is overcome. For example, immune responses against antigens to which a subject cannot mount a significant immune response, e.g., tumor specific antigens can be induced by administering an agent that inhibits the inhibitory activity of CTLA4. CTLA4 antagonists can be used as adjuvants to boost responses to foreign antigens in the process of active immunization.

In one embodiment, immune cells are obtained from a subject and cultured ex vivo to in the presence of an antibody that that inhibits a CTLA4 inhibitory signal, to expand the population of immune cells. In a further embodiment the immune cells are then administered to a subject. Immune cells can be stimulated to proliferate in vitro by, for example, providing to the immune cells a primary activation signal and a costimulatory signal, as is known in the art. The costimulatory molecule can be, e.g., soluble, attached to a cell membrane or attached to a solid surface, such as a bead. Antibodies that inhibit signaling via CTLA4 can also be used to costimulate proliferation of immune cells. In one embodiment immune cells are cultured ex vivo according to the method described in PCT Application No. WO 94/29436.

VIII. Administration of CTLA4 Modulating Agents

CTLA4 modulating agents (e.g., stimulatory and inhibitory antibodies or antigen binding portions thereof as well as antibody or antigen-binding portions thereof conjugated to toxic moieties) of the invention are administered to subjects in a biologically compatible form suitable for pharmaceutical administration in vivo to either enhance or suppress T cell mediated immune response. By "biologically compatible form suitable for administration in vivo" is meant a form of the protein to be administered in which any toxic effects are outweighed by the therapeutic effects of the protein. The term subject is intended to include living organisms in which an immune response can be elicited, e.g., mammals. Examples of subjects include humans, horses, domesticated farm animals, exotic animals, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic compositions of the present invention is defined as an amount effective, at dosages and for periods of time necessary to achieve the desired result. For example, a therapeutically active amount of a CTLA4 antibody may vary according to factors such as the disease state, age, sex, and weight of the individual, and the ability of peptide to elicit a desired response in the individual. Dosage regima may be adjusted to provide the optimum therapeutic response. For example, several divided doses may be administered daily or the dose may be proportionally reduced as indicated by the exigencies of the therapeutic situation.

The anti-CTLA4 modulating agent (e.g., stimulatory or inhibitory antibody) may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound. For example, to administer CTLA4 modulating agent by other than parenteral administration, it may be necessary to coat the peptide with, or co-administer the peptide with, a material to prevent its inactivation.

A CTLA4 modulating agent may be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Other examples of adjuvants contemplated herein include alum, resorcinols, non-ionic surfactants such as polyoxyethylene oleyl ether and n-hexadecyl polyethylene ether, products derived from bacteria (or attenuated forms of pathogens). Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) *J. Neuroimmunol.* 7:27).

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (e.g., a CTLA4 modulating agent) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., peptide) plus any additional desired ingredient from a previously sterile-filtered solution thereof.

When the active compound is suitably protected, as described above, the protein may be orally administered, for example, with an inert diluent or an assimilable edible carrier. As used herein "pharmaceutically acceptable carrier" includes solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Antibodies of the present invention can further find a wide variety of utilities in vitro. By way of example, the antibodies can be utilized for T-cell typing, for isolating specific IL-2 receptor bearing cells or fragments of the receptor, for vaccine preparation, or the like. The effectiveness of an agent determined by a screening assay to decrease or downregulate CTLA4 activity or T cell activity (or immune responses generally) can be monitored in clinical trials of subjects.

In one embodiment genes, whose expression is regulated by modulation of a costimulatory pathway or by modulation of CTLA4 specifically, can be used as indicators of modulation of CTLA4 activity can be identified. Thus, to study the effect of the subject antibodies, for example, in a clinical trial, T cells can be isolated and RNA prepared and analyzed for the levels of expression of genes indicative of T cell activation (e.g., that are modulated upon blocking a CTLA4 inhibitory signal) or T cell inhibition (e.g., that are modulated upon transducing a CTLA4 inhibitory signal), respectively. The levels of gene expression (i. e., a gene expression pattern) can be quantified by Northern blot analysis or RT-PCR, as described herein, or alternatively by measuring the amount of protein produced, by one of the methods as described herein, or by measuring the levels of activity of CTLA4 or other genes. In this way, the gene expression pattern can serve as a marker, indicative of the physiological response of the cells to the agent. Accordingly, this response state may be determined before, and at various points during treatment of the individual with the agent. In a preferred embodiment, the present invention provides a method for monitoring the effectiveness of treatment of a subject with an antibody or toxic moiety conjugate by measuring the effect of the antibody or toxic moiety conjugate on the immune response, or on T cell activation or T cell numbers specifically. For example, standard methodologies can be used to assay, e.g., T cell proliferation, cytokine production, numbers of activated T cells, antibody production, or delayed type hypersensitivity. In addition or alternatively, improvement in a specific condition for which treatment is being given can be monitored.

This invention is further illustrated by the following examples which should not be construed as limiting. The contents of all references, patents, and published patent applications cited throughout this application, as well as the Figures and the Sequence Listing are incorporated herein by reference.

EXAMPLES

Example 1

Generation of Anti-CTLA4 antibodies

A group of 5 mice (Jackson Labs, Maine) were injected with 2 µg cDNA encoding the extracellular domain of rhuCTLA4. Purified plasma cDNA was precipitated onto gold beads to a concentration of 1 µg cDNA/0.5 mg gold. The gold beads and precipitated cDNA were delivered, monthly in two non-overlapping shots, intradermally in the abdomen of approximately 11 week old female BALB/c mice using a Hellos charged gene. These animal were immunized every four weeks and spleens were removed from the animals.

Spleens were processed to obtain a lymphocyte suspension and the resulting suspension were fused with the myeloma cell line 653/P3 using 50% (w/v) polyetheylene glycol 1500 (Boehringer Mannheim) by an established procedure (Oi & Herzenberg, 1980 in Selected Methods in Cellular Immunology, B. Mishel & S. Schiigi, eds., W. J. Freeman Co., San Francisco, Calif., p351). The fused cells were plated in 96-well microtiter plates at a density of $2\times10^5$ cells/well and after 24 hours were subjected to HAT selection (Littlefield, J. W. (1964) *Science* 145:709).

Hybridoma cells secreting putative anti-CTLA4 antibodies were identified by solid and solution phase ELISA and by intracellular and extracellular staining by flow cytometry on CHO cells expressing a gpi-anchored form of CTLA4 and activated T cells. Cross reactivity was assessed using cyno PHA blasts. Epitope mapping was done by flow cytometry and ELISA, and affinity determinations measured by Biacore. Wells containing hybridoma positive for the above assays were expanded for further study. These cultures remained stable when expanded and cell lines were cloned by limiting dilution and cryopreserved.

The isotype of the Mabs were determined by solid phase ELISA. Purified rhCTLA4IgG1Fc was coated onto 96-well microtiter plates, antibody added and detected by different isotype-specific biotin-conjugated goat anti-mouse immunoglobulins (Zymed). Streptavidin conjugated with horseradish peroxidase (HRP) was added and specifically bound enzyme was measured using a calorimetric substrate. Antibodies 25, 26, 27, 29, 33, 34, 35, 36, or 38 were identified. The results of this solid phase assay demonstrate that all antibodies tested were of the IgG1 isotype. Antibody 26 was subcloned and is also referred to as antibody 26B.

Example 2

Anti-CTLA4 antibodies varied in their ability to inhibit the binding of CTLA4 to CD80/CD86.

Figure 1B:
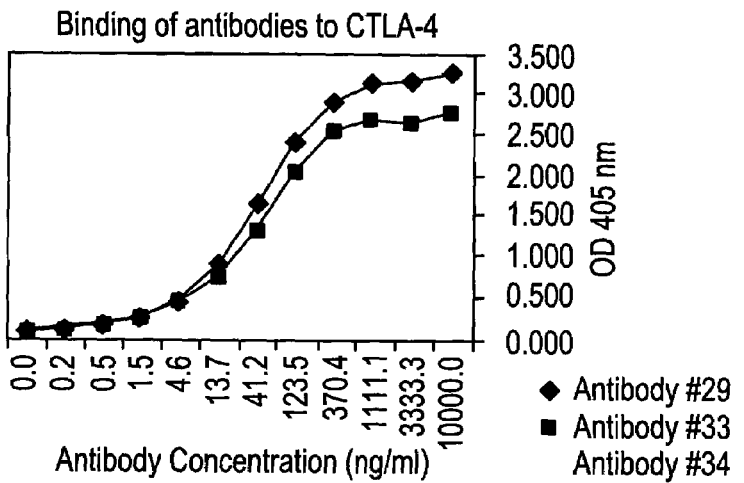
Figure 1C:
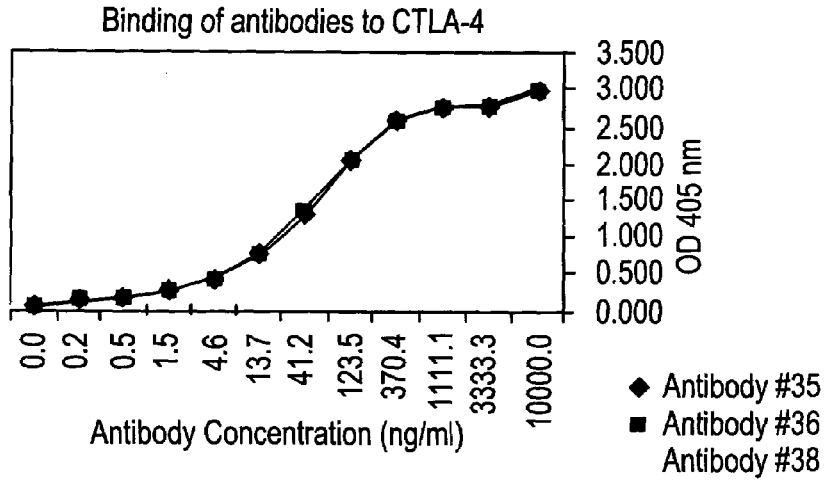

ELISA plates were incubated with 10 ug/ml human CTLA4-Ig overnight. Plates were washed with PBS/1% BSA and incubated with serial dilutions of primary antibody for 2 hrs at room temperature (RT). After washing, saturating concentrations of AP-conjugated goat anti-mouse antibody were added, and incubated for 1 hr at RT. Unbound goat antibodies were washed using PBS/1% BSA. The assay was developed using ABTS. FIGS. 1A–1C illustrates that each antibody in the panel of nine antibodies tested binds to CTLA4. The data are expressed as OD 405 absorbance values.

Figure 1D:
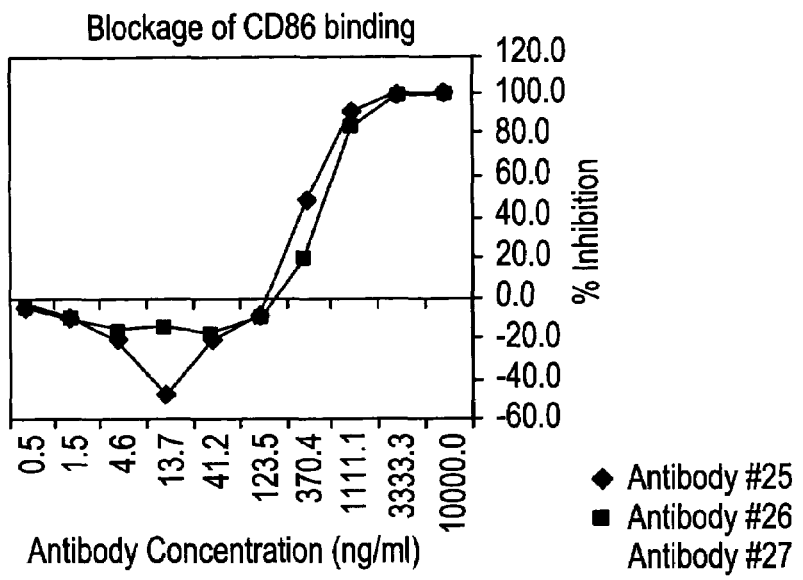
FIGS. 1D–1F illustrate the ability of the various antibodies to block binding of CTLA4 to CD86.
Figure 1E:
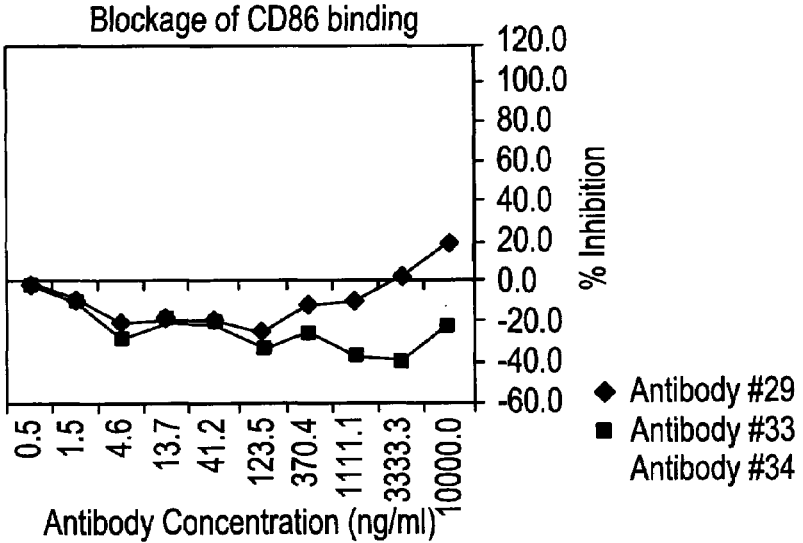
Figure 1F:
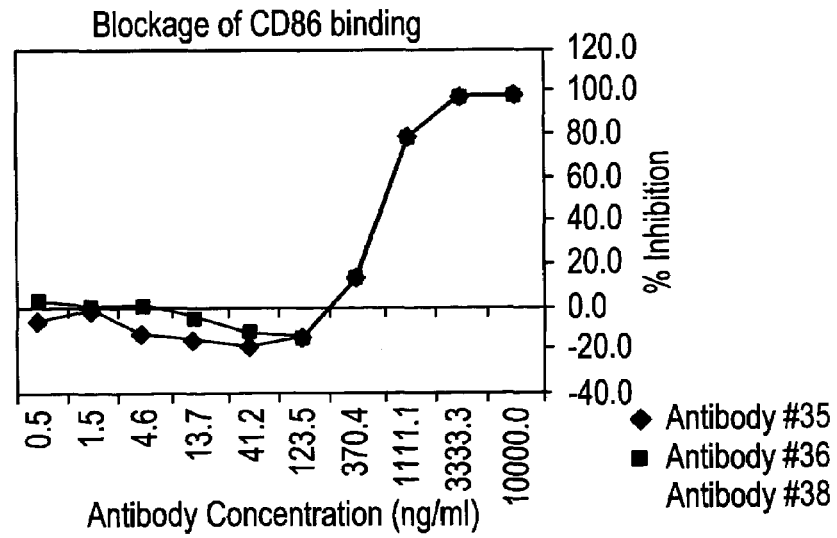
Figure 1G:
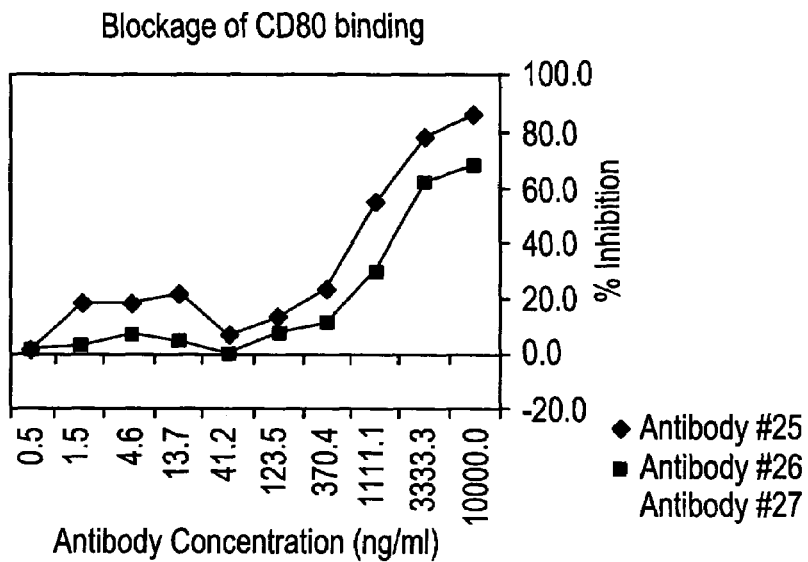
FIGS. 1G–1I illustrate the ability of the various antibodies to block binding of CTLA4 to CD80.
Figure 1H:
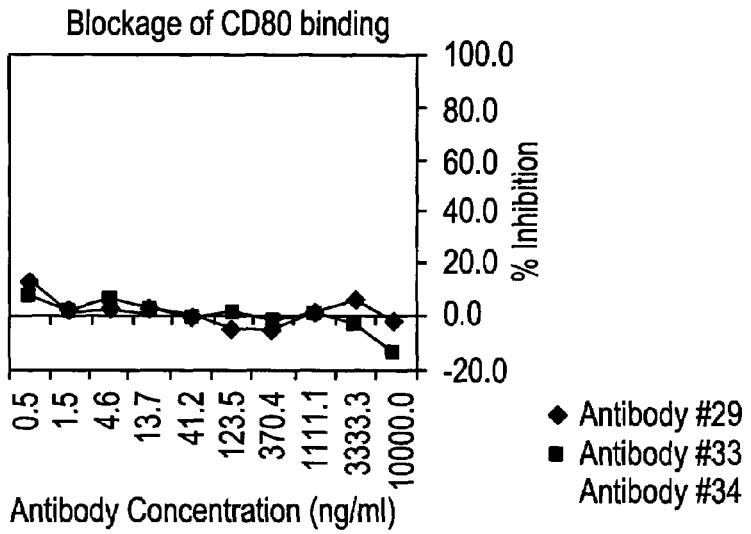
Figure 1I:
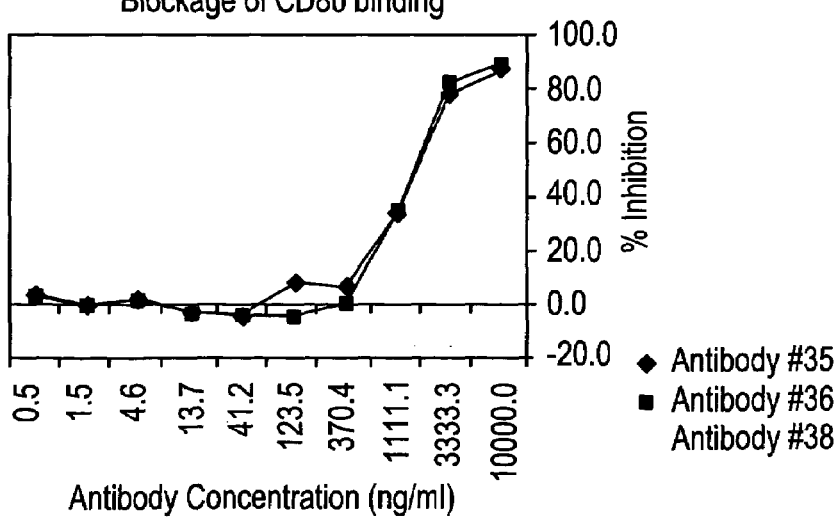

Inhibition assays were performed to assess the ability of these antibodies to block binding of CD80 and CD86 to CTLA4. ELISA were performed as described above with modifications. After incubation with primary antibody for 2 hr at RT, a fixed concentration (0.66 ug/ml) of biotin-conjugated CD80-Ig or CD86-Ig was added and further incubated for 1 hr at RT. After washing, saturating concentrations of neutravidin-AP were added, and incubated for 1 hr at RT. Unbound neutravidin-AP was washed using PBS/1% BSA. The assay was developed using ABTS. The percent inhibition is depicted on the Y axis. The results for inhibition of CD86 binding are shown in FIGS. 1D–1F and the results for CD80 binding are shown in FIGS. 1G–1I. These data illustrate that antibodies 29 and 33 failed to block the binding of CTLA4 to CD80 and CD86.

Example 3

Anti-hCTLA4 antibodies could be grouped based on their recognition of three distinct sites on the CTLA4 molecule.

A panel of CTLA4-Ig mutant molecules was generated by site-directed mutagenesis. Based on NMRI structure of CTLA4 (Metzler et al. *Nature Structural Biology* (1997) 4:527), 11 residues were selected for mutagenesis and substituted with alanine. Mutant proteins were transiently expressed on CHO cells and supernatants harvested at 48 hrs. Supernatants containing CTLA4 mutant molecules were quantitated and standardized by ELISA. Plates coated with 10 ug/ml antibody (25, 26, or 29) were incubated with supernatants containing approximately 0.5 ug/ml mutant CTLA4 molecules. After incubation for 2 hrs at RT, plates were washed and incubated for 1 hr with AP-conjugated goat anti-human Fc specific IgG. The assay was developed as described above.

Figure 2A:
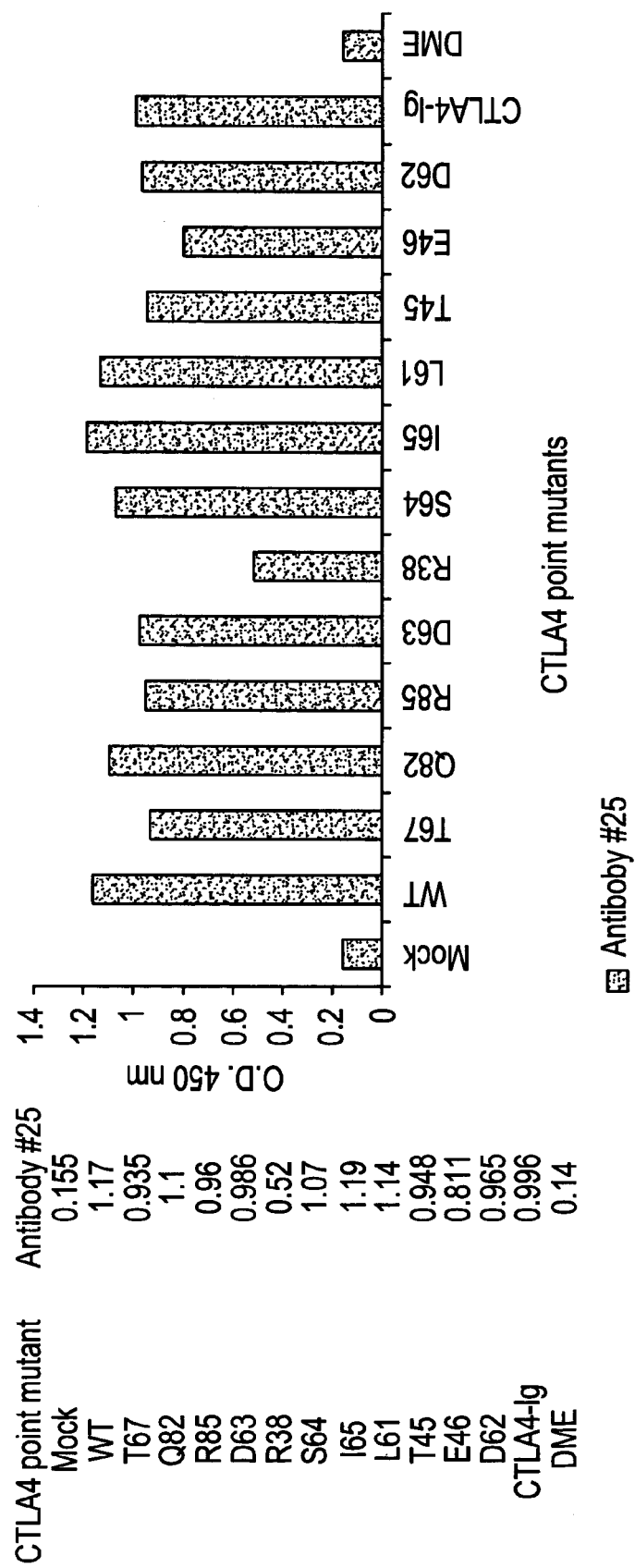
FIGS. 2A–2C illustrate the effect of different mutations introduced into the human CTLA4 amino acid sequence on the ability of the various anti-CTLA4 antibodies to bind to CTLA4. Antibody number 25 is shown in FIG. 2A. Antibody number 26 is shown in FIG. 2B. Antibody number 29 is shown in FIG. 2C.
Figure 2B:
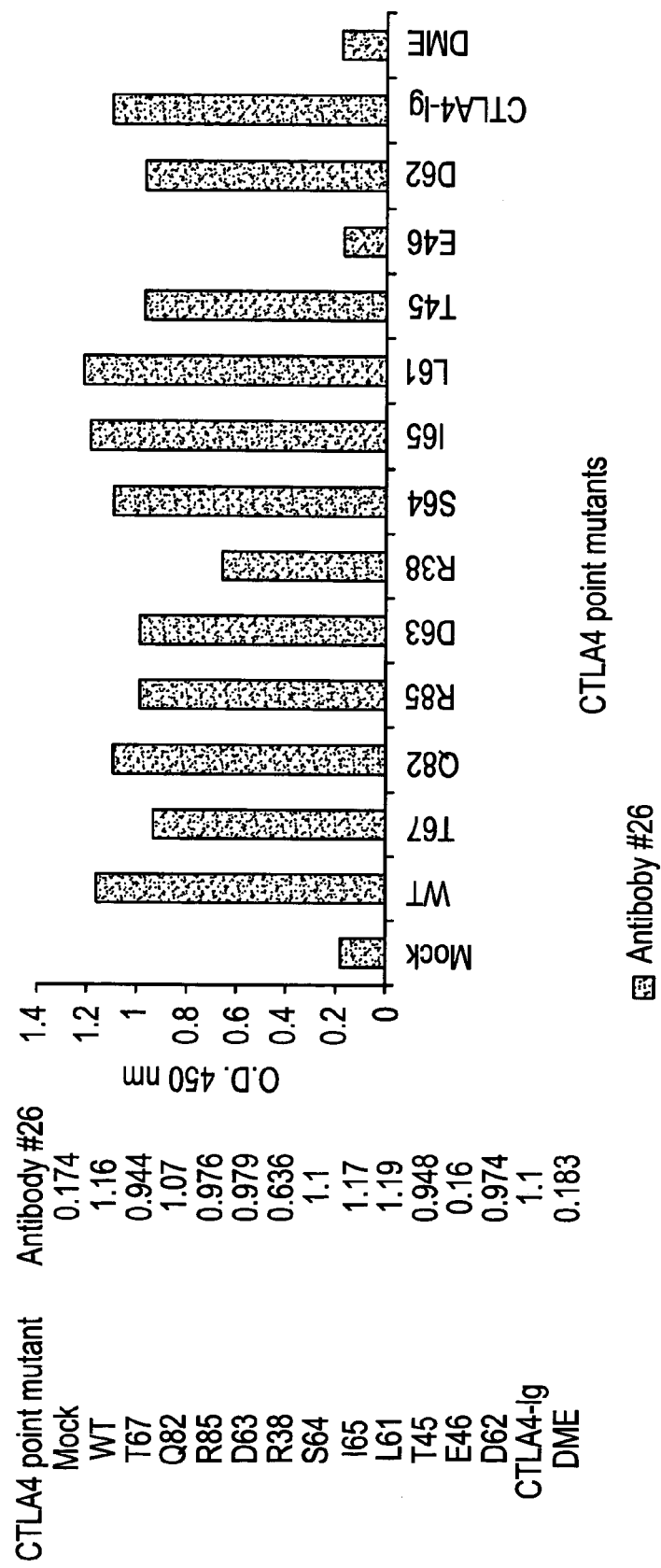
Figure 2C:
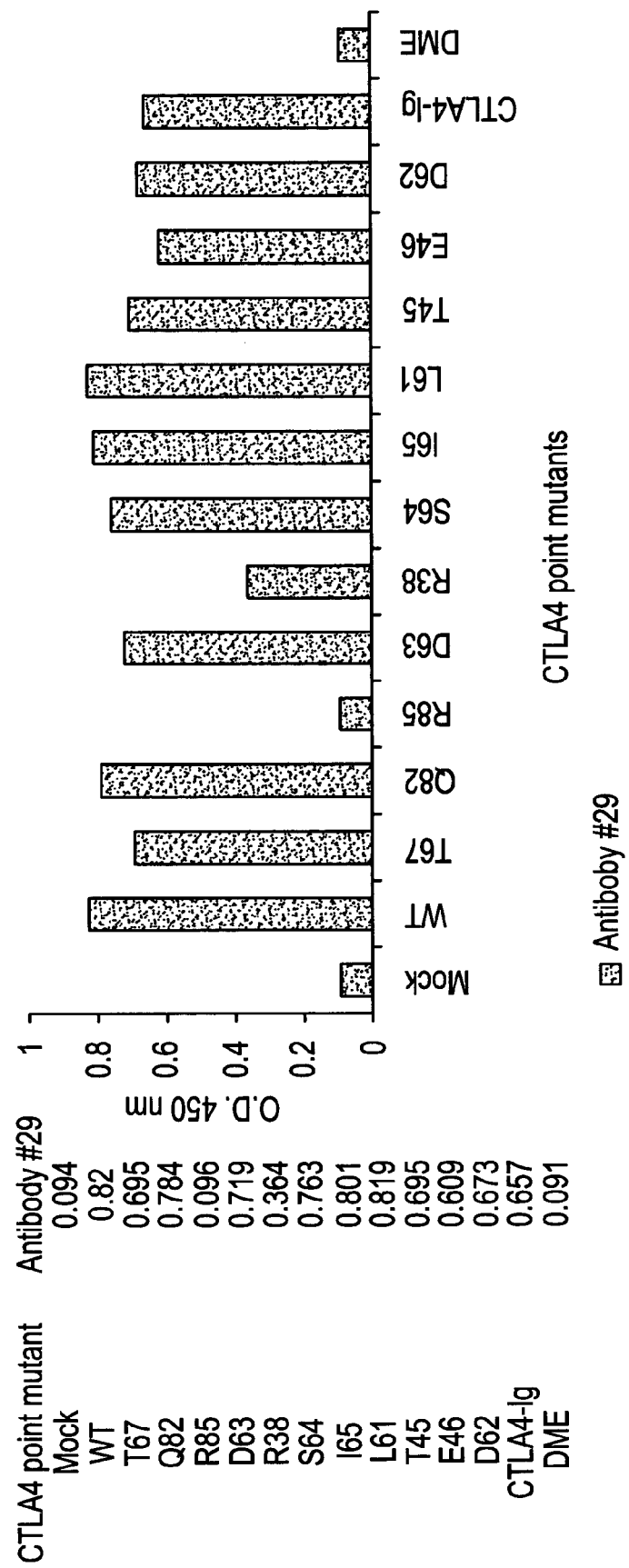

The data shown in FIG. 2 illustrate that the binding of anti-hCTLA4 antibodies is affected differently by different mutations introduced in the CTLA4 molecule. Optical density readings above background are indicative of antibody binding to the CTLA4 molecules bound to the plates. Antibodies 25, 26, and 29 are representative of antibodies with binding sites identified by the 9 antibodies. Substitution of alanine (A) for glutamic acid (E) at position 46 (position 83 of SEQ ID NO:2 which includes the signal sequence shown in amino acids 1–37 of SEQ ID NO:2) drastically affects binding of antibody 26, 27, 34, 35, 36, and 38. In contrast, the same substitution has little, if any, effect on antibodies 29, and 33. The binding of antibodies 29 and 33 to CTLA4, however, is affected by a substitution of alanine for arginine at position 85 (amino acid 120 of SEQ ID NO:2). Antibody 25 is affected by none of the mutations introduced. It has been previously demonstrated that substitutions introduced at position 46 also affect CD80 and CD86 binding to CTLA4 (Metzler et al. (1997) *Nat. Structural Biol.* 4:527). Thus, some of the antibodies described in this panel (those affected by the substitution at position 46, i.e., antibody numbers 26, 27, 34, 35, 36, and 38) bind to CTLA4 at a site in spatial proximity to the site of CD80/CD86 binding.

Example 4

CTLA4 engagement results in decreased T cell responses

The effects of cross-linked forms of antibodies to CTLA4 on proliferation and IL-2 production in T cells from two donors was tested.

Figure 3A:
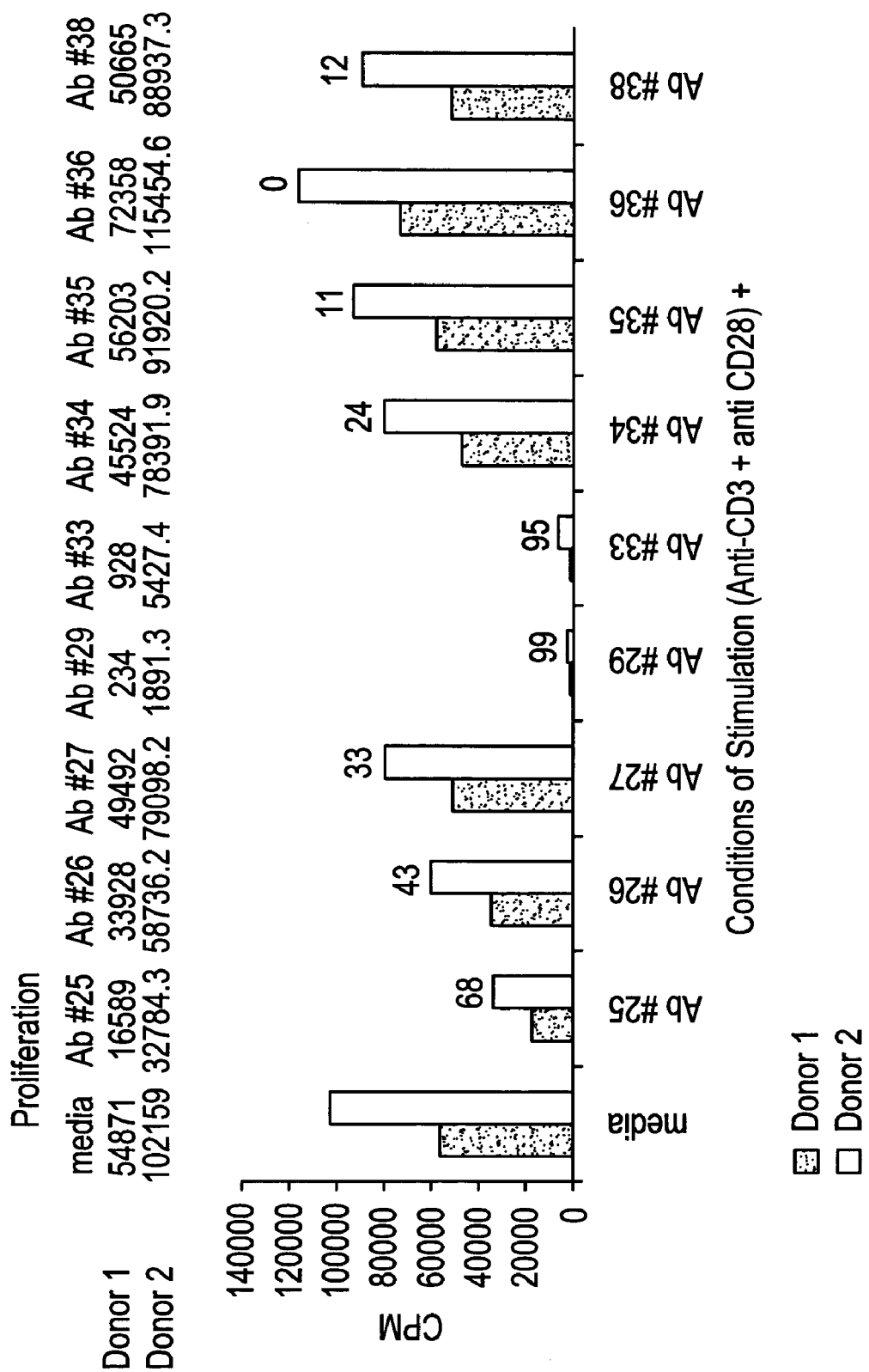
FIGS. 3A–3B illustrate the effect of cross-linked forms of anti-CTLA4 antibody on T cell proliferation and IL-2 production. Proliferation of primary T cells is shown in FIG. 3A, and IL-2 production by Jurkat cells is shown in FIG. 3B. The T cells were stimulated by anti-CD3+anti-CD28.

CD4+ T cells ($2.5 \times 10^4$ cells/well) were stimulated with tosyl-beads coated with anti-hCD3 +/− anti-CTLA4. After 72 hours, proliferation was determined by 3H-thymidine incorporation. Incorporated radioactivity was determined using a LKB 1205 plate reader. In panel A, numbers on top of the bars indicate percent inhibition in proliferative response relative to cells stimulated in the absence of anti-CTLA5 (media). As shown in FIG. 3A, most of the antibodies tested, with the exception of antibody number 36, resulted in decreased T cell proliferation.

Figure 3B:
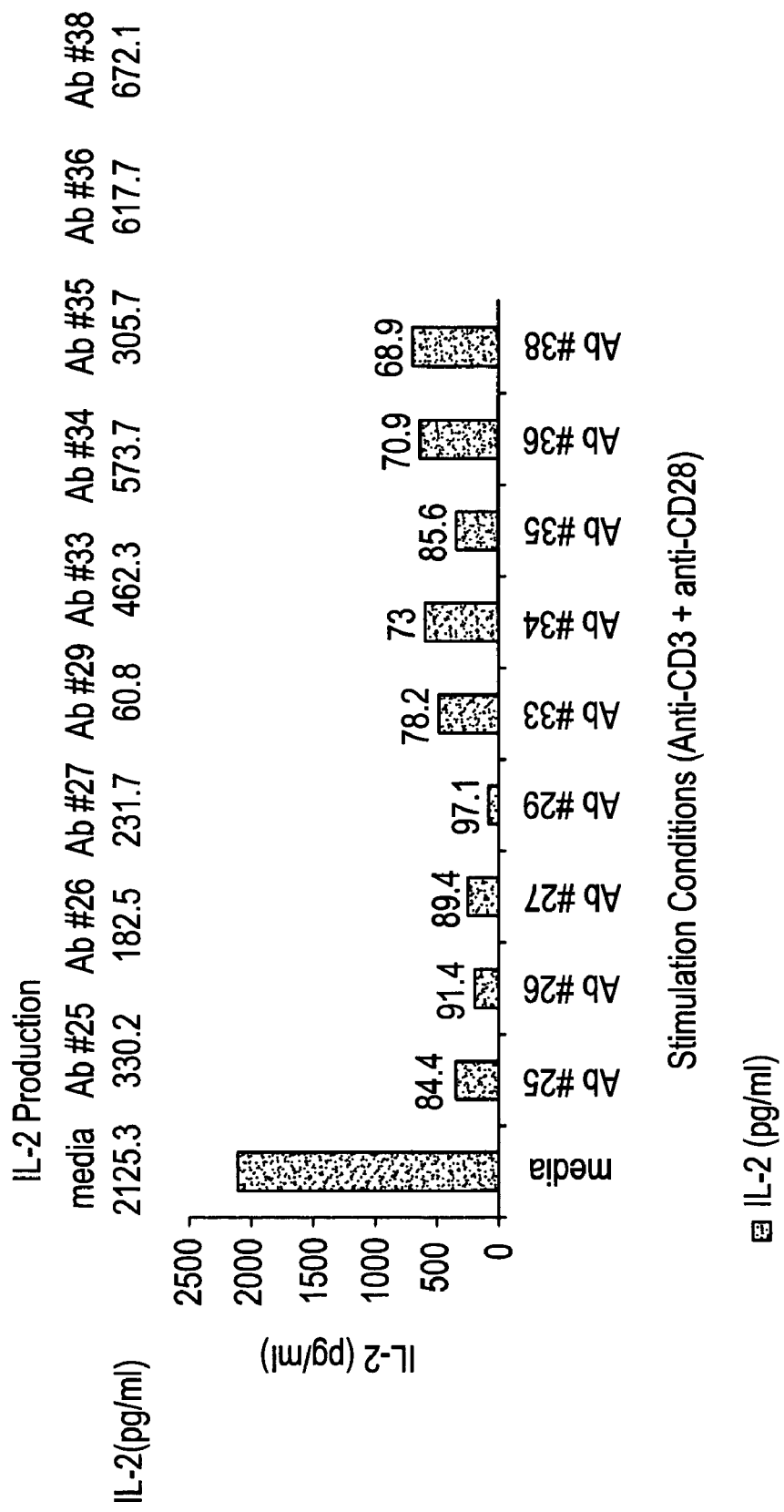

Jurkat T cells expressing hCTLA4 were stimulated with tosyl beads coated with anti-hCD3 +/− anti-CTLA4 in the presence of soluble anti-hCD28 antibody. Supernatants were harvested at 72 h and IL-2 production assessed using a commercially available hIL-2 ELISA kit (R&D Systems, MA). Numbers on the top of bars indicate percent inhibition relative to cells stimulated in the absence of anti-CTLA4 (media). As shown in FIG. 3B, all of the antibodies tested resulted in reduced IL-2 production by T cells in this assay.

Example 5

Blockage of CTLA4 engagement of CD80/CD86 by antibody number 26 results in enhanced proliferation and IL-2 production.

Mixed lymphocyte reactions (MLR) were performed using CD4+ T cells ($2.5 \times 10^4$ cells/well) as responders and an EBV-lymphoblastoid cell line ($2.5 \times 10^4$ cells/well as stimulators. Soluble antibody 26 or an IgG1 control antibody were added at various concentrations at initiation of the culture. After 5 days, proliferation was determined by $^3$H-thymidine incorporation. Incorporated radioactivity was determined using an LKB 1205 plate reader. FIG. 4A shows that addition of antibody number 26 to cultures resulted in levels of proliferation higher than those observed with control antibody. Antibody 26 was the only anti-CTLA4 antibody in the panel that was found to enhance proliferation of primary T cells.

Figure 4B:
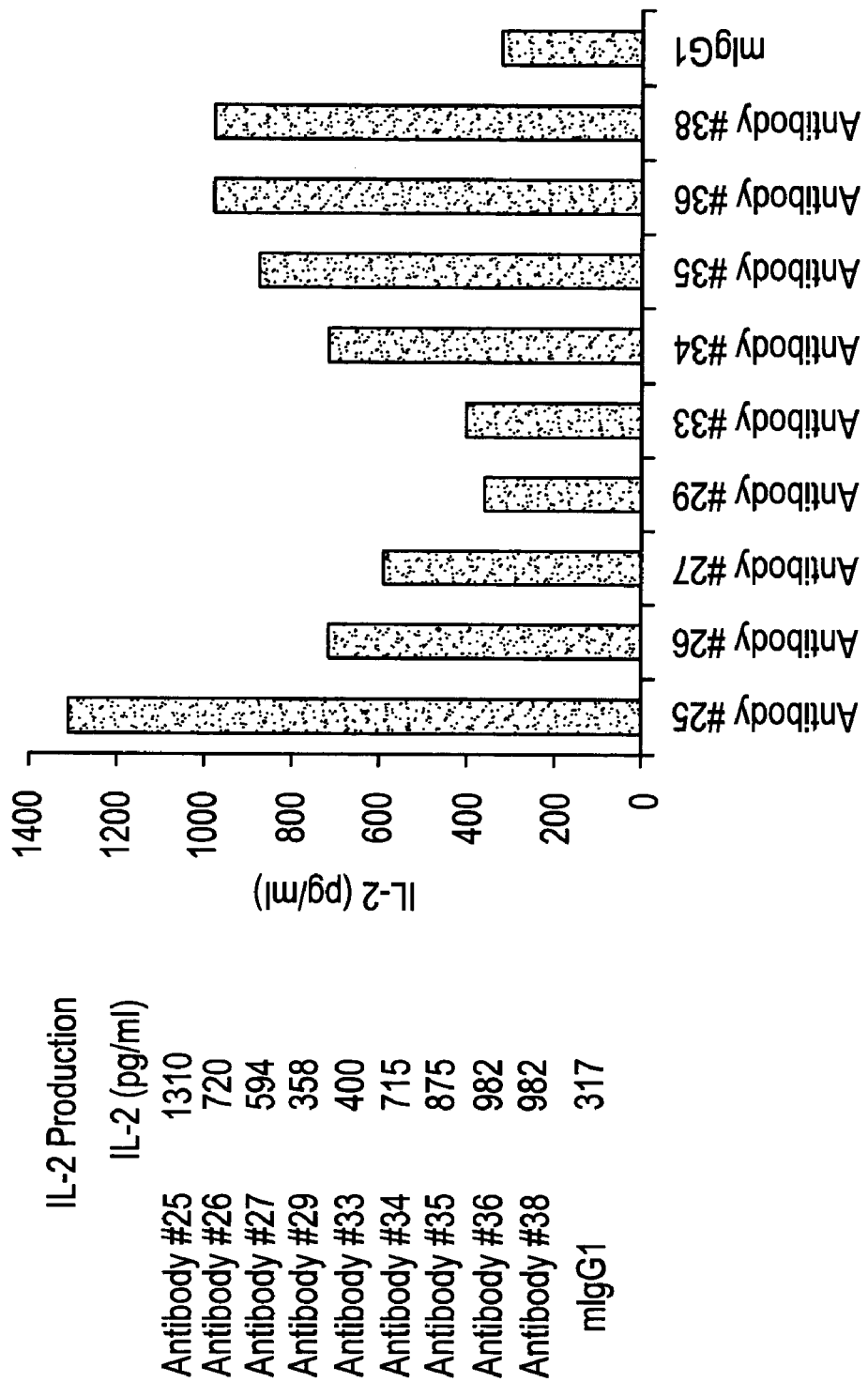
Figure 6A:
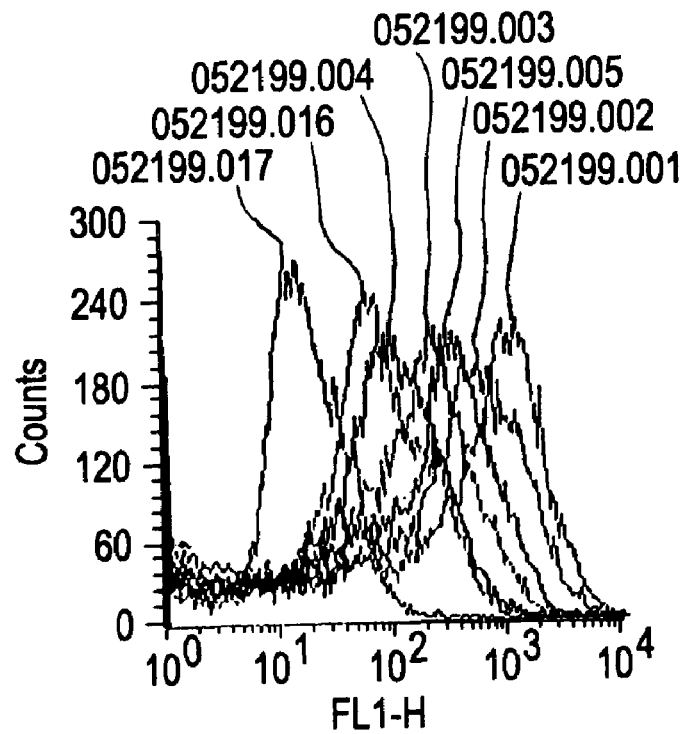
FIGS. 6A–6C illustrate a FACS competition assay using FITC-labeled mouse anti-CTLA4 in combination with varying amounts of either cold mouse anti-CTLA4 or humanized anti-CTLA4 IgG1.
Figure 6B:
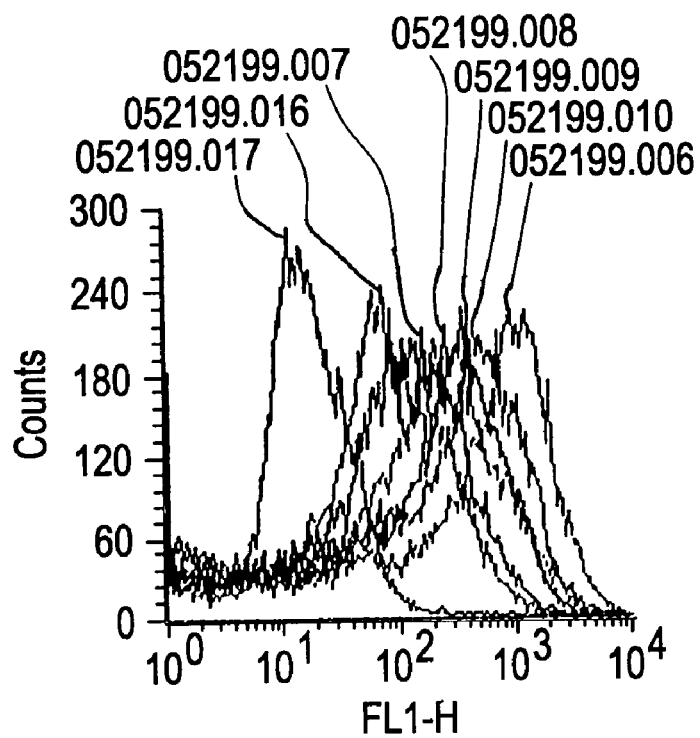
Figure 6C:
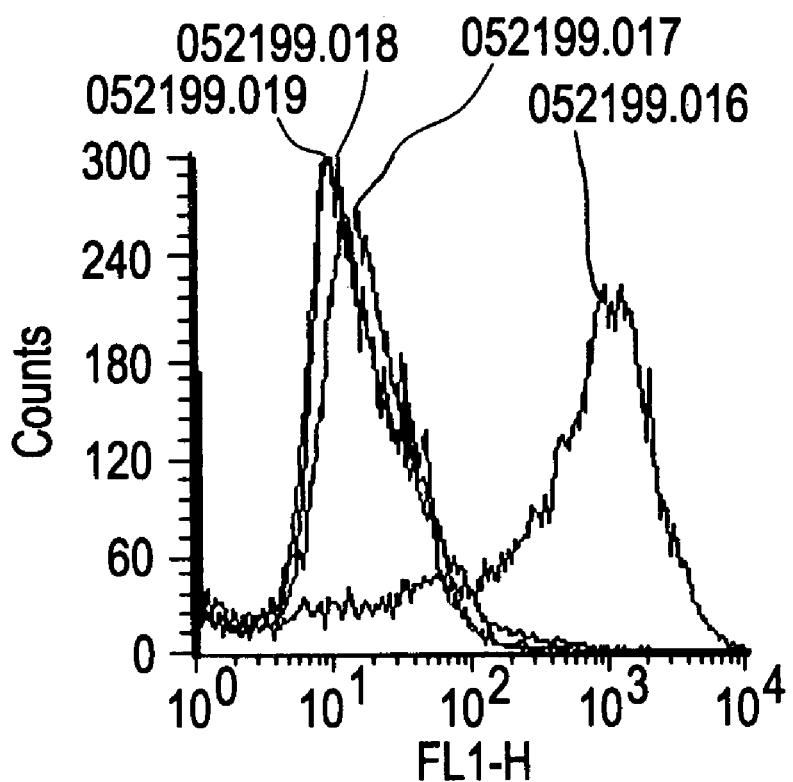
Figure 7A:
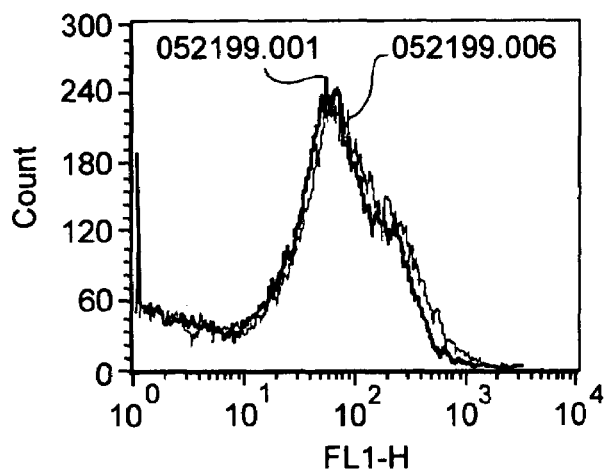
FIGS. 7A–7E show an alignment of histograms of cold competitors (mouse anti-CTLA4, humanized anti-CTLA4 IgG1) with the same concentrations to compare relative binding affinities.
Figure 7B:
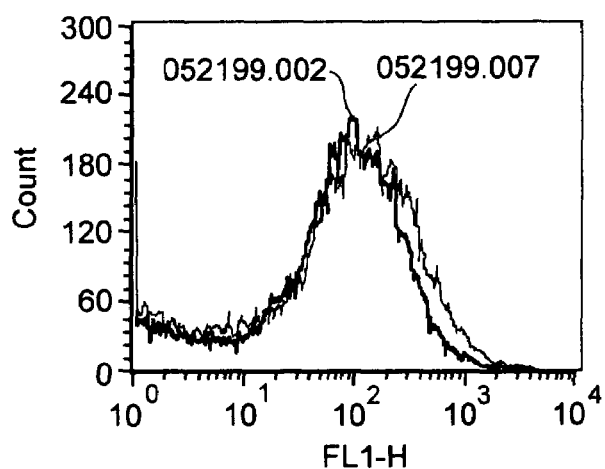
Figure 7C:
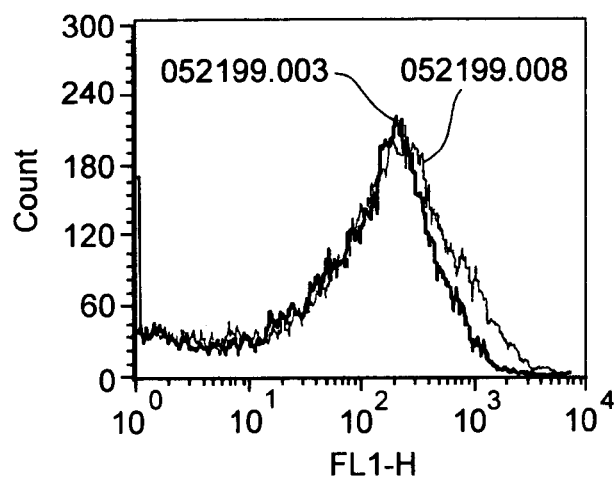
Figure 7D:
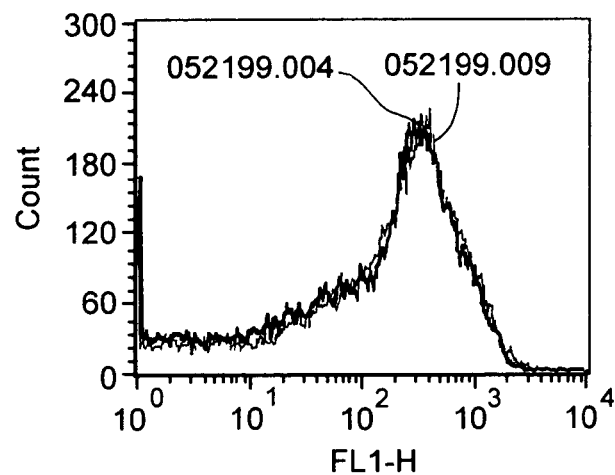
Figure 7E:
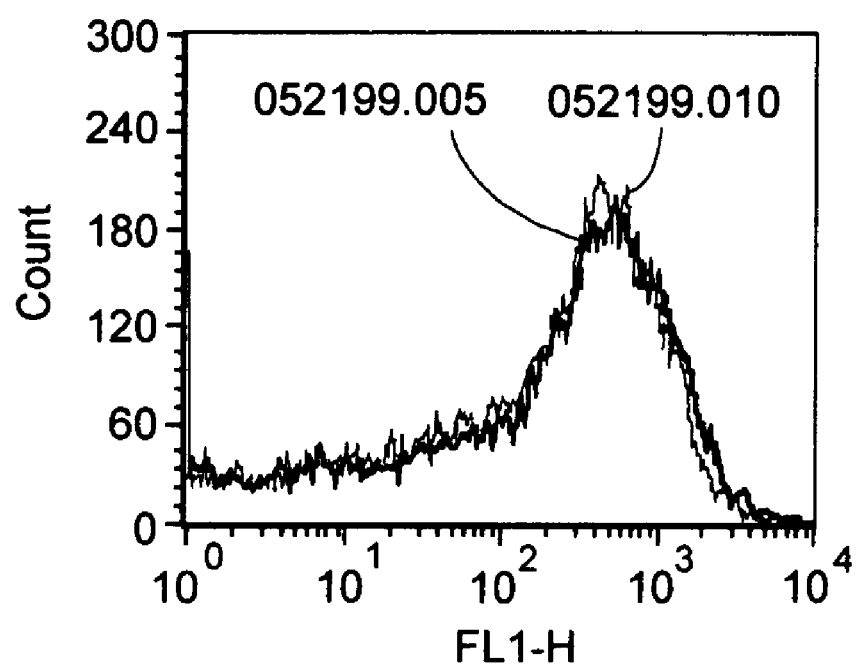
Figure 8A:
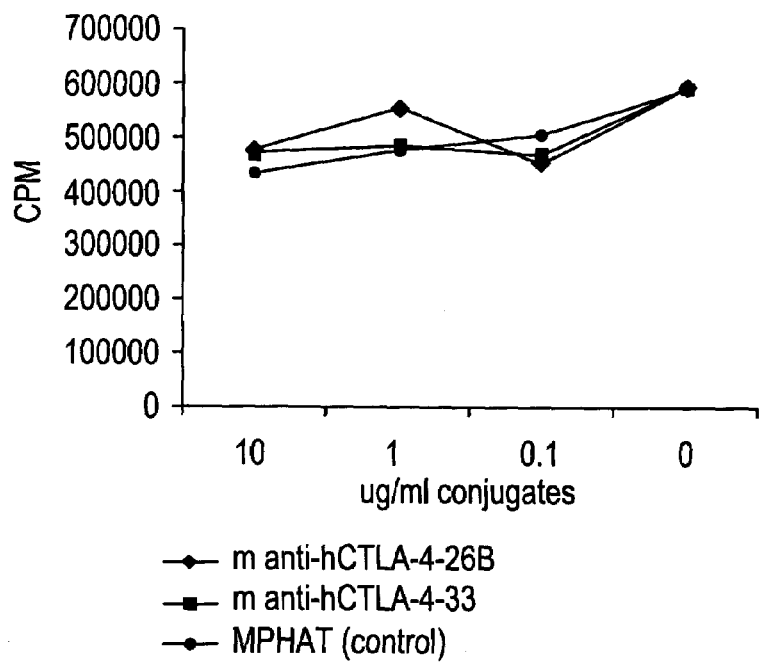
FIGS. 8A–8B illustrate the ability of toxic moiety-conjugated antibodies that recognize CTLA4 to inhibit the proliferation of CTLA4-bearing Jurkat cells (FIG. 8B). These antibodies do not inhibit the proliferation of Jurkat cells which are CTLA4 negative (FIG. 8A).
Figure 8B:
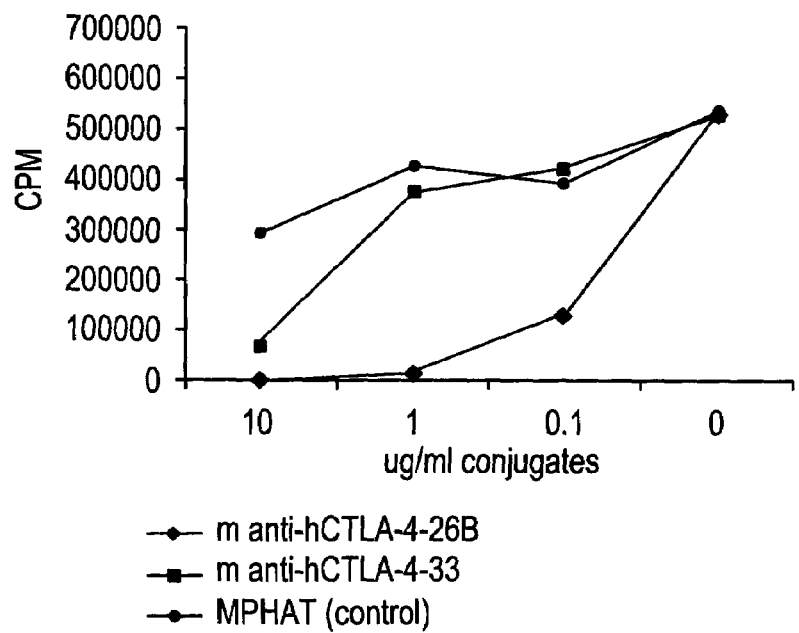

The effect of soluble forms of the other anti-CTLA4 antibodies on IL-2 production was also determined. Jurkat T cells were transfected with hCTLA4 ($10^6$ cells/ml) were stimulated with latex beads coated with anti-h CD3+ CD86-Ig in the presence of absence of soluble anti-CTLA4 antibody or IgG control. Supernatants were harvested at 72 hours and IL-2 production was assessed using a commercially available hIL-2 ELISA kit (R&D Systems, MA). FIG. 4B shows the levels of IL-2 produced by these cultures in the presence of the various antibodies.

Example 6

Nucleotide and amino acid sequence of heavy ($V_H$) and light ($V_k$) variable regions of antibody #26.

Total RNA was extracted from 6CTLA4/1.1.1.6 cells following the TRIzol protocol (Life Technologies), followed by cDNA synthesis and dG-tailing (Co et al. (1992) *J. Immunol.* 148:1149–1154). The resulting cDNA was used as a template and specific primers annealing to the polyG tail and the constant region of either the heavy chain or light chain gene were used to amplify the heavy and light chain variable regions using PCR. The PCR product (~450–500 bp) was gel-purified (Geneclean II kit, BIO101) and subjected to EcoRI and HindIII digestion. Following this, the PCR fragments for VL and VH were subcloned into pUC19 vector digested with the same enzymes aforementioned. The cloned regions were sequenced. Multiple clones for each of the VH and VL genes were sequenced. The cloning and sequencing of the V genes were repeated independently to confirm and ensure accuracy of the determined sequences. These sequences were submitted for computer modeling.

The partial nucleotide sequence of the heavy chain of #26, beginning at the 5' end of the ORF and extending through the variable region, is shown below:

(A)  VH (6CTLA4/1.1.1.6, VH):                                    (SEQ ID NO:3)

ATGGCTGTCCTGGTGCTGTTCCTCTGCCTGGTTGCATTTCCAAGCTGTGTCCTGTCCCAG

GTGCAGCTGAAGGAGTCAGGACCTGGCCTGGTGGCGCCCTCACAGAGCCTGTCCATCACT

TGCACTGTCTCTGGGTTTTCATTAACCAGCTATGGTGTATATTGGGTTCGCCAGCCTCCA

GGAAAGGGTCTGGAGTGGCTGGGAGTAATATAGGGCTGGTGGAACCACAAATTATAATTC

GGCTCTATGTCCAGACTGAGCATCAGCAAAGACAACTCCAAGAGCCAAGTTTTCTTAAAA

ATGAGCAGTCTGCAAACTGATGACACAGCCATGTACTACTGTGCCAGGGGCCCCCCGCAC

GCTATGATGAAGAGAGGCTATGCTATGGACTACTGGGGACAAGGAACCTCAGTCATCGTC

TCCTCA

Vk (6CTLA4/1.1.1.6, Vk):                                    (SEQ ID NO:5)

ATGGATTTTCAAGTGCAGATTTTCAGCTTCCTGCTAATCAGTGCCTCAGTCATACTGTCC

AGAGGACAAAATGTTCTCACCCAGTCTCCAGCAATCATGCCTGCATCTCCAGGGGAGAAG

GTCACCATGACCTGCAGTGCCACCTCAAGTATAACTTACATGTCCTGGTACCAGCAGAAG

TCAGGATCCTCCCCCAGACTCCTGATTTATGACACATCCAACCTGGCTTCTGGAGTCCCT

GTTCGCTTCAGTGGCAGTGGGTCTGGGACCTCTTACTCTCTCACAATCAGCCGAATGGAG

GCTGAAGATGCTGCCACTTATTACTGCCAGCAGTGGAGTAGTTACCCGCTCACGTTCGGT

GCTGGGACCAAGCTGGAGCTGAAA

Example 7

Preparation of a Humanized Version of antibody 26.

The human framework IC4 was chosen for the humanization of both the light and heavy chain V genes of antibody 26. IC4-Vκ is of human subclass Vκ-1 with 63% amino acid sequence identity with the Vκ of CTLA4-26B in the framework. IC4-VH is of human subclass VH-2 with 69% amino acid sequence identity with the VH of CTLA4-26B in the framework. The 3 CDR regions of both the light and heavy chain V genes are unchanged in the humanized version. Certain framework residues predicted to have significant contact with the CDRs or that have important function in maintaining structural integrity also remain unchanged. In addition, a number of amino acids identified as unusual or rare at their positions for their respective human subgroups were changed to the consensus amino acid at that position. The final humanized sequences of the variable regions of the light and heavy chains are shown below.

Eight long oligodeoxynucleotides for each of the VH and VL were synthesized and assembled to yield the entire VH or VL sequence through Klenow extension He et al. (1998) *J. Immunol.* 160:1029–1035). This final product was then amplified by PCR and digested with XbaI. The VH fragment was subcloned into the pVγ1, pVγ2m3, and pVγ4 expression vectors (Co et al. (1992) *J. Immunol.* 148:1149–1154; Cole et al. (1998) *J. Immunol.* 159:3613–3621) to yield plasmids pVγ1$_{HC}$, pVγ2m3$_{HC}$, and pVγ4$_{HC}$, respectively. The VL fragment was subcloned into the pVκ expression vector to produce the plasmid pVκ$_{LC}$.

Transient transfections of COS-7 cells with humanized anti-CTLA4 plasmids were performed using 1.5 µg and 3.0 µg of light and heavy chain plasmids respectively. All light chain and heavy chain combinations were set up (pVκ$_{LC}$+pVγ1$_{HC}$, pVγ2m3$_{HC}$, and pVγ4$_{HC}$). The growth media used was a low Ig growth media (DMEM+2% Low Ig FBS+L-Glu). The supernatants were used in a FACS assay to determine the binding to CTLA4. The production levels of transiently expressed antibody was determined by ELISAs.

Supernatants of transient transfections of COS-7 cells with pVκ$_{LC}$+pVγ1$_{HC}$, and pVκ$_{LC}$+pVγ4$_{HC}$ were used in a FACS assay to determine the titer point of the humanized antibodies as compared to the murine anti-CTLA4. While this is a qualitative assay, it gives a general indication of the binding of the humanized antibodies and shows qualitatively whether the humanized antibodies are within 3- to 10-fold the binding of the mouse Ab. In order to perform this test, the supernatants were diluted to the lowest common concentration (as determined by ELISA assay).

Stable transfections were also performed with various plasmid combinations (pVκ$_{LC}$+pVγ1$_{HC}$, pVγ2m3$_{HC}$, and pVγ4$_{HC}$) in order to obtain higher yields of humanized antibodies for purification for use in more quantitative experiments. All plasmids were linearized with Fsp I except pVγ4$_{HC}$ plasmid, which was linearized with BstZ17I. 30 µg of light chain plasmid and 60 µg of heavy chain plasmid were linearized and used in stable transfections of Sp2/0 cells by electroporation as described by Co et al. (1992) *J. Immunol.* 148:1149–1154.

The nucleotide and amino acid sequences of humanized anti-CTLA4 antibody number 26 VK region is shown in FIG. 9 (SEQ ID NOs:7 and 8). The nucleotide and amino acid sequences of humanized anti-CTLA4 antibody number 26 VH region is shown in FIG. 10 (SEQ ID NOS:9 and 10).

A comparison of murine and humanized anti-CTLA4 number 26 VH and VK regions are shown below:

VH
Human ...–AVLVLFLCLVAFPSC (SEQ ID NO:10)
Murine ...MDVLVLFLCLVAFPSC (SEQ ID NO:4)

VLSQVQLQESG PGLVKPSQT
VLSQVQLKESG PGLVAPSQS

LSLTCTVSGFSL TSYGVYWV
LSITCTVSGFSL TSYGVYWV

RQPPGKGLEWL GVIWAGGTT
RQPPGKGLEWL GVIWAGGTT

NYNSALMSRLT ISKDTSKNQ
NYNSALMSRLS ISKDNSKSQ

VSLKLSSVTAA DTAVYYCAR
VFLKMSSLQTD DTAMYYCAR

GPPHAMMKRGY AMDYWGQGT
GPPHAMMKRGY AMDYWGQGT

LVTVSS
SVIVSS

Vk
Humanized – DFQVQIFS FLLISAS (SEQ ID NO:8)
Murine ...MDFQVQIF SFLLISAS (SEQ ID NO:6)

VILSRGDIQMT QSPSSLSAS
VILSRGQNVLT QSPAIMPAS

VGDRVTITCSA TSSSITYMSW
PGEKVTMTCSA TSSSITYMSW

YQQKPGKAPKL LIYDTSNLA
YQQKSGSSPRL LIYDTSNLA

SGVPSRFSGSG SGTDYTLTI
SGVPVRFSGSG SGTSYSLTI

SSLQPEDFATY YCQQWSSYP
SRMEAEDAATY YCQQWSSYP

LTFGGGTKVEI K
LTFGAGTKLEL K

Example 8

Comparison of murine anti-human CTLA4 with three isotypes of humanized anti-CTLA4 for their ability to bind to CTLA4Ig in an ELISA.

The relative affinity of the humanized anti-CTLA4 (hCTLA4-26B) and murine anti-CTLA4 (mCTLA4-26B) for CTLA4 was assessed using competition ELISAs. Plates were coated with human CTLA4-Ig (10 ug/ml) overnight, washed the next day and blocked with Superblock (Pierce) for 15 min at room temperature. Plates were washed three times with 1×PBS/0.1% Tween 20 and three times with 1× PBS.

In a separate mixing plate, 15 ng/ml of biotinylated humanized CTLA4Ig [hIgG1 isotype] or humanized CTLA4Ig4 [hIgG4 isotype]) was prepared. 100 ul of antibody mixtures was transferred to human CTLA4-Ig coated ELISA plate and rocked for 2 hours at room temperature. Plates were washed as described above and a secondary reagent (streptavidin peroxidase conjugate at 1:1000 dilution) in PBT buffer (1×PBS, 1% BSA, 0.1% Tween 20 was added. Plates were incubated for 1 hr at RT with shaking. Plates were washed as described above and developed for 10 minutes at room temperature with ABTS+H2O2 (100 ul/well) and the reaction was stopped with 2% oxalic acid (100 ul/well).

As shown in FIG. 5, the humanized versions of anti-CTLA4 (the IgG1, IgG4, and IgG2m3 (2 mutated 3) isotypes) are able to compete for biotinylated murine CTLA4-26B for binding to human CTLA4Ig. These data indicate that the affinity of the humanized antibodies is very similar (at least within 10-fold of the murine anti-CTLA4 antibody) to that of the murine antibody.

For FACS analysis the subsaturating concentration of the FITC-labeled murine CTLA4-26B was determined using CTLA4-expressing CHO cells. 125 ng FITC-labeled murine anti-CTLA4 was combined with varying concentrations of unlabeled competitors, including murine anti-CTLA4 and the humanized anti-CTLA4 IgG1 isotype (IgG1/κ) using CTLA4-expressing CHO cells. The starting concentration of the unlabeled competitor was 2000 ng and was diluted 2-fold serially to 100 ng. Humanized antibody 26 of the IgG1 isotype showed binding affinity with in 3-fold of the murine antibody.

The affinity of the murine anti-CTLA4 antibody was calculated to be about Kd=$1.7 \times 10^{-9}$. The humanized versions were calculated to have affinities of about $2 \times 10^{-9}$ for the IgG1 isotype, $1.1 \times 10^{-9}$ for the IgG4 isotype, and about $1.2 \times 10^{-9}$ for IgG2m3 isotype.

Example 8

Elimination of activated T cells using anti-CTLA4 antibodies conjugated to small molecules or toxic moieties.

Jurkat T cells were transfected with an empty vector (A) or a CTLA4 expression vector (B). Cells were selected for hygromycin resistance and expression of CTLA4 was confirmed by FACS. Jurkat T cells were incubated with various concentrations of anti-CTLA4 antibody (number 26 or 33) conjugated to a small molecule (calicheamicin) using amide conjugation or carbohydrate-based conjugation. A control antibody (MPHANT) conjugated to the same small molecule was also used. Cell proliferation was measured after 48 hours of culture by labeling with thymidine for the last 12 hours of culture.

Cells expressing CTLA4 exhibit decreased proliferation in the presence of anti-CTLA4-toxic moiety conjugates. Control MPHANT antibody conjugated to calicheamicin had no effect on the proliferation of untransfected or transfected Jurkat cells. Thus, these data show that activated T cells can be targeted using anti-CTLA4-specific antibodies.

Example 9

Blockade of CTLA4 engagement by a humanized anti-CTLA4 antibody results in enhanced T cell responses.

Jurkat T cell transfected with hCTLA4 ($10^6$ cells/ml) were stimulated with latex beads coated with anti-hCD3+ CD86-Ig in the presence or absence of increasing concentrations of soluble anti-CTLA4 Ab (5–20 μg/ml) or IgG control (20 μg/ml). Supernatents were harvested at 72 hours and IL-2 production assessed using a commercially available hIL-2 ELISA kit (R&D Systems, MA).

Soluble humanized anti-CTLA4-26B (Hu-26B) inhibits the interaction of CTLA4 with its natural ligands (CD86) and thus, enhances T cell responses as assessed by IL-2 production. Increased IL-2 production levels were obtained in the presence of Hu-26B (compared with control Ig). The ability of this humanized antibody to functionally enhance T cell responses is comparable to that of the murine antibody (Mu-26B) from which is was derived (FIG. 11).

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A humanized antibody that is specifically reactive with human CTLA4, wherein the antibody comprises the amino acid sequence shown in SEQ ID NO: 8.

2. A humanized antibody that is specifically reactive with human CTLA4, wherein the antibody comprises the amino acid sequence shown in SEQ ID NO: 10.

* * * * *